(12) United States Patent
Lingard et al.

(10) Patent No.: US 9,308,194 B2
(45) Date of Patent: Apr. 12, 2016

(54) INDANYLOXYPHENYLCYCLOPROPANE CARBOXYLIC ACIDS

(71) Applicant: Boehringer Ingelheim International GmbH, Ingelheim am Rhein (DE)

(72) Inventors: Iain Lingard, Monza (IT); Dieter Hamprecht, Pozzolengo (IT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/552,515

(22) Filed: Nov. 25, 2014

(65) Prior Publication Data

US 2015/0148347 A1 May 28, 2015

(30) Foreign Application Priority Data

Nov. 28, 2013 (EP) ..................... 13194945

(51) Int. Cl.
| | | |
|---|---|---|
| A61K 31/5375 | (2006.01) | |
| A61K 31/351 | (2006.01) | |
| A61K 31/195 | (2006.01) | |
| A61K 31/194 | (2006.01) | |
| A61K 31/192 | (2006.01) | |
| A61K 31/277 | (2006.01) | |
| C07D 213/61 | (2006.01) | |
| C07D 213/62 | (2006.01) | |
| C07D 213/64 | (2006.01) | |
| C07D 215/20 | (2006.01) | |
| C07D 231/12 | (2006.01) | |
| C07D 231/56 | (2006.01) | |
| C07D 249/08 | (2006.01) | |
| C07D 257/04 | (2006.01) | |
| C07D 271/07 | (2006.01) | |
| C07D 277/64 | (2006.01) | |
| C07D 295/155 | (2006.01) | |
| C07D 295/18 | (2006.01) | |
| C07D 295/192 | (2006.01) | |
| C07D 309/10 | (2006.01) | |
| A61K 45/06 | (2006.01) | |
| C07D 309/12 | (2006.01) | |
| C07C 317/18 | (2006.01) | |
| C07C 65/26 | (2006.01) | |
| C07C 235/46 | (2006.01) | |
| C07C 235/48 | (2006.01) | |
| C07D 309/14 | (2006.01) | |
| C07C 255/54 | (2006.01) | |
| C07C 317/22 | (2006.01) | |
| C07D 271/06 | (2006.01) | |
| C07D 295/088 | (2006.01) | |
| C07C 62/34 | (2006.01) | |

(52) U.S. Cl.
CPC ............. *A61K 31/277* (2013.01); *A61K 31/192* (2013.01); *A61K 31/194* (2013.01); *A61K 31/195* (2013.01); *A61K 31/351* (2013.01); *A61K 31/5375* (2013.01); *A61K 45/06* (2013.01); *C07C 62/34* (2013.01); *C07C 65/26* (2013.01); *C07C 235/46* (2013.01); *C07C 235/48* (2013.01); *C07C 255/54* (2013.01); *C07C 317/18* (2013.01); *C07C 317/22* (2013.01); *C07D 213/61* (2013.01); *C07D 213/62* (2013.01); *C07D 213/64* (2013.01); *C07D 215/20* (2013.01); *C07D 231/12* (2013.01); *C07D 231/56* (2013.01); *C07D 249/08* (2013.01); *C07D 257/04* (2013.01); *C07D 271/06* (2013.01); *C07D 277/64* (2013.01); *C07D 295/088* (2013.01); *C07D 295/155* (2013.01); *C07D 295/18* (2013.01); *C07D 295/192* (2013.01); *C07D 309/10* (2013.01); *C07D 309/12* (2013.01); *C07D 309/14* (2013.01); *C07C 2102/02* (2013.01); *C07C 2102/08* (2013.01)

(58) Field of Classification Search
CPC .. C07C 317/22; C07C 317/18; C07C 255/54; C07C 235/48; C07C 235/46; C07C 65/26; C07C 62/34; C07D 309/12; C07D 309/14; C07D 309/10; C07D 295/192; C07D 295/18; C07D 295/155; C07D 295/088; C07D 277/64; C07D 271/06; C07D 257/04; C07D 249/08; C07D 231/56; C07D 231/12; C07D 215/20; C07D 213/64; C07D 213/62; C07D 213/61; A61K 31/5375; A61K 31/351; A61K 31/195; A61K 31/194; A61K 31/192; A61K 31/277
See application file for complete search history.

(56) References Cited

U.S. PATENT DOCUMENTS

2011/0053974 A1    3/2011   Toda et al.

OTHER PUBLICATIONS

Negoro, et al., Journal of Medicinal Chemistry, 2012, vol. 55, No. 4, "Idetification of Fused-Ring Alkanoic Acids with Improved Pharmacokinetic Profiles that Act as G Protein-Coupled Receptor 40/Free Fatty Acid Receptor 1 Agonists", p. 1538-1552.
Mikami, et al., "Discovery of Phenylpropanoic Acid Derivatives Containing Polar Functionalities as Potent and Orally Bioavailable G Protein-Coupled Receptor 40 Agonists for the Treatment of Type 2 Diabetes", 2012, vol. 55, No. 8, p. 3756-3776.
International Search Report and Written opinion, PCT/ISA 220, mailed Feb. 19, 2015.

*Primary Examiner* — Rebecca Anderson
(74) *Attorney, Agent, or Firm* — Michael P. Morris; Alan R. Stempel

(57) ABSTRACT

A compound of formula I,

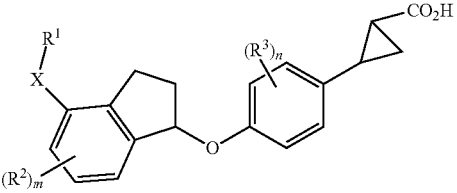

wherein the groups $R^1$, $R^2$, $R^3$, X, m, and n are defined as in claim 1, which have valuable pharmacological properties, in particular bind to the GPR40 receptor and modulate its activity. The compounds are suitable for treatment and prevention of diseases which can be influenced by this receptor, such as metabolic diseases, in particular diabetes type 2. Furthermore, the invention relates to novel intermediates, useful for the synthesis of compounds of formula I.

13 Claims, No Drawings

INDANYLOXYPHENYLCYCLOPROPANE CARBOXYLIC ACIDS

FIELD OF THE INVENTION

The present invention relates to novel indanyloxyphenylcyclopropanecarboxylic acids, that are agonists of the G-protein coupled receptor 40 (GPR40, also known as free fatty acid receptor FFAR 1), to processes for their preparation, to pharmaceutical compositions containing these compounds and to their medical use for the prophylaxis and/or treatment of diseases which can be influenced by the modulation of the function of GPR40. Particularly, the pharmaceutical compositions of the invention are suitable for the prophylaxis and/or therapy of metabolic diseases, such as diabetes, more specifically type 2 diabetes mellitus, and conditions associated with the disease, including insulin resistance, obesity, cardiovascular disease and dyslipidemia.

BACKGROUND OF THE INVENTION

Metabolic diseases are diseases caused by an abnormal metabolic process and may either be congenital due to an inherited enzyme abnormality or acquired due to a disease of an endocrine organ or failure of a metabolically important organ such as the liver or the pancreas.

Diabetes mellitus is a disease state or process derived from multiple causative factors and is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Persistent or inadequately controlled hyperglycemia is associated with a wide range of pathologies. Diabetes is a very disabling disease, because today's common antidiabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, stroke, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

The free fatty acid receptor GPR40 (also referred to as either FFAR, FFAR1, or FFA1) is a cell-surface receptor and a member of the gene superfamily of G-protein coupled receptors, which was first identified as a so-called orphan receptor, i.e. a receptor without a known ligand, based on the predicted presence of seven putative transmembrane regions in the corresponding protein (Sawzdargo et al. (1997) Biochem. Biophys. Res. Commun. 239: 543-547). GPR40 is found to be highly expressed in several particular cell types: the pancreatic 13 cells and insulin-secreting cell lines, as well as in enteroendocrine cells, taste cells, and is reported to be expressed in immune cells, splenocytes, and in the human and monkey brain. Meanwhile, fatty acids of varying chain lengths are thought to represent the endogenous ligands for GPR40, activation of which is linked primarily to the modulation of the Gq family of intra-cellular signaling G proteins and concomitant induction of elevated calcium levels, although activation of Gs- and Gi-proteins to modulate intracellular levels of cAMP have also been reported. GPR40 is activated especially by long-chain FFA, particularly oleate, as well as the PPAR-gamma agonist rosiglitazone.

It has been recognized that the fatty acids that serve as activators for GPR40 augment the elevated plasma glucose-induced secretion of insulin through GPR40 receptors that are expressed in the insulin secreting cells (Itoh et al. (2003) Nature 422: 173-176; Briscoe et al. (2003) J. Biol. Chem. 278: 11303-11311; Kotarsky et al. (2003) Biochem. Biophys. Res. Commun. 301: 406-410). Despite initial controversy, the use of GPR40 agonist appears to be the appropriate for increasing insulin release for the treatment of diabetes (see, e.g., Diabetes 2008, 57, 2211; J. Med. Chem. 2007, 50, 2807). Typically, long term diabetes therapy leads to the gradual diminution of islet activity, so that after extended periods of treatment Type 2 diabetic patients need treatment with daily insulin injections instead. GPR40 agonists may have the potential to restore or preserve islet function, therefore, GPR40 agonists may be beneficial also in that that they may delay or prevent the diminution and loss of islet function in a Type 2 diabetic patient.

It is well established that the incretins GLP-1 (glucagon-like peptide-1) and GIP (glucose-dependent insulinotropic peptide; also known as gastric inhibitory peptide) stimulate insulin secretion and are rapidly inactivated in vivo by DPP-4. These peptidyl hormones are secreted by endocrine cells that are located in the epithelium of the small intestine. When these endocrine cells sense an increase in the concentration of glucose in the lumen of the digestive tract, they act as the trigger for incretin release. Incretins are carried through the circulation to beta cells in the pancreas and cause the beta cells to secrete more insulin in anticipation of an increase of blood glucose resulting from the digesting meal. Further studies indicating that the GPR40 modulatory role on the release of incretins from the enteroendocrine cells, including CCK, GLP-1, GIP, PYY, and possibly others, suggest that GPR40 modulators may contribute to enhanced insulin release from the pancreatic beta cells also indirectly by e.g. a synergistic effect of GLP-1 and possibly GIP on the insulin release, and the other release incretins may also contribute to an overall beneficial contribution of GPR40 modulation on metabolic diseases. The indirect contributions of GPR40 modulation on insulin release through the elevation of plasma levels of incretins may be further augmented by the coadministration of inhibitors of the enzymes responsible for the incretin degradation, such as inhibitors of DPP-4.

Insulin imbalances lead to conditions such as type II diabetes mellitus, a serious metabolic disease. The modulation of the function of GPR40 in modulating insulin secretion indicates the therapeutic agents capable of modulating GPR40 function could be useful for the treatment of disorders such as diabetes and conditions associated with the disease, including insulin resistance, obesity, cardiovascular disease and dyslipidemia.

OBJECT OF THE PRESENT INVENTION

The object of the present invention is to provide new compounds, hereinafter described as compounds of formula I, in particular new indanyloxyphenylcyclopropanecarboxylic acids, which are active with regard to the G-protein-coupled receptor GPR40, notably are agonists of the G-protein-coupled receptor GPR40.

A further object of the present invention is to provide new compounds, in particular new indanyloxyphenylcyclopropanecarboxylic acids, which have an activating effect on the G-protein-coupled receptor GPR40 in vitro and/or in vivo and possess suitable pharmacological and pharmacokinetic properties to use them as medicaments.

A further object of the present invention is to provide effective GPR40 agonists, in particular for the treatment of metabolic disorders, for example diabetes, dyslipidemia and/or obesity.

A further object of the present invention is to provide methods for treating a disease or condition mediated by the activation the G-protein-coupled receptor GPR40 in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

GPR40 modulators are known in the art, for example, the compounds disclosed in WO 2004041266 (EP 1559422), WO 2007033002 and WO 2009157418. The indanyloxyphenylcyclopropanecarboxylic acids of the present invention may provide several advantages, such as enhanced potency, high metabolic and/or chemical stability, high selectivity and tolerability, enhanced solubility, and the possibility to form stable salts.

SUMMARY OF THE INVENTION

In a first aspect the invention relates to a compound of formula

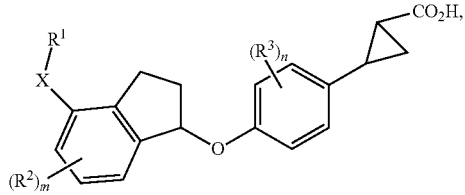

I wherein
R$^1$ is selected from the group R$^1$-G1 consisting of a phenyl ring, a tetrazolyl ring, a 5-membered heteroaromatic ring containing 1 —NH—, —O—, or —S— group, a 5-membered heteroaromatic ring containing 1 —NH—, —O—, or —S— group and additionally 1 or 2 =N— atoms,
a 6-membered heteroaromatic ring containing 1, 2 or 3 =N— atoms,
  wherein optionally a second ring is annulated to the phenyl ring or to the 5- or 6-membered heteroaromatic rings and the second ring is 5- or 6-membered, unsaturated or aromatic and may contain 1, 2, or 3 heteroatoms independently of each other selected from =N—, —NH—, —O—, and —S— with the proviso that only up to two of the heteroatoms are O and S and no O—O, S—S, and S—O bond is formed, and wherein in the second ring independently of the presence of heteroatoms 1 or 2 CH$_2$ groups may be replaced by —C(O)—, —S(O)—, or —S(O)$_2$—, and
  wherein the phenyl ring, tetrazolyl ring, 5- or 6-membered heteroaromatic ring, annulated phenyl ring, and annulated 5- or 6-membered heteroaromatic ring are optionally substituted at a carbon atom with one group R$^{1a}$; and
  wherein the phenyl ring, tetrazolyl ring, 5- or 6-membered heteroaromatic ring, annulated phenyl ring, and annulated 5- or 6-membered heteroaromatic ring are optionally additionally substituted at carbon atoms with 1 to 3 groups independently selected from R$^{1b}$; and
  wherein the H-atom in one or more NH groups present in the tetrazolyl ring, 5- or 6-membered heteroaromatic ring, annulated phenyl ring, or annulated 5- or 6-membered heteroaromatic ring optionally is replaced by R$^M$;
R$^2$ is selected from the group R$^2$-G1 consisting of F, Cl, Br, I, C$_{1-4}$-alkyl, C$_{3-6}$-cycloalkyl, NC—, H$_2$N—C(O)—, C$_{1-4}$-alkyl-NR$^M$—C(O)—, C$_{1-4}$-alkyloxy, and C$_{1-4}$-alkyl-S(O)$_2$—,
  wherein any alkyl and cycloalkyl group or sub-group within the groups mentioned is optionally substituted with one or more F atoms, and wherein multiple R$^2$ may be identical or different, if m is 2 or 3;
R$^3$ is selected from the group R$^3$-G1 consisting of F, Cl, Br, NC—, C$_{1-6}$-alkyl, C$_{3-6}$-cycloalkyl-, C$_{1-6}$-alkyl-O—, and C$_{3-6}$-cycloalkyl-O—,
  wherein each alkyl and cycloalkyl group and each alkyl and cycloalkyl sub-group within the groups mentioned is optionally substituted with one or more F atoms;
X is selected from the group X-G1 consisting of —O—, >S=O, >S(=O)$_2$, —CH$_2$—, and —S—;
m is an integer selected from 0, 1, 2, and 3;
n is an integer selected from 0, 1, and 2;
R$^{1a}$ is selected from the group R$^{1a}$-G1 consisting of
  C$_{1-6}$-alkyl, C$_{2-6}$-alkenyl, C$_{2-6}$-alkinyl, C$_{3-6}$-cycloalkyl-, C$_{3-6}$-cycloalkyl-C$_{1-6}$-alkyl, C$_{1-4}$-alkyl-NH—, (C$_{1-4}$-alkyl)$_2$N—, —NHR$^N$, HNR$^M$—C(O)—, C$_{1-4}$-alkyl-NR$^M$—C(O)—, C$_{1-6}$-alkyl-O—, C$_{3-6}$-cycloalkyl-O—, C$_{3-6}$-cycloalkyl-C$_{1-6}$-alkyl-O—, C$_{1-4}$-alkyl-S—, C$_{1-4}$-alkyl-S(O)—, C$_{1-4}$-alkyl-S(O)$_2$, and aryl-C$_{1-3}$-alkyl-O—,
    wherein a —CH$_2$— member within a C$_{4-6}$-cycloalkyl-group or sub-group within the groups mentioned optionally is replaced by —NR$^N$—, —O—, —S—, —S(O)—, or —S(O$_2$)—, or
    wherein a >CH—CH$_2$— member or a —CH$_2$—CH$_2$— member within a C$_{5-6}$-cycloalkyl- group or sub-group within the groups mentioned optionally is replaced by >N—C(O)—, >N—S(O)—, >N—S(O)$_2$—, —N(R$^M$)—C(O)—, —N(R$^M$)—S(O)—, or —N(R$^M$)—S(O)$_2$—, and wherein each alkyl and cycloalkyl group and each alkyl and cycloalkyl sub-group within the groups mentioned optionally is substituted with HO—, HO—C1-4-alkyl-, C1-4-alkyl-oxy, C$_{1-4}$-alkyl-oxy-C$_{1-4}$-alkyl-, C$_{1-4}$-alkyl-sulfanyl, C$_{1-4}$-alkyl-sulfinyl, C$_{1-4}$-alkyl-sulfonyl, H$_2$N—C(O)—, C$_{1-4}$-alkyl-NH—C(O)—, (C$_{1-4}$-alkyl)$_2$N—C(O)—, or C$_{3-6}$-cycloalkyl-NR$^M$—C(O)—, and/or optionally substituted with one or more F atoms;

a phenyl ring, a tetrazolyl ring, a 5-membered heteroaromatic ring containing 1 —NH—, —O—, or —S— group, a 5-membered heteroaromatic ring containing 1 —NH—, —O—, or —S— group and additionally 1 or 2 =N— atoms, a 6-membered heteroaromatic ring containing 1, 2, or 3 =N— atoms, wherein the rings are optionally substituted with one or more groups selected from R$^{1b}$; and wherein the H-atom in one or more NH groups present in the tetrazolyl ring or 5-membered heteroaromatic ring is replaced by R$^M$;

R$^{1b}$ is selected from the group R$^{1b}$-G1 consisting of F, Cl, CN, —OH, C$_{1-4}$-alkyl, C$_{3-6}$-cycloalkyl-, HO—C$_{1-4}$-alkyl, C$_{1-4}$-alkyl-O—O$_{1-4}$-alkyl, C$_{1-4}$-alkyl-O—, C$_{3-6}$-cycloalkyl-O—, C$_{1-4}$-alkyl-O—O$_{1-4}$-alkyl-O—, C$_{1-4}$-alkyl-S—, C$_{1-4}$-alkyl-S(O)—, and C$_{1-4}$-alkyl-S(O)$_2$—, wherein any alkyl and cycloalkyl group or sub-group within the groups mentioned is optionally substituted with one or more F atoms;

R$^N$ is independently of each other selected from the group R$^N$-G1 consisting of H, C$_{1-4}$-alkyl, HO—C$_{2-4}$-alkyl (with the proviso that at least 2 carbon atoms are between the HO-group and an NH), C$_{1-4}$-alkyl-O—C$_{2-4}$-alkyl- (with the proviso that at least 2 carbon atoms are between an O-group and an NH), C$_{1-4}$-alkyl-C(O)—, C$_{1-4}$-alkyl-O—C(O)—, and C$_{1-4}$-alkyl-S(O)$_2$—;

wherein any alkyl group or sub-group within the groups mentioned is optionally substituted with one or more F atoms;

R$^M$ is independently of each other selected from the group R$^M$-G1 consisting of H, C$_{1-4}$-alkyl, HO—C$_{2-4}$-alkyl (with the proviso that at least 2 carbon atoms are between the HO-group and an NH), and C$_{1-4}$-alkyl-O—C$_{2-4}$-alkyl- (with the proviso that at least 2 carbon atoms are between an O-group and an NH);

wherein any alkyl group or sub-group within the groups mentioned is optionally substituted with one or more F atoms;

wherein in any definition mentioned hereinbefore and if not specified otherwise, any alkyl group or sub-group may be straight-chained or branched, the isoforms, tautomers, stereoisomers, metabolites, prodrugs, solvates, hydrates, and the salts thereof, particularly the physiologically acceptable salts thereof with inorganic or organic acids or bases, or the combinations thereof.

The extension -Gn used within the definitions is meant to identify genus n of the respective substituent. For example, R$^1$-G1 defines genus 1 of the substituent R$^1$.

The expression "optionally substituted with one or more F atoms" means that none or one up to successively all H atoms bound to carbon atoms of the respective group or submoiety may be replaced by F atoms, preferably 1 to 5 H atoms or, more preferred, 1 to 3 H atoms may be replaced by F atoms.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the G-protein-coupled receptor GPR40 in a patient in need thereof characterized in that a compound of general formula I or a pharmaceutically acceptable salt thereof is administered to the patient.

According to another aspect of the invention, there is provided a method for treating a metabolic disease or disorder, such as diabetes, dyslipidemia, and/or obesity, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the G-protein-coupled receptor GPR40 in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the activation of the G-protein-coupled receptor GPR40.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly R$^1$, R$^2$, R$^3$, X, m, and n are defined as above and hereinafter. If residues, substituents, or groups occur several times in a compound, they may have the same or different meanings. Some preferred meanings of individual groups and substituents of the compounds according to the invention will be given hereinafter. Any and each of these definitions may be combined with each other.

R$^1$:

R$^1$-G1:

The group R$^1$ is preferably selected from the group R$^1$-G1 as defined hereinbefore.

R$^1$-G2:

According to one embodiment the group $R^1$ is selected from the group $R^1$-G2 consisting of
a phenyl ring, a tetrazolyl ring,
a 5-membered heteroaromatic ring containing 1 —NH— or —O-group,
a 5-membered heteroaromatic ring containing 1 —NH— or —O— group and additionally 1 or 2 =N— atoms,
a 6-membered heteroaromatic ring containing 1, 2 or 3 =N— atoms,
wherein the phenyl ring, tetrazolyl ring and 5- or 6-membered heteroaromatic ring are optionally substituted at a carbon atom with one group $R^{1a}$; and
wherein the phenyl ring, tetrazolyl ring, 5- or 6-membered heteroaromatic ring are optionally additionally substituted at carbon atoms with 1 to 3 groups independently selected from $R^{1b}$; and
wherein the H-atom in one or more NH groups present in the tetrazolyl ring, 5- or 6-membered heteroaromatic ring optionally is replaced by $R^M$.

$R^1$-G3:

According to one embodiment the group $R^1$ is selected from the group $R^1$-G3 consisting of wherein any of the phenyl ring, the 6-membered heteroaromatic rings and the fused bicyclic heteroaromatic rings specified above are optionally substituted at a carbon atom with one group $R^{1a}$; and
are optionally additionally substituted at carbon atoms with 1 or 2 groups independently selected from $R^{1b}$, and wherein a H-atom bound to a N-atom optionally is replaced by the group $R^M$.

$R^1$-G4a:

In another embodiment the group $R^1$ is selected from the group $R^1$-G4a consisting of wherein the phenyl and pyridyl ring are substituted at a carbon atom with one group $R^{1a}$; and
are optionally additionally substituted at carbon atoms with 1 or 2 groups independently selected from $R^{1b}$.

$R^1$-G4b:

In another embodiment the group $R^1$ is selected from the group $R^1$-G4 consisting of wherein any of the fused bicyclic heteroaromatic rings specified above are optionally substituted at a carbon atom with one group $R^{1a}$; and
are optionally additionally substituted at carbon atoms with 1 or 2 groups independently selected from $R^{1b}$, and wherein a H-atom bound to a N-atom optionally is replaced by the group $R^M$.

$R^1$-G5:

In another embodiment the group $R^1$ is selected from the group $R^1$-G5 consisting of wherein the phenyl ring is substituted with one group $R^{1a}$; and is optionally additionally substituted at with 1 or 2 groups independently selected from $R^{1b}$.

$R^2$:

$R^2$-G1:

The group $R^2$ is preferably selected from the group $R^2$-G1 as defined hereinbefore.

$R^2$-G2:

In another embodiment the group $R^2$ is selected from the group $R^2$-G2 consisting of F, Cl, Br, I, $C_{1-3}$-alkyl, $C_{3-6}$-cycloalkyl, NC—, $H_2N$—C(O)—, and $C_{1-3}$-alkyloxy,
wherein any alkyl and cycloalkyl group or sub-group within the groups mentioned is optionally substituted with 1 to 3 F atoms, and wherein multiple $R^2$ may be identical or different, if m is 2 or 3.

$R^2$-G3:

In another embodiment the group $R^2$ is selected from the group $R^2$-G3 consisting of F, Cl, $CF_3$, and NC—,
wherein multiple $R^2$ may be identical or different, if m is 2 or 3.

$R^3$:

$R^3$-G1:

The group $R^3$ is preferably selected from the group $R^3$-G1 as defined hereinbefore.

$R^3$-G2:

In another embodiment the group $R^3$ is selected from the group $R^3$-G2 consisting of F, Cl, Br, NC—, $C_{1-4}$-alkyl, $C_{3-6}$-cycloalkyl-, $C_{1-4}$-alkyl-O—, and $C_{3-6}$-cycloalkyl-O—,
wherein each alkyl and cycloalkyl group and each alkyl and cycloalkyl sub-group within the groups mentioned is optionally substituted with 1 to 3 F atoms.

$R^3$-G3:

In another embodiment the group $R^3$ is selected from the group $R^3$-G3 consisting of F, Cl, Br, NC—, $C_{1-3}$-alkyl, and $C_{1-3}$-alkyl-O—,
  wherein each alkyl group and each alkyl sub-group within the groups mentioned is optionally substituted with 1 to 3 F atoms.

$R^3$-G4:

In another embodiment the group $R^3$ is selected from the group $R^3$-G4 consisting of F, Cl, Br, $H_3C$—, $F_3C$—, $H_3C$—O—, and $F_3C$—O—.

$R^3$-G5:

In another embodiment the group $R^3$ is selected from the group $R^3$-G5 consisting of F, Cl, Br, $H_3C$—, and $H_3C$—O—.

X:

X-G1:

The group X is preferably selected from the group X-G1 as defined hereinbefore.

X-G2:

In another embodiment the group X is selected from the group X-G2 consisting of —O—, >S=O, >S(=O)$_2$, and —CH$_2$—.

X-G3:

In another embodiment the group X is selected from the group X-G3 consisting of —O—, >S=O, and >S(=O)$_2$.

X-G4:

In another embodiment the group X is selected from the group X-G4 consisting of —O—, m denotes preferably 0, 1 or 2, particularly preferred is 0 or 1.
n denotes preferably 0 or 1.

$R^{1a}$-G1:

The group $R^{1a}$ is preferably selected from the group $R^{1a}$-G1 as defined hereinbefore.

$R^{1a}$-G2a:

According to one embodiment the group $R^{1a}$ is selected from the group $R^{1a}$-G2a consisting of
  $C_{1-4}$-alkyl, $C_{2-4}$-alkenyl, $C_{2-4}$-alkinyl, $C_{3-6}$-cycloalkyl-, $C_{3-6}$-cycloalkyl-$C_{1-4}$-alkyl, $C_{1-4}$-alkyl-NH—, ($C_{1-4}$-alkyl)$_2$N—, —NHR$^N$, HNR$^M$—C(O)—, $C_{1-4}$-alkyl-NR$^M$—C(O)—, $C_{1-6}$-alkyl-O—, $C_{3-6}$-cycloalkyl-O—, $C_{3-6}$-cycloalkyl-$C_{1-4}$-alkyl-O—, $C_{1-4}$-alkyl-S(O)$_2$, and aryl-$C_{1-3}$-alkyl-O—,
  wherein a —CH$_2$— member within a $C_{4-6}$-cycloalkyl- group or sub-group within the groups mentioned optionally is replaced by —NR$^N$—, —O—, or —S(O$_2$)—, or wherein a >CH—CH$_2$— member or a —CH$_2$—CH$_2$— member within a $C_{5-6}$-cycloalkyl- group or sub-group within the groups mentioned optionally is replaced by >N—C(O)—, >N—S(O)$_2$—, —N(R$^M$)—C(O)—, or —N(R$^M$)—S(O)$_2$—, and wherein each alkyl and cycloalkyl group and each alkyl and cycloalkyl sub-group within the groups mentioned optionally is substituted with HO—, HO—$C_{1-3}$-alkyl-, $C_{1-3}$-alkyl-oxy, $C_{1-3}$-alkyloxy-$C_{1-4}$-alkyl-, $C_{1-4}$-alkyl-sulfonyl, $H_2N$—C(O)—, $C_{1-4}$-alkyl-NH—C(O)—, or ($C_{1-4}$-alkyl)$_2$N—C(O)—, and/or optionally substituted with 1 to 3 F atoms.

$R^{1a}$-G2b:

According to one embodiment the group $R^{1a}$ is selected from the group $R^{1a}$-G2b consisting of
  a phenyl ring, a tetrazolyl ring,
  a 5-membered heteroaromatic ring containing 1 —NH— or —O— group,
  a 5-membered heteroaromatic ring containing 1 —NH— or —O— group and additionally 1 or 2 =N— atoms,
  a 6-membered heteroaromatic ring containing 1 or 2 =N— atoms, wherein the rings are optionally substituted with one to three groups selected from $R^{1b}$; and
  wherein the H-atom in one or more NH groups present in the tetrazolyl ring or 5-membered heteroaromatic ring is replaced by $R^M$.

$R^{1a}$-G3a:

According to one embodiment the group $R^{1a}$ is selected from the group $R^{1a}$-G3a consisting of
  $C_{1-4}$-alkyl, $C_{3-6}$-cycloalkyl-, $C_{3-6}$-cycloalkyl-$C_{1-4}$-alkyl, HNR$^M$—C(O)—, $C_{1-4}$-alkyl-NR$^M$—C(O)—, $C_{1-6}$-alkyl-O—, $C_{3-6}$-cycloalkyl-O—, $C_{3-6}$-cycloalkyl-$C_{1-3}$-alkyl-O—, and aryl-$C_{1-3}$-alkyl-O—,
  wherein a —CH$_2$— member within a $C_{4-6}$-cycloalkyl-group or sub-group within the groups mentioned optionally is replaced by —NR$^N$—, —O—, or —S(O$_2$)—, or wherein a >CH—CH$_2$— member or a —CH$_2$—CH$_2$— member within a $C_{5-6}$-cycloalkyl-group or sub-group within the groups mentioned optionally is replaced by >N—S(O)$_2$—, or —N(R$^M$)—S(O)$_2$—, and
  wherein each alkyl and cycloalkyl group and each alkyl and cycloalkyl sub-group within the groups mentioned optionally is substituted with HO—, HO—$C_{1-3}$-alkyl-, $C_{1-3}$-alkyl-oxy, $C_{1-3}$-alkyl-sulfonyl, $H_2N$—C(O)—, $C_{1-3}$-alkyl-NH—C(O)—, or ($C_{1-3}$-alkyl)$_2$N—C(O)—, and/or optionally substituted with 1 to 3 F atoms.

$R^{1a}$-G3b:

According to one embodiment the group $R^{1a}$ is selected from the group $R^{1a}$-G3b consisting of
  a phenyl ring, a tetrazolyl ring,
  a 5-membered heteroaromatic ring containing 1 —NH— or —O— group,
  a 5-membered heteroaromatic ring containing 1 —NH— or —O— group and additionally 1 or 2 =N— atoms,
  a 6-membered heteroaromatic ring containing 1 =N— atom,
    wherein the rings are optionally substituted with one or two groups selected from $R^{1b}$; and
    wherein the H-atom in one or more NH groups present in the tetrazolyl ring or 5-membered heteroaromatic ring is replaced by $R^M$.

$R^{1a}$-G4a:

According to one embodiment the group $R^{1a}$ is selected from the group $R^{1a}$-G4a consisting of
  $C_{1-4}$-alkyl, $C_{3-6}$-cycloalkyl-, $C_{3-6}$-cycloalkyl-$C_{1-3}$-alkyl, HNR$^M$—C(O)—, $C_{1-3}$-alkyl-NR$^M$—C(O)—, $C_{1-5}$-alkyl-O—, $C_{3-6}$-cycloalkyl-O—, $C_{3-6}$-cycloalkyl-$C_{1-3}$-alkyl-O—, and aryl-$C_{1-3}$-alkyl-O—,
  wherein a —CH$_2$— member within a $C_{4-6}$-cycloalkyl-group or sub-group within the groups mentioned optionally is replaced by —NR$^N$—, —O—, or —S(O$_2$)—, or
  wherein a >CH—CH$_2$— member within a $C_{5-6}$-cycloalkyl- group or sub-group within the groups mentioned optionally is replaced by >N—S(O)$_2$—, and
  wherein each alkyl and cycloalkyl group and each alkyl and cycloalkyl sub-group within the groups mentioned optionally is substituted with HO—, HO—$C_{1-3}$-alkyl-, $C_{1-3}$-alkyl-oxy, $C_{1-3}$-alkyl-sulfonyl or H₂N—C(O)—, and/or optionally substituted with 1 to 3 F atoms.

$R^{1a}$-G4b:

According to one embodiment the group $R^{1a}$ is selected from the group $R^{1a}$-G4b consisting of
a phenyl ring, a tetrazolyl ring,
a 5-membered heteroaromatic ring containing 1 —NH— or —O— group,
a 5-membered heteroaromatic ring containing 1 —NH— or —O— group and additionally 1 or 2 =N— atoms,
wherein the rings are optionally substituted with one group selected from $R^{1b}$; and
wherein the H-atom in one or more NH groups present in the tetrazolyl ring or 5-membered heteroaromatic ring is replaced by $R^M$.

$R^{1a}$-G5a:

According to one embodiment the group $R^{1a}$ is selected from the group $R^{1a}$-G5a consisting of
$HNR^M$—C(O)—, $C_{1-3}$-alkyl-$NR^M$—C(O)—, $C_{1-5}$-alkyl-O—, $C_{3-6}$-cycloalkyl-O—, and $C_{3-6}$-cycloalkyl-$C_{1-3}$-alkyl-O—,
wherein a —CH₂— member within a $C_{4-6}$-cycloalkyl- group or sub-group within the groups mentioned optionally is replaced by —$NR^N$—, —O—, or —S(O₂)—, or
wherein a >CH—CH₂— member within a $C_{5-6}$-cycloalkyl- group or sub-group within the groups mentioned optionally is replaced by >N—S(O)₂—, and
wherein each alkyl and cycloalkyl group and each alkyl and cycloalkyl sub-group within the groups mentioned optionally is substituted with HO—, HO—$C_{1-3}$-alkyl-, $C_{1-3}$-alkyl-oxy, $C_{1-3}$-alkyl-sulfonyl, or H₂N—C(O)—, and/or optionally substituted with 1 to 3 F atoms.

$R^{1a}$-G5b:

According to one embodiment the group $R^{1a}$ is selected from the group $R^{1a}$-G5b consisting of
a phenyl ring, a tetrazolyl ring,
a 5-membered heteroaromatic ring containing 1 —NH— or —O— group and additionally 1 or 2 =N— atoms,
wherein the rings are optionally substituted with one group selected from $R^{1b}$; and
wherein the H-atom in one or more NH groups present in the tetrazolyl ring or 5-membered heteroaromatic ring is replaced by $R^M$.

$R^{1b}$-G1:

The group $R^{1b}$ is preferably selected from the group $R^{1b}$-G1 as defined hereinbefore.

$R^{1b}$-G2:

According to one embodiment the group $R^{1b}$ is selected from the group $R^{1b}$-G2 consisting of F, Cl, CN, —OH, $C_{1-3}$-alkyl, $C_{3-6}$-cycloalkyl-, HO—$C_{1-3}$-alkyl, $C_{1-3}$-alkyl-O—, and $C_{3-6}$-cycloalkyl-O—,
wherein any alkyl and cycloalkyl group or sub-group within the groups mentioned is optionally substituted with 1 to 3 F atoms.

$R^{1b}$-G3:

According to one embodiment the group $R^{1b}$ is selected from the group $R^{1b}$-G3 consisting of F, Cl, CN, $C_{1-3}$-alkyl, $C_{3-6}$-cycloalkyl-, $C_{1-4}$-alkyl-O—, and $C_{3-6}$-cycloalkyl-O—,
wherein any alkyl and cycloalkyl group or sub-group within the groups mentioned is optionally substituted with 1 to 3 F atoms.

$R^{1b}$-G4:

According to one embodiment the group $R^{1b}$ is selected from the group $R^{1b}$-G4 consisting of F, Cl, and $C_{1-3}$-alkyl,
wherein the $C_{1-3}$-alkyl group is optionally substituted with 1 to 3 F atoms.

$R^{1b}$-G5:

According to one embodiment the group $R^{1b}$ is selected from the group $R^{1b}$-G5 consisting $C_{1-3}$-alkyl, preferably H₃C—.

$R^N$-G1:

The group $R^N$ is preferably selected from the group $R^N$-G1 as defined hereinbefore.

$R^N$-G2:

According to one embodiment the group $R^N$ is selected from the group $R^N$-G2 consisting of
H, $C_{1-4}$-alkyl, HO—$C_{1-4}$-alkyl (with the proviso that at least 2 carbon atoms are between the HO-group and an NH), $C_{1-4}$-alkyl-C(O)—, $C_{1-3}$-alkyl-O—C(O)—, and $C_{1-3}$-alkyl-S(O)₂—;
wherein any alkyl group or sub-group within the groups mentioned is optionally substituted with 1 to 3 F atoms.

$R^N$-G3:

According to one embodiment the group $R^N$ is selected from the group $R^N$-G3 consisting of
H, $C_{1-4}$-alkyl, HO—$C_{2-4}$-alkyl (with the proviso that at least 2 carbon atoms are between the HO-group and an NH) and $C_{1-3}$-alkyl-S(O)₂—;
wherein any alkyl group or sub-group within the groups mentioned is optionally substituted with 1 to 3 F atoms.

$R^M$-G1:

The group $R^M$ is preferably selected from the group $R^M$-G1 as defined hereinbefore.

$R^M$-G2:

According to one embodiment the group $R^M$ is selected from the group $R^M$-G2 consisting of
H, $C_{1-3}$-alkyl, HO—$C_{2-4}$-alkyl (with the proviso that at least 2 carbon atoms are between the HO-group and an NH), and $C_{1-3}$-alkyl-O—$C_{2-3}$-alkyl- (with the proviso that at least 2 carbon atoms are between an O-group and an NH);
wherein any alkyl group or sub-group within the groups mentioned is optionally substituted with 1 to 5 F atoms.

$R^M$-G3:

According to one embodiment the group $R^M$ is selected from the group $R^M$-G3 consisting of
H, —CH₃, HO—$C_{2-4}$-alkyl (with the proviso that at least 2 carbon atoms are between the HO-group and an NH), and H₃C—O—CH₂—CH₂—;
wherein any alkyl group or sub-group within the groups mentioned is optionally substituted with 1 to 3 F atoms.

$R^M$-G4:

According to one embodiment the group $R^M$ is selected from the group $R^M$-G4 consisting of
H, —CH₃, HO—$C_{2-4}$-alkyl (with the proviso that at least 2 carbon atoms are between the HO-group and an NH);
wherein any alkyl group or sub-group within the groups mentioned is optionally substituted with 1 to 3 F atoms.

Preferably m is an integer selected from 1 and 2.

Preferably n is an integer selected from 0 and 1, but most preferred n is 0.

The following preferred embodiments of compounds of the formula I are described using generic formula I.1 and I.2, wherein any tautomers, solvates, hydrates and salts thereof, in particular the pharmaceutically acceptable salts thereof, are encompassed.

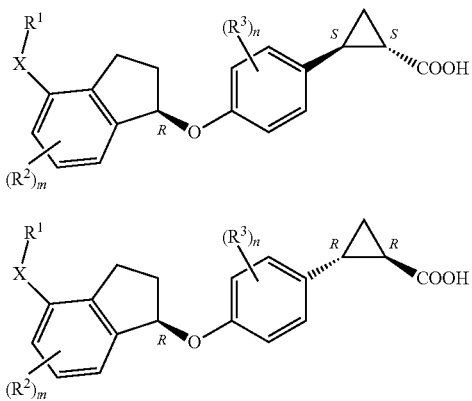

Examples of preferred subgeneric embodiments (E) according to the present invention are set forth in the following table 1, wherein each substituent group of each embodiment is defined according to the definitions set forth hereinbefore and wherein all other substituents of the formulas I, I.1 and I.2 are defined according to the definitions set forth hereinbefore. For example, the entry -G1 in the column under $R^1$- and the line of E1 means that in embodiment E1 substituent $R^1$ is selected from the definition designated $R^1$-G1. The same applies analogously to the other variables incorporated in the general formulas.

TABLE 1

| E | $R^1$— | $R^2$— | $R^3$— | $R^{1a}$— | $R^{1b}$— | $R^N$— | $R^M$— | m | n | X— |
|---|---|---|---|---|---|---|---|---|---|---|
| E1 | -G1 | -G1 | -G1 | -G1 | -G1 | -G1 | -G1 | 0-2 | 0-2 | -G1 |
| E2 | -G1 | -G1 | -G2 | -G2a | -G2 | -G1 | -G1 | 0-2 | 0-2 | -G2 |
| E3 | -G1 | -G1 | -G2 | -G2b | -G2 | -G1 | -G1 | 0-2 | 0-2 | -G2 |
| E4 | -G2 | -G1 | -G1 | -G1 | -G1 | -G1 | -G1 | 0-2 | 0-2 | -G1 |
| E5 | -G2 | -G1 | -G2 | -G2a | -G2 | -G1 | -G1 | 0-2 | 0-2 | -G2 |
| E6 | -G2 | -G1 | -G2 | -G2b | -G2 | -G1 | -G1 | 0-2 | 0-2 | -G2 |
| E7 | -G2 | -G2 | -G2 | -G2a | -G2 | -G1 | -G1 | 1, 2 | 0, 1 | -G2 |
| E8 | -G2 | -G2 | -G2 | -G2b | -G2 | -G1 | -G1 | 1, 2 | 0, 1 | -G2 |
| E9 | -G2 | -G2 | -G2 | -G2a | -G2 | -G1 | -G1 | 1 | 0 | -G2 |
| E10 | -G2 | -G2 | -G2 | -G2b | -G2 | -G1 | -G1 | 1 | 0 | -G2 |
| E11 | -G2 | -G2 | -G2 | -G2a | -G2 | -G1 | -G1 | 2 | 0 | -G2 |
| E12 | -G2 | -G2 | -G2 | -G2b | -G2 | -G1 | -G1 | 2 | 0 | -G2 |
| E13 | -G3 | -G2 | -G2 | -G3a | -G3 | -G2 | -G2 | 1, 2 | 0, 1 | -G2 |
| E14 | -G3 | -G2 | -G2 | -G3b | -G3 | -G2 | -G2 | 1, 2 | 0, 1 | -G2 |
| E15 | -G3 | -G2 | -G3 | -G3a | -G3 | -G2 | -G2 | 1 | 0 | -G2 |
| E16 | -G3 | -G2 | -G3 | -G3b | -G3 | -G2 | -G2 | 1 | 0 | -G2 |
| E17 | -G3 | -G2 | -G3 | -G3a | -G3 | -G2 | -G2 | 1 | 0 | -G3 |
| E18 | -G3 | -G2 | -G3 | -G3b | -G3 | -G2 | -G2 | 1 | 0 | -G3 |
| E19 | -G3 | -G2 | -G3 | -G3a | -G3 | -G2 | -G2 | 2 | 0 | -G3 |
| E20 | -G3 | -G2 | -G3 | -G3b | -G3 | -G2 | -G2 | 2 | 0 | -G3 |
| E21 | -G3 | -G2 | -G3 | -G3a | -G3 | -G2 | -G2 | 1 | 1 | -G3 |
| E22 | -G3 | -G2 | -G3 | -G3b | -G3 | -G2 | -G2 | 1 | 1 | -G3 |
| E23 | -G4 | -G3 | -G4 | -G4a | -G4 | -G2 | -G2 | 1, 2 | 0, 1 | -G3 |
| E24 | -G4 | -G3 | -G4 | -G4b | -G4 | -G2 | -G2 | 1, 2 | 0, 1 | -G3 |
| E25 | -G4a | -G3 | -G4 | -G4a | -G4 | -G2 | -G2 | 1, 2 | 0 | -G3 |
| E26 | -G4a | -G3 | -G4 | -G4b | -G4 | -G2 | -G2 | 1, 2 | 0 | -G3 |
| E27 | -G4b | -G3 | -G4 | -G4a | -G4 | -G2 | -G2 | 1, 2 | 0 | -G3 |
| E28 | -G4b | -G3 | -G4 | -G4b | -G4 | -G2 | -G2 | 1, 2 | 0 | -G3 |
| E29 | -G4 | -G3 | -G4 | -G4a | -G4 | -G3 | -G3 | 1, 2 | 0, 1 | -G3 |
| E30 | -G4 | -G3 | -G4 | -G4b | -G4 | -G3 | -G3 | 1, 2 | 0, 1 | -G3 |
| E31 | -G4a | -G3 | -G4 | -G4a | -G4 | -G3 | -G3 | 1 | 0 | -G3 |
| E32 | -G4a | -G3 | -G4 | -G4b | -G4 | -G3 | -G3 | 1 | 0 | -G3 |
| E33 | -G4b | -G3 | -G4 | -G4a | -G4 | -G3 | -G3 | 2 | 0 | -G3 |
| E34 | -G4b | -G3 | -G4 | -G4b | -G4 | -G3 | -G3 | 2 | 0 | -G3 |
| E35 | -G5 | -G3 | -G4 | -G4a | -G4 | -G3 | -G3 | 1 | 0 | -G3 |
| E36 | -G5 | -G3 | -G4 | -G4b | -G4 | -G3 | -G3 | 1 | 0 | -G3 |
| E37 | -G5 | -G3 | -G5 | -G4a | -G4 | -G3 | -G3 | 2 | 0 | -G3 |
| E38 | -G5 | -G3 | -G5 | -G4b | -G4 | -G3 | -G3 | 2 | 0 | -G3 |
| E39 | -G5 | -G3 | -G5 | -G5a | -G5 | -G3 | -G3 | 0, 1 | 0, 1 | -G4 |
| E40 | -G5 | -G3 | -G5 | -G5b | -G5 | -G3 | -G3 | 0, 1 | 0, 1 | -G4 |

TABLE 1-continued

| E | $R^1$— | $R^2$— | $R^3$— | $R^{1a}$— | $R^{1b}$— | $R^N$— | $R^M$— | m | n | X— |
|---|---|---|---|---|---|---|---|---|---|---|
| E41 | -G5 | -G3 | -G5 | -G5a | -G5 | -G3 | -G3 | 1 | 0 | -G4 |
| E42 | -G5 | -G3 | -G5 | -G5b | -G5 | -G3 | -G3 | 1 | 0 | -G4 |
| E43 | -G5 | -G3 | -G5 | -G5a | -G5 | -G3 | -G3 | 2 | 0 | -G4 |
| E44 | -G5 | -G3 | -G5 | -G5b | -G5 | -G3 | -G3 | 2 | 0 | -G4 |

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds according to the invention and their intermediates may be obtained using methods of synthesis which are known to the one skilled in the art and described in the literature of organic synthesis for example using methods described in "Comprehensive Organic Transformations, $2^{nd}$ edition", Richard C. Larock, Wiley-VCH, 2009, and "March's Advanced Organic Chemistry, $6^{th}$ edition", Michael B. Smith, Jerry March, Wiley Interscience, 2007. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man and described in the literature for example in "Protecting Groups, $3^{rd}$ Edition", Philip J. Kocienski, Theime, 2005 or "Greene's Protective Groups in Organic Synthesis, 4th Edition", Peter G. M. Wuts, Theadora W. Greene, John Wiley and Sons, 2007.

The compounds of the invention I are preferably accessed from a precursor II that bears the carboxylic acid function in a protected or masked form as sketched in Scheme 1; $R^1$, $R^2$, $R^3$, X, m, and n have the meanings as defined hereinbefore and hereinafter. Suited precursor groups for the carboxylic acid may be, e.g., a carboxylic ester, a carboxylic amide, cyano, an olefin, oxazole, or a thiazole. All these groups have been transformed into the carboxylic acid function by different means which are described in the organic chemistry literature and are known to the one skilled in the art. The preferred precursor group is a $C_{1-4}$-alkyl or benzyl carboxylate, each of which may be additionally mono- or polysubstituted with fluorine, methyl, and/or methoxy. These ester groups may be hydrolyzed with an acid, such as hydrochloric acid or sulfuric acid, or an alkali metal hydroxide, such as lithium hydroxide, sodium hydroxide, or potassium hydroxide, to yield the carboxylic acid function; the hydrolysis is preferably conducted in aqueous solvents, such as water and tetrahydrofuran, 1,4-dioxane, alcohol, e.g. methanol, ethanol, and isopropanol, or dimethyl sulfoxide, at 0 to 120° C. A tert-butyl ester is preferably cleaved under acidic conditions, e.g. trifluoroacetic acid or hydrochloric acid, in a solvent such as dichloromethane, 1,4-dioxane, isopropanol, or ethyl acetate. A benzyl ester is advantageously cleaved using hydrogen in the presence of a transition metal, preferably palladium on carbon. Benzyl esters bearing electron donating groups, such as methoxy groups, on the aromatic ring may also be removed under oxidative conditions; ceric ammonium nitrate (CAN) or 2,3-dichloro-5,6-dicyanoquinone (DDQ) are two commonly used reagents for this approach.

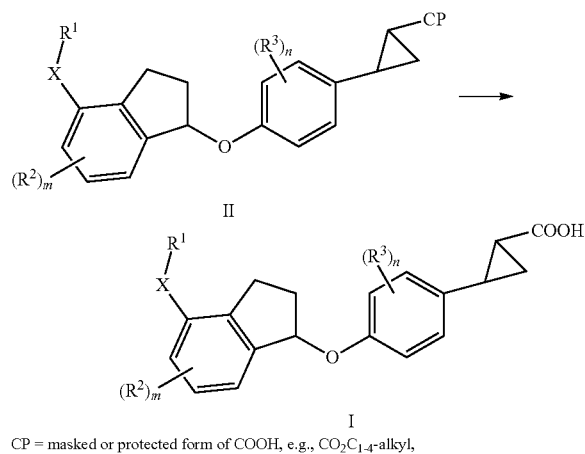

Scheme 1: Liberation of carboxylic acid function to access compounds of the invention CP = masked or protected form of COOH, e.g., $CO_2C_{1-4}$-alkyl, $CO_2CH_2$aryl, $CON(C_{1-4}$-alkyl$)_2$, CN, CH=$CH_2$, thiazol-2-yl, oxazol-2-yl Compound II, in turn, may be obtained from indane III, which bears a leaving group, and phenol IV, which is decorated with the carboxylic acid precursor group (Scheme 2); $R^1$, $R^2$, $R^3$, X, m, and n in Scheme 2 have the meanings as defined hereinbefore and hereinafter. The leaving group LG in III is replaced with the 0 in IV via a nucleophilic substitution; suited LG may be Cl, Br, I, methylsulfonyloxy, phenylsulfonyloxy, p-tolylsulfonyloxy, and trifluoromethylsulfonyloxy. The reaction is usually carried out in the presence of a base, such as triethylamine, ethyldiisopropylamine, 1,8-diazabicyclo[5.4.0]undecene, carbonates, e.g. $Li_2CO_3$, $Na_2CO_3$, $K_2CO_3$, and $Cs_2CO_3$, hydroxides, e.g. LiOH, NaOH, and KOH, alcoholates, e.g. NaOMe, NaOEt, and KOtBu, hydrides, e.g. NaH and KH, amides, e.g. $NaNH_2$, $KN(SiMe_3)_2$, and $LiN(iPr)_2$, and oxides, e.g. CaO and $Ag_2O$. Additives, such as silver salts, e.g. $AgNO_3$, $AgOSO_2CF_3$, and $Ag_2CO_3$, crown ethers, e.g. 12-crown-4, 15-crown-5, and 18-crown-6, hexamethylphosphorus triamide (HMPT), and 1,3-dimethyl-3,4,5,6-dihydro-2-pyrimidinone (DMPU), may be beneficial or even essential for the reaction to proceed. Preferred solvents are dimethylsulfoxide, N,N-dimethylformamide, N,N-dimethylacetamide, N-methylpyrrolidinone, acetonitrile, acetone, 1,4-dioxane, tetrahydrofuran, alcohol, e.g. ethanol or isopropanol, water, or mixtures thereof, while not all of the solvents can be combined with each additive and base mentioned above. Suited reaction temperatures range from –20 to 140° C.

Scheme 2: Preparation of precursor II

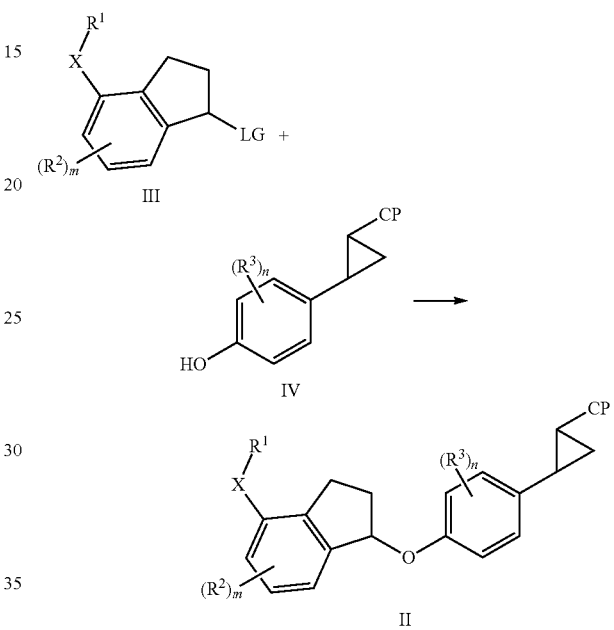

LG = leaving group, e.g., Cl, Br, I, $OSO_2Me$, $OSO_2Ph$, $OSO_2TOl$, $OSO_2CF_3$
CP = masked or protected form of COOH, e.g., $CO_2C_{1-4}$-alkyl, $CO_2CH_2$aryl, $CON(C_{1-4}$-alkyl$)_2$, CN, CH=$CH_2$, thiazol-2-yl, oxazol-2-yl An alternative reaction to combine building blocks III and IV is the Mitsunobu reaction or variations thereof (Scheme 3); $R^1$, $R^2$, $R^3$, X, m, and n in Scheme 3 have the meanings as defined hereinbefore and hereinafter. The reaction is usually conducted with a phosphine and an azodicarboxylic ester or amide in tetrahydrofuran, 1,4-dioxane, diethyl ether, toluene, benzene, dichloromethane, or mixtures thereof, at –30 to 100° C. Phosphines often used are triphenylphosphine and tributylphosphine which are commonly combined with dimethyl azodicarboxylate, diethyl azodicarboxylate, diisopropyl azodicarboxylate, di-(4-chlorobenzyl) azodicarboxylate, dibenzyl azodicarboxylate, di-tert-butyl azodicarboxylate, azodicarboxylic acid bis-(dimethylamide), azodicarboxylic acid dipiperidide, or azodicarboxylic acid dimorpholide.

Scheme 3: Mitsunobu reaction to access precursor II

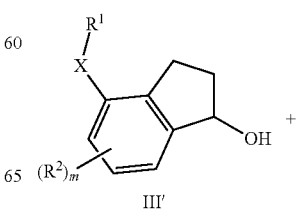

-continued

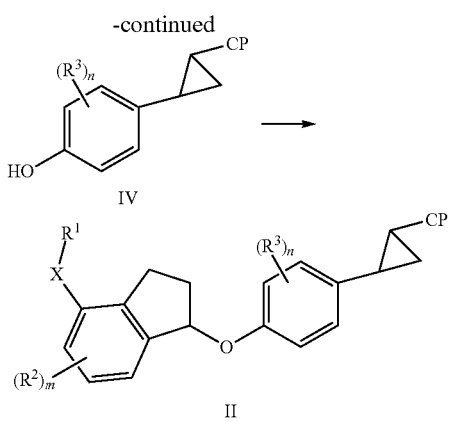

CP = masked or protected form of COOH, e.g., CO$_2$C$_{1-4}$-alkyl, CO$_2$CH$_2$aryl, CON(C$_{1-4}$-alkyl)$_2$, CN, CH═CH$_2$, thiazol-2-yl, oxazol-2-yl Intermediate III' is conveniently obtained from indanone V which, in turn, may be prepared from phenylpropionic acid derivative VI (Scheme 4); R$^1$, R$^2$, and m in Scheme 4 have the meanings as defined hereinbefore and hereinafter. For the intramolecular acylation (Friedel-Crafts acylation), VI→V, a considerable number of approaches has been reported. The reaction may be performed starting with a carboxylic acid, carboxylic ester, carboxylic anhydride, carboxylic chloride or fluoride, or a nitrile using a Lewis acid as catalyst. The following Lewis acids are some of the more often used ones: hydrobromic acid, hydroiodic acid, hydrochloric acid, sulfuric acid, phosphoric acid, P$_4$O$_{10}$, trifluoroacetic acid, methanesulfonic acid, toluenesulfonic acid, trifluoromethanesulfonic acid, ClSO$_3$H, Sc(OSO$_2$CF$_3$)$_3$, Tb(OSO$_2$CF$_3$)$_3$, SnCl$_4$, FeCl$_3$, AlBr$_3$, AlCl$_3$, SbCl$_5$, BCl$_3$, BF$_3$, ZnCl$_2$, montmorillonites, POCl$_3$, and PCl$_5$. The reaction may be conducted, e.g., in dichloromethane, 1,2-dichloroethane, nitrobenzene, chlorobenzene, carbon disulfide, mixtures thereof, or without an additional solvent in an excess of the Lewis acid, at 0 to 180° C. Carboxylic acids are preferably reacted in polyphosphoric acid at 0 to 120° C., while carboxylic chlorides are preferably reacted with AlCl$_3$ in dichloromethane or 1,2-dichloroethane at 0 to 80° C. The subsequent reduction of the keto group in Scheme 4 is a standard transformation in organic synthesis, which may be accomplished with lithium borohydride, sodium borohydride, lithium aluminum hydride, or diisobutylaluminum hydride. While sodium borohydride is employed in aqueous or alcoholic solution at 0 to 60° C., the other reducing agents mentioned are preferably used in inert solvents, such as tetrahydrofuran, diethyl ether, dichloromethane, and toluene, at −80 to 60° C. The reduction of the keto group may also be conducted in a stereoselective fashion providing the alcohol in enantiomerically enriched or pure form. Suited chiral reducing agents are boranes combined with an enantiomerically pure [1,3,2]oxazaborol (Corey-Bakshi-Shibata reaction or Corey-Itsuno reaction) or formic acid, formates, hydrogen, or silanes in the presence of an enantiomerically pure transition metal catalyst. Typical reaction conditions for the former approach are borane (complexed with, e.g., dimethyl sulfide) and (R)- or (S)-3,3-diphenyl-1-methyltetrahydro-1H,3H-pyrrolo[1,2-c][1,3,2]oxazaborol in, e.g., dichloromethane, toluene, methanol, tetrahydrofuran, or mixtures thereof, at 0 to 60° C. Using a chiral transition metal catalyst, such as a ruthenium complex, e.g. chloro{[(1S,2S)-(−)-2-amino-1,2-diphenylethyl](4-toluenesulfonyl)-amido}-(mesitylene)ruthenium(II), may deliver the hydroxy compound with high enantiomeric excess using, e.g., formic acid in the presence of a base, e.g. triethylamine, in dichloromethane, at −20 to 60° C.

Scheme 4: Preparation of intermediate III'

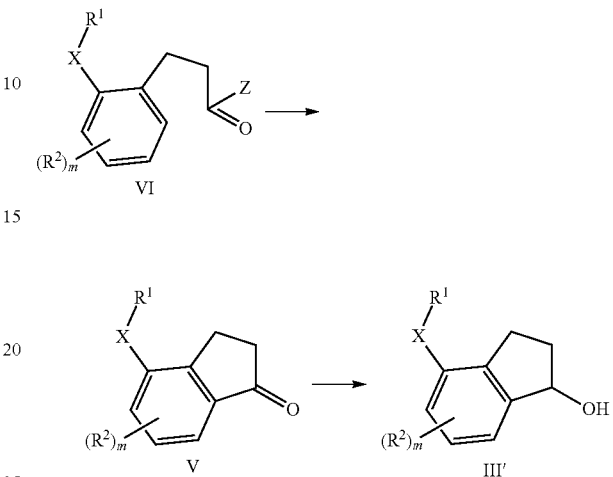

Z = e.g. OH, Cl

Alternatively, indanone V can be synthesized as described in Scheme 5; R$^1$, R$^2$, X, and m have the meanings as defined hereinbefore and hereinafter. Starting with benzene VII and 3-halo-propionic acid or a derivative thereof or acrylic acid or a derivative thereof the required indanone V may be obtained via the combination of a Friedel-Crafts alkylation and acylation reaction in one pot or two separate reactions (eq. 1.)). These reactions are catalyzed by a Lewis acid, such as triflic acid, sulfuric acid, phosphoric acid, AlCl$_3$, ZnCl$_2$, and phosphorus pentoxide, and preferably conducted without additional solvent in an excess of the Lewis acid or in dichloromethane, 1,2-dichloroethane, cyclohexane, or carbon disulfide, at 0 to 140° C. A preferred combination comprises compound VI, 3-chloro-propionyl chloride, and AlCl$_3$ in dichloromethane or 1,2-dichlorethane at 20 to 80° C.

Starting with ethynylbenzene VIII indanone V is accessible by a transition metal catalyzed reaction with carbon monoxide (eq. 2.)). Rhodium is a preferred catalyst basis which is combined with a phosphine, e.g. triphenylphosphine, and a base, e.g. triethylamine, and used in a solvent, preferably tetrahydrofuran, at high carbon monoxide pressure, preferably 50 to 150 bar, at 150 to 200° C. (see e.g. J. Org. Chem. 1993, 58, 5386-92).

Combination of 2-halo or pseudo-halo substituted styrene IX and carbon monoxide in the presence of a transition metal also allows the preparation of indanone V (eq. 3.)). Palladium catalysts are preferred and used with carbon monoxide or molybdenum hexacarbonyl as carbon monoxide source. Preferred solvents are N,N-dimethylformamide, N,N-dimethylacetamide, N-methylpyrrolidone, and 1,4-dioxane which are preferably employed at 20 to 150° C. by conventional heating or microwave irradiation. Pyridine and tetrabutylammonium chloride are preferred additives for this transformation (see e.g. J. Am. Chem. Soc. 2003, 125, 4804-7 and J. Org. Chem. 2005, 70, 346-9).

Scheme 5: Preparation of intermediate V

1.)

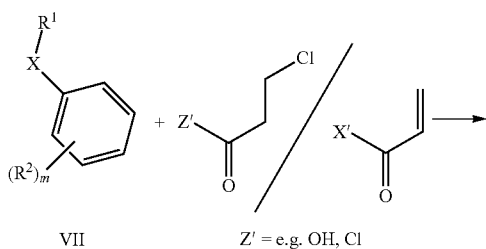

2.)

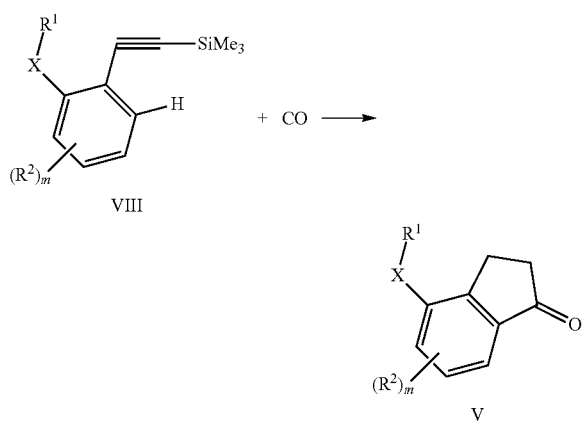

3.)

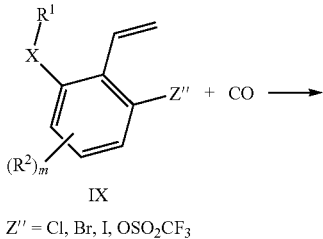

Z'' = Cl, Br, I, OSO$_2$CF$_3$

Compounds of general structure IV wherein R$^3$ and n have the meanings as defined hereinbefore and hereinafter and CP is a suitable carboxylic acid ester group can be synthesized as summarized in Scheme 6. Substituted cinnamic acid ester X in which one substituent is a 4-oxy group protected with a suitable protecting group is reacted with a methylene synthetic equivalent to give cyclopropyl ester XI. Suitable reagents for this transformation include diazomethane in the presence of a transition metal catalyst such as palladium diacetate (e.g. WO2011/94890), trimethyloxosulfonium halide in the presence of a base such as sodium hydride (e.g. WO2005/103032) and diiodomethane in the presence of copper and zinc (e.g. U.S. Pat. No. 628,476). Generally the use of a trans-cinnamic acid ester in these reactions leads to predominant formation of an trans-substituted cyclopropyl ester. Enantioselective reactions of this type can be performed using diazomethane and chiral copper complexes with moderate enantiomeric excesses (e.g. Charette et al.; Tet. Asymmetry, 2003, 14, 867-872). The protecting group is then removed under suitable conditions to give IV.

Alternatively: Substituted styrene XII in which one substituent is a 4-oxy group protected with a suitable protecting group is reacted with a diazoacetate ester XIII in the presence of a transition metal catalyst to give cyclopropyl ester XI. Suitable catalyst systems for this transformation include palladium diacetate (e.g. WO2007/104717), cobalt(II) porphyrins (e.g. WO2006/103503), rhodium complexes (e.g. WO2006/87169) and copper complexes (e.g. WO2010/51819) etc. Mixtures of cis and trans-cyclopropyl esters are generally formed with the trans-system generally predominant and the ratio depending on the catalyst system and substrates used. Enantioselective reactions of this type can be performed using chiral copper complexes with good to excellent enantiomeric excesses according to the method of Evans et al. (J. Am. Chem Soc., 1991, 113, 726-728) and variations thereof. The protecting group is then removed under suitable conditions to give IV.

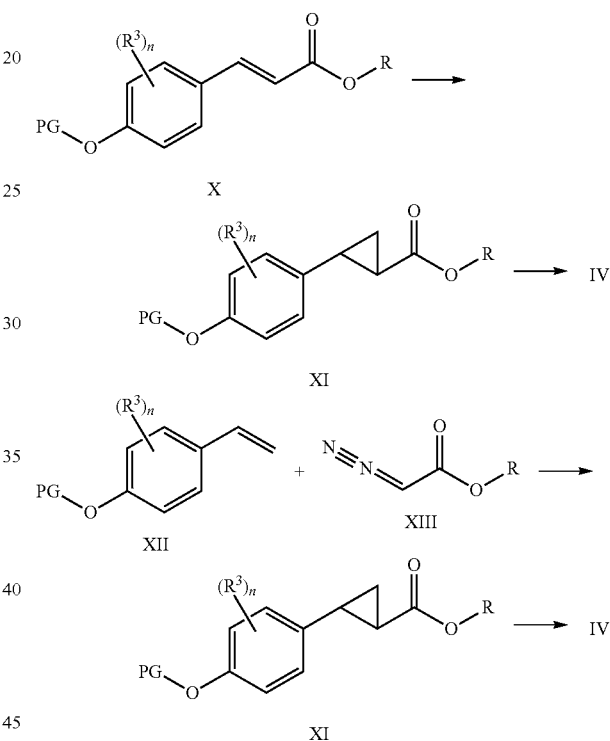

PG = protecting group, e.g., Me, Bn, tBu, tBuMe$_2$Si etc
R = ester protecting group of COOH, e.g., C1-4 alkyl, CH$_2$aryl For the stereoselective synthesis of compounds I of the invention with high enantiomeric excess intermediates XIVa, XIVb, and XVa, XVb are particularly useful and can be prepared as shown in Scheme 7. The reaction of 4-tert-butyloxystyrene with a diazo acetate ester, in the presence of a complex of copper triflate and (R,R)-2,2'-isopropylidenebis (4-tert-butyl-2-oxazoline) leads to the formation of intermediate XIVa. Preferably the diazoacetate ester is diazoethyl acetate, preferably the reaction is carried out at reduced temperature, suitably at or below 0° C., more preferably in the range of –10° C. to –20° C. as by this means the product is conveniently obtained in high enantiomeric excess. A suitable method for removing the tert-butyl protecting group is by treatment with trifluoroacetic acid, which leads to intermediate XVa with no loss of enantiomeric excess. The use of (S,S)-2,2'-isopropylidenebis(4-tert-butyl-2-oxazoline) leads to enantiomers XIVb and XVb.

Scheme 7: Stereoselective synthesis of intermediates XIVa, XIVb, and XVa, XVb
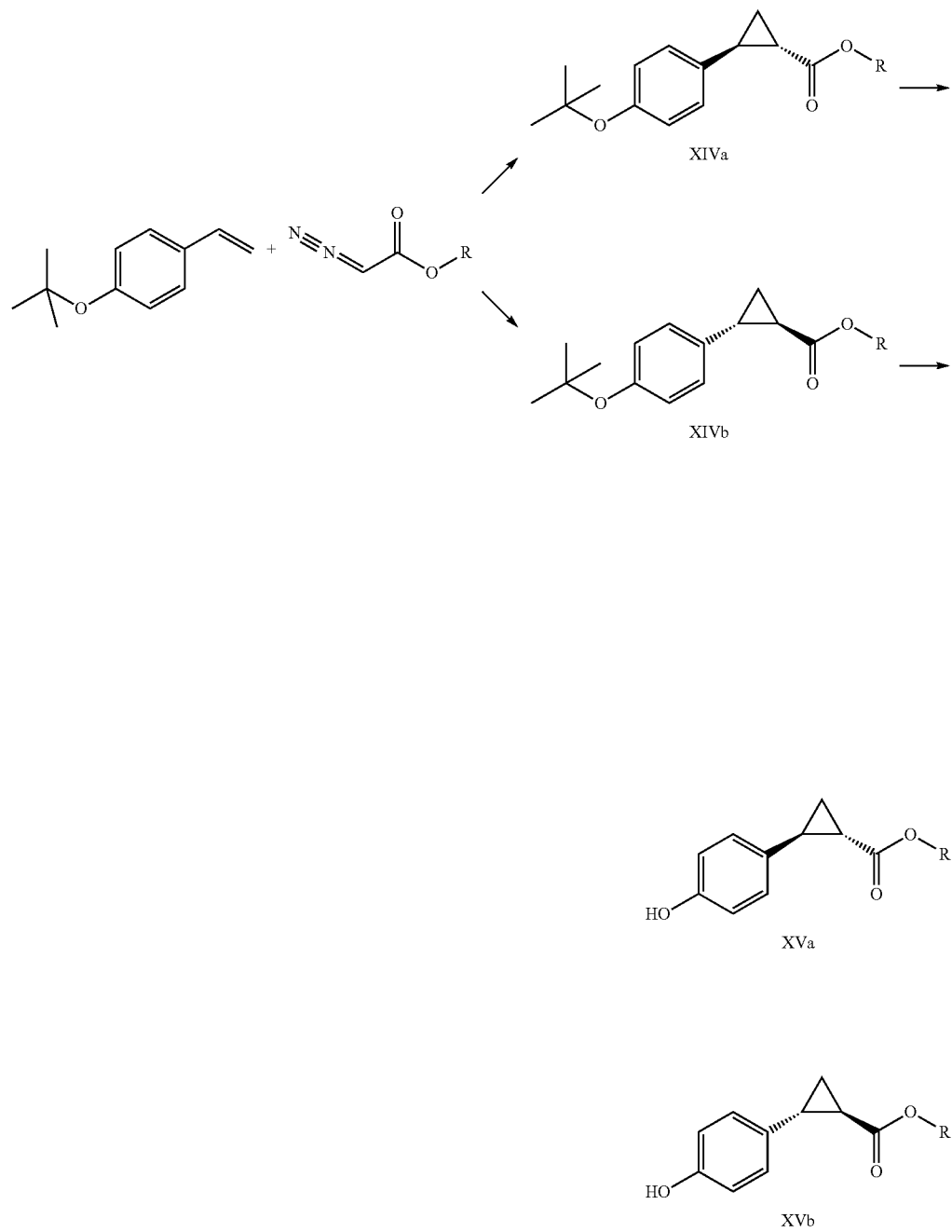
R = e.g. C1-C4 alkyl, CH₂Ph etc.
Note: Absolute stereochemistry assigned by analogy with Evans et al., J. Am. Chem Soc., 1991, 113, 726-728.

For compounds I of the invention in which X is an —O— group compounds of formula II can also be prepared as shown in Scheme 8. Intermediates of formula XVI, synthesized by the methods described above, or by oxidative cleavage of a corresponding boronic ester, are allowed to react with a suitable reagent e.g. an aryl or heteroaryl boronic acid, aryl or heteroaryl boronic ester, aryl or heteroaryl iodide etc. in a copper or palladium mediated cross coupling reaction (Chan-Lam, Buchwald-Hartwig, Ullman or related reaction) using methods described in the literature and known to those skilled in the art. Alternatively intermediates of formula XVI can be reacted with appropriate activated aryl or heteroaryl halide reagents or similar in the presence of a base according to methods described in the literature and known to those skilled in the art.

Scheme 8: Preparation of precursor II via ether formation

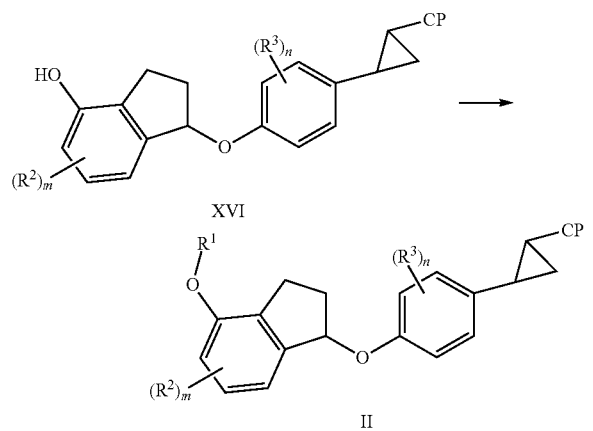

CP = masked or protected form of COOH, e.g., $CO_2C_{1-4}$-alkyl, $CO_2CH_2$aryl, $CON(C_{1-4}$-alkyl$)_2$, CN, CH═$CH_2$, thiazol-2-yl, oxazol-2-yl The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis for example in "Protecting Groups, 3$^{rd}$ Edition", Philip J. Kocienski, Theime, 2005 or "Greene's Protective Groups in Organic Synthesis, 4th Edition", Peter G. M. Wuts, Theadora W. Greene, John Wiley and Sons, 2007.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof. The compounds according to the invention are advantageously also obtainable using the methods described in the examples that follow, which may also be combined for this purpose with methods known to the skilled man from the literature.

TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed the condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing the risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the activation of the G-protein-coupled receptor GPR40 with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

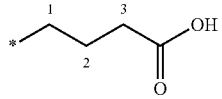

wherein the carboxy group is attached to the third carbon atom of the propyl group. The terms "1-methylpropyl-", "2,2-dimethylpropyl-" or "cyclopropylmethyl-" group represent the following groups:

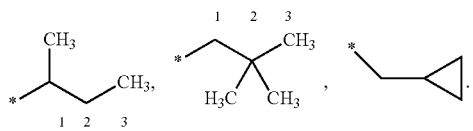

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers, et) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$—, and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_2CH_3))$—, —$(CHCH(CH_3)_2)$—, and —$C(CH_3)(CH_2CH_3)$—.

The term "$C_{2-n}$-alkenyl", is used for a group as defined in the definition for "$C_{1-n}$-alkyl" with at least two carbon atoms, if at least two of those carbon atoms of the group are bonded to each other by a double bond. For example the term $C_{2-3}$-alkenyl includes —$CH$=$CH_2$, —$CH$=$CH$—$CH_3$, —$CH_2$—$CH$=$CH_2$.

The term "$C_{2-n}$-alkynyl", is used for a group as defined in the definition for "$C_{1-n}$-alkyl" with at least two carbon atoms, if at least two of those carbon atoms of the group are bonded to each other by a triple bond. For example the term $C_{2-3}$-alkynyl includes —C≡CH, —C≡C—CH$_3$, —CH$_2$—C≡CH.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri-, or spiro-cyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

Many of the terms given above may be used repeatedly in the definition of a formula or group and in each case have one of the meanings given above, independently of one another.

Pharmacological Activity

The activity of the compounds of the invention may be demonstrated using the following assay: IP$_1$ accumulation measurements using the IPOne assay system—1321N1 cells stably expressing human GPR40 receptor (Euroscreen, Belgium) are seeded 24 h before the assay in black clear-bottom collagen-coated or white 384-well plates in culture medium containing 10% FCS, 1% Na-Pyruvate and 400 µg/mL G418. IP$_1$ is assayed according to the Manufacturer's description (Cisbio Bioassays, France). In brief, the assay is started by substitution of the culture medium by stimulation buffer (Hepes 10 mM, CaCl$_2$ 1 mM, MgCl$_2$ 0.5 mM, KCl 4.2 mM, NaCl 146 mM and glucose 5.5 mM, pH 7.4) without LiCl or with 50 nM LiCl. Cells are stimulated for 1 hour at 37° C., 5 or 10% CO$_2$ by addition of the compounds that are diluted in stimulation buffer containing LiCl yielding a final LiCl concentration of 50 mM. Assays are stopped by adding HTRF-conjugates (IP1-d2 and Anti-IP1 cryptate Tb) and lysis buffer, provided by the manufacturer. After an incubation time of 1 hour at room temperature plates are measured using an EnVision™, Perkin Elmer. The obtained fluorescence ratios at 665/615 nM are then used to calculate the pEC$_{50}$ values using GraphPad Prism 5 (Graphpad Software Inc, USA) or Assay Explorer 3.3 Software (Accelrys, Inc.) by interpolation using an IP$_1$ reference curve and subsequent sigmoidal curve fitting allowing for a variable hill slope.

The compounds according to the invention typically have EC$_{50}$ values in the range from about 1 nM to about 10 µM, preferably less than 1 µM, more preferably less than 100 nM.

EC$_{50}$ values for compounds according to the invention are shown in the following Table. The number of the compound corresponds to the number of the Example in the experimental section.

TABLE 2

| Example | EC$_{50}$ [nM] |
|---|---|
| 1 | 6 |
| 2 | 6 |
| 3 | 5 |
| 4 | 5 |
| 5 | 7 |
| 6 | 2 |
| 7 | 4 |
| 8 | 5 |
| 9 | 5 |
| 10 | 7 |
| 11 | 3 |
| 12 | 4 |

TABLE 2-continued

| Example | EC$_{50}$ [nM] |
|---|---|
| 13 | 8 |
| 14 | 3 |
| 15 | 8 |
| 16 | 92 |
| 17 | 9 |
| 18 | 6 |
| 19 | 48 |
| 20 | 11 |
| 21 | 3 |
| 22 | 27 |
| 23 | 12 |
| 24 | 2 |
| 25 | 2 |
| 26 | 19 |
| 27 | 2 |
| 28 | 1 |
| 29 | 3 |
| 30 | 8 |
| 31 | 9 |
| 32 | 4 |
| 33 | 5 |
| 34 | 16 |
| 35 | 3 |
| 36 | 2 |
| 37 | 2 |
| 38 | 27 |
| 39 | 6 |
| 40 | 45 |
| 41 | 12 |
| 42 | 4 |
| 43 | 37 |
| 44 | 197 |
| 45 | 2 |
| 46 | 8 |

In view of their ability to modulate the activity of the G-protein-coupled receptor GPR40, in particular an agonistic activity, the compounds of general formula I according to the invention, including the corresponding salts thereof, are theoretically suitable for the treatment of all those diseases or conditions which may be affected or which are mediated by the activation of the G-protein-coupled receptor GPR40.

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the G-protein-coupled receptor GPR40 in a patient, preferably in a human.

In yet another aspect the present invention relates to a method for treating a disease or condition mediated by the activation of the G-protein-coupled receptor GPR40 in a mammal that includes the step of administering to a patient, preferably a human, in need of such treatment a therapeutically effective amount of a compound or a pharmaceutical composition of the present invention.

Diseases and conditions mediated by agonists of the G-protein-coupled receptor GPR40 embrace metabolic diseases or conditions. According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macroangiopathies), metabolic acidosis or ketosis, reactive hypoglycemia, hyperinsulinemia, glucose metabolic disorder, insulin resistance, metabolic syndrome, dyslipidemias of different origins, atherosclerosis and related diseases, obesity, high blood pressure, chronic heart failure, edema, and hyperuricemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:
  for preventing, delaying, slowing the progression of or treating metabolic diseases, such as for example type 1 diabetes, type 2 diabetes, insufficient glucose tolerance, insulin resistance, hyperglycemia, hyperlipidemia, hypercholesterolemia, dyslipidemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);
  for improving glycemic control and/or reducing fasting plasma glucose, postprandial plasma glucose and/or the glycosylated hemoglobin HbA1c;
  for preventing, delaying, slowing or reversing the progression of disrupted glucose tolerance, insulin resistance and/or metabolic syndrome to type 2 diabetes;
  for preventing, delaying, slowing the progression of or treating a condition or a disease selected from among the complications of diabetes, such as for example retinopathy, nephropathy or neuropathies, diabetic foot, ulcers or macroangiopathies;
  for reducing weight or preventing weight gain or assisting weight loss;
  for preventing or treating the degradation of pancreatic beta cells and/or improving and/or restoring the functionality of pancreatic beta cells and/or restoring the functionality of pancreatic insulin secretion;
  for maintaining and/or improving insulin sensitivity and/or preventing or treating hyperinsulinemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers, and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers, and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure, and/or atherosclerosis.

Antidiabetic agents are for example metformin, sulphonylureas, nateglinide, repaglinide, thiazolidinediones, PPAR- (alpha, gamma or alpha/gamma) agonists or modulators, alpha-glucosidase inhibitors, DPP-IV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the G-protein-coupled receptor GPR40, in particular diseases or conditions as described hereinbefore and hereinafter.

In yet another aspect the present invention relates a method for treating a disease or condition mediated by the activation of the G-protein-coupled receptor GPR40 in a patient that includes the step of administering to the patient, preferably a human, in need of such treatment a therapeutically effective amount of a compound of the present invention in combination with a therapeutically effective amount of one or more additional therapeutic agents described hereinbefore and hereinafter.

The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

Pharmacological Activity

The activity of the compounds of the invention may be demonstrated using the following assay:

$IP_1$ accumulation measurements using the IPOne assay system—1321N1 cells stably expressing human GPR40 receptor (Euroscreen, Belgium) are seeded 24 h before the assay in black clear-bottom collagen-coated or white 384-well plates in culture medium containing 10% FCS, 1% Na-Pyruvate and 400 μg/mL G418. $IP_1$ is assayed according to the Manufacturer's description (Cisbio Bioassays, France). In brief, the assay is started by substitution of the culture medium by stimulation buffer (Hepes 10 mM, $CaCl_2$ 1 mM, $MgCl_2$ 0.5 mM, KCl 4.2 mM, NaCl 146 mM and glucose 5.5 mM, pH 7.4) without LiCl or with 50 nM LiCl. Cells are stimulated for 1 hour at 37° C., 5 or 10% $CO_2$ by addition of the compounds that are diluted in stimulation buffer containing LiCl yielding a final LiCl concentration of 50 mM. Assays are stopped by adding HTRF-conjugates (IP1-d2 and Anti-IP1 cryptate Tb) and lysis buffer, provided by the manufacturer. After an incubation time of 1 hour at room temperature plates are measured using an EnVision™, Perkin Elmer. The obtained fluorescence ratios at 665/615 nM are then used to calculate the $pEC_{50}$ values using GraphPad Prism 5 (Graphpad Software Inc, USA) or Assay Explorer 3.3 Software (Accelrys, Inc.) by interpolation using an $IP_1$ reference curve and subsequent sigmoidal curve fitting allowing for a variable hill slope.

The compounds according to the invention typically have $EC_{50}$ values in the range from about 1 nM to about 10 μM, preferably less than 1 μM, more preferably less than 100 nM. $EC_{50}$ values for compounds according to the invention are shown in the following Table. The number of the compound corresponds to the number of the Example in the experimental section.

TABLE 2

| Example | $EC_{50}$ [nM] |
|---|---|
| 1 | 6 |
| 2 | 6 |
| 3 | 5 |
| 4 | 5 |
| 5 | 7 |
| 6 | 2 |
| 7 | 4 |
| 8 | 5 |
| 9 | 5 |
| 10 | 7 |
| 11 | 3 |
| 12 | 4 |
| 13 | 8 |
| 14 | 3 |
| 15 | 8 |

TABLE 2-continued

| Example | EC$_{50}$ [nM] |
|---|---|
| 16 | 92 |
| 17 | 9 |
| 18 | 6 |
| 19 | 48 |
| 20 | 11 |
| 21 | 3 |
| 22 | 27 |
| 23 | 12 |
| 24 | 2 |
| 25 | 2 |
| 26 | 19 |
| 27 | 2 |
| 28 | 1 |
| 29 | 3 |
| 30 | 8 |
| 31 | 9 |
| 32 | 4 |
| 33 | 5 |
| 34 | 16 |
| 35 | 3 |
| 36 | 2 |
| 37 | 2 |
| 38 | 27 |
| 39 | 6 |
| 40 | 45 |
| 41 | 12 |
| 42 | 4 |
| 43 | 37 |
| 44 | 197 |
| 45 | 2 |
| 46 | 8 |

EXAMPLES/PRELIMINARY REMARKS

The terms "ambient temperature" and "room temperature" are used interchangeably and designate a temperature of about 20° C. As a rule, $^1$H-NMR and/or mass spectra have been obtained for the compounds prepared.

Analytical Methods $^1$H-NMR spectra were recorded at 25° C. on a Varian INOVA (500 MHz) spectrometer or a Varian (400 MHz) spectrometer.

GC (Method 1):
Instrument: GC/MS Thermo Scientific TRACE GC ULTRA, DSQ II MS single quadrupole
Column: Agilent DB-5MS, 25 m×0.25 mm×0.25 um
Carrier gas: Helium, 1 mL/min constant flow
Oven Program: 50° C., to 100° C. in 10° C./min, to 200° C. in 20° C./min, to 320° C. in 30° C./min (hold 10 min).
Detection: DSQ II MS single quadrupole
  Ion source: EI
  Scan range: 50-450 amu LC (Method 2):
Instrument: LC/MS ThermoFinnigan HPLC Surveyor DAD, MSQ single quadrupole
Column: Synergi Hydro RP100A, 2.5 μm, 3×50 mm
Mobile phase: A=H$_2$O 90%+10% CH$_3$CN+NH$_4$COOH 10 mM
B=CH$_3$CN 90%+H$_2$O 10%+NH$_4$COOH 10 mM

| Time in min: | % A | % B | Flow rate in mL/min |
|---|---|---|---|
| 0.00 | 100 | 0 | 0.7 |
| 1 | 100 | 0 | 0.7 |
| 8.00 | 0 | 100 | 0.7 |
| 10.0 | 0 | 100 | 0.7 |
| 11.0 | 100 | 0 | 0.7 |
| 12.0 | 100 | 0 | 0.7 |

Detection: UV 254 nm
Detection: Finnigan MSQ, single quadrupole
Ion source: APCI+/APCI−
Scan range: 100-900 amu LC (Method 3):
Instrument: LC/MS ThermoFinnigan HPLC Surveyor DAD, LCQFleet Ion Trap
Column: Xselect CSH, 2.5 μm, 4.6×50 mm
Mobile phase: A=H$_2$O 90%+10% CH$_3$CN+HCOOH 0.1%
B=CH$_3$CN 90%+H$_2$O 10%+HCOOH 0.1%

| Time in min: | % A | % B | Flow rate in mL/min |
|---|---|---|---|
| 0.00 | 100 | 0 | 1.4 |
| 1 | 100 | 0 | 1.4 |
| 8.50 | 0 | 100 | 1.4 |
| 10.0 | 0 | 100 | 1.4 |
| 10.2 | 100 | 0 | 1.4 |
| 11.0 | 100 | 0 | 1.4 |

Detection: UV 254 nm
Detection: Finnigan Fleet, Ion Trap
Ion source: ES$^+$
Scan range: 100-900 amu Lc (Method 4):
Instrument: LC/MS Waters Acquity UPLC System DAD, SQD single quadrupole
Column: HSS C18 1.8 μm 2.1×50 mm, Temp 35° C.
Mobile phase: A=H$_2$O 90%+CH$_3$CN 10%+CF$_3$COOH 0.1%
B=CH$_3$CN 90%+H$_2$O 10%

| Time in min: | % A | % B | Flow rate in mL/min |
|---|---|---|---|
| 0.00 | 100 | 0 | 0.7 |
| 1.20 | 0 | 100 | 0.7 |
| 1.45 | 0 | 100 | 0.7 |
| 1.55 | 100 | 0 | 0.7 |
| 1.75 | 100 | 0 | 0.7 |

Detection: UV 254 nm
Detection: SQD, single quadrupole
Ion source: ES$^+$/ES$^-$
Scan range: 90-900 amu LC (Method 5):
Instrument: LC/MS Waters Acquity UPLC System DAD, SQD single quadrupole
Column: BEH C18 1.7 μm 2.1×50 mm, Temp 35° C.
Mobile phase: A=H$_2$O 90%+CH$_3$CN 10%+NH$_4$COOH 5 mM
B=CH$_3$CN 90%+H$_2$O 10%

| Time in min: | % A | % B | Flow rate in mL/min |
|---|---|---|---|
| 0.00 | 100 | 0 | 0.7 |
| 1.20 | 0 | 100 | 0.7 |
| 1.45 | 0 | 100 | 0.7 |
| 1.55 | 100 | 0 | 0.7 |
| 1.75 | 100 | 0 | 0.7 |

Detection: UV 254 nm
Detection: SQD, single quadrupole
Ion source: ES+/ES−
Scan range: 90-900 amu
LC (Method 6):
Instrument: LC/MS Waters Acquity UPLC System DAD, SQD single quadrupole
Column: HSS C18 1.8 µm 2.1×50 mm, Temp 35° C.
Mobile phase: A=$H_2O$ 90%+$CH_3CN$ 10%+$CF_3COOH$ 0.1%
  B=$CH_3CN$ 90%+$H_2O$ 10%

| Time in min: | % A | % B | Flow rate in mL/min |
| --- | --- | --- | --- |
| 0.00 | 100 | 0 | 0.7 |
| 0.70 | 0 | 100 | 0.7 |
| 2.30 | 0 | 100 | 0.7 |
| 2.40 | 100 | 0 | 0.7 |
| 2.60 | 100 | 0 | 0.7 |

Detection: UV 254 nm
Detection: SQD, single quadrupole
Ion source: ES+/ES−
Scan range: 90-900 amu
LC (Method 7):
Instrument: LC/MS Waters Alliance 2695 HPLC System DAD, Quattro Micro Triple quadrupole
Column: Gemini C18 3 µm 4.6×50 mm, Temp 35° C.
Mobile phase: A=$H_2O$ 90%+$CH_3CN$ 10%+$CF_3COOH$ 0.1%
  B=$CH_3CN$

| Time in min: | % A | % B | Flow rate in mL/min |
| --- | --- | --- | --- |
| 0.00 | 50 | 50 | 1.3 |
| 3.5 | 10 | 90 | 1.3 |
| 4.5 | 10 | 90 | 1.3 |
| 4.6 | 50 | 50 | 1.3 |

Detection: UV 254 nm
Detection: Quattro Micro, triple quadrupole
Ion source: ES+
Scan range: 120-900 amu
LC (Method 8):
Instrument: LC/MS Waters Alliance 2695 HPLC System DAD, Quattro Micro Triple quadrupole
Column: Atlantis dC18 5 µm 4.6×50 mm, Temp 35° C.
Mobile phase: A=$H_2O$ 90%+10% $CH_3CN$+$CF_3COOH$ 0.05%
  B=$CH_3CN$ 90%+10% $H_2O$

| Time in min: | % A | % B | Flow rate in mL/min |
| --- | --- | --- | --- |
| 0.00 | 100 | 0 | 1.3 |
| 0.70 | 100 | 0 | 1.3 |
| 4.50 | 0 | 100 | 1.3 |
| 5.80 | 0 | 100 | 1.3 |
| 6.00 | 100 | 0 | 1.3 |

Detection: UV 254 nm
Detection: Quattro Micro, triple quadrupole
Ion source: ES+
Scan range: 90-1000 amu
LC (Method 9):
Instrument: LC/MS Waters Alliance 2695 HPLC System DAD, Quattro Micro Triple quadrupole
Column: XBridge Phenyl 3.5 µm 3×30 mm, Temp 35° C.
Mobile phase: A=$H_2O$ 90%+10% $CH_3CN$+$NH_4HCO_3$ 5 mM
  B=$CH_3CN$ 90%+10% $H_2O$

| Time in min: | % A | % B | Flow rate in mL/min |
| --- | --- | --- | --- |
| 0.00 | 100 | 0 | 1.3 |
| 4.50 | 0 | 100 | 1.3 |
| 5.80 | 0 | 100 | 1.3 |
| 6.00 | 100 | 0 | 1.3 |

Detection: UV 254 nm
Detection: Quattro Micro, triple quadrupole
Ion source: ES+
Scan range: 90-1000 amu
LC (Method 10):
Instrument: LC/MS ThermoFinnigan HPLC Surveyor DAD, LCQFleet Ion Trap
Column: Symmetry Shield RP8, 5 µm, 4.5×150 mm
Mobile phase: A=$H_2O$ 90%+10% $CH_3CN$+HCOOH 0.1%
  B=$CH_3CN$ 90%+$H_2O$ 10%+HCOOH 0.1%

| Time in min: | % A | % B | Flow rate in mL/min |
| --- | --- | --- | --- |
| 0.00 | 95 | 5 | 1 |
| 1.5 | 95 | 5 | 1 |
| 11.05 | 5 | 95 | 1 |
| 13.0 | 5 | 95 | 1 |
| 13.03 | 95 | 5 | 1 |
| 15.0 | 95 | 5 | 1 |

Detection: UV 254 nm
Detection: Finnigan Fleet, Ion Trap
Ion source: ES+
Scan range: 100-900 amu
LC (Method 11):
Instrument: LC/MS ThermoFinnigan HPLC Surveyor DAD, LCQFleet Ion Trap
Column: Symmetry Shield RP8, 5 µm, 4.5×150 mm
Mobile phase: A=$H_2O$ 90%+10% $CH_3CN$+HCOOH 0.1%
  B=$CH_3CN$ 90%+$H_2O$ 10%+HCOOH 0.1%

| Time in min: | % A | % B | Flow rate in mL/min |
| --- | --- | --- | --- |
| 0.00 | 70 | 30 | 0.85 |
| 1 | 50 | 50 | 0.85 |
| 8.50 | 0 | 100 | 0.85 |
| 10.0 | 0 | 100 | 0.85 |
| 10.2 | 70 | 30 | 0.85 |
| 11.0 | 70 | 30 | 0.85 |

Detection: UV 254 nm
Detection: Finnigan Fleet, Ion Trap
Ion source: ES+
Scan range: 100-900 amu
LC (Method 12):
Instrument: LC/MS ThermoFinnigan HPLC Surveyor DAD, MSQ single quadrupole
Column: Synergi Hydro RP100A, 2.5 µm, 3×50 mm
Mobile phase: A=$H_2O$ 90%+$CH_3CN$ 10%+$NH_4COOH$ 5 mM
  B=$CH_3CN$ 90%+$H_2O$ 10%

| Time in min: | % A | % B | Flow rate in mL/min |
| --- | --- | --- | --- |
| 0.00 | 100 | 0 | 1.2 |
| 4.00 | 0 | 100 | 1.2 |
| 5.30 | 0 | 100 | 1.2 |
| 5.50 | 100 | 0 | 1.2 |
| 6.00 | 100 | 0 | 1.2 |

Detection: UV 254 nm
Detection: Finnigan MSQ, single quadrupole
Ion source: APCI⁺/APCI⁻
Scan range: 100-900 amu
LC (Method 13):
Instrument: LC/MS ThermoFinnigan HPLC Surveyor DAD, MSQ single quadrupole
Column: Synergi Hydro RP100A, 2.5 µm, 3×50 mm
Mobile phase: A=$H_2O$ 90%+$CH_3CN$ 10%+$NH_4COOH$ 5 mM
B=$CH_3CN$ 90%+$H_2O$ 10%

| Time in min: | % A | % B | Flow rate in mL/min |
| --- | --- | --- | --- |
| 0.00 | 100 | 0 | 1.2 |
| 1.50 | 100 | 0 | 1.2 |
| 9.00 | 0 | 100 | 1.2 |
| 10.50 | 0 | 100 | 1.2 |
| 11.00 | 100 | 0 | 1.2 |
| 12.00 | 100 | 0 | 1.2 |

Detection: UV 254 nm
Detection: Finnigan MSQ, single quadrupole
Ion source: APCI⁺/APCI⁻
Scan range: 100-900 amu
LC (Method 14):
Instrument: LC/MS Waters Alliance 2695 HPLC System DAD, Quattro Micro Triple quadrupole
Column: Zorbax Eclipse Plus C18, 3.5 µm 4.6×50 mm, Temp 35° C.
Mobile phase: A=$H_2O$ 90%+$CH_3CN$ 10%+$NH_4COOH$ 5 mM
B=$CH_3CN$ 90%+$H_2O$ 10%

| Time in min: | % A | % B | Flow rate in mL/min |
| --- | --- | --- | --- |
| 0.00 | 50 | 50 | 1.3 |
| 3.50 | 5 | 95 | 1.3 |
| 4.50 | 5 | 95 | 1.3 |
| 4.60 | 50 | 50 | 1.3 |

Detection: UV 254 nm
Detection: Quattro Micro, triple quadrupole
Ion source: ES⁺
Scan range: 120-900 amu

SYNTHESIS OF INTERMEDIATES

Intermediate 1

(1S,2S)-2-(4-Hydroxy-phenyl)-cyclopropanecarboxylic acid ethyl ester

Note:
Absolute stereochemistry assigned by analogy with Evans et al., J. Am. Chem Soc., 1991, 113, 726-728.

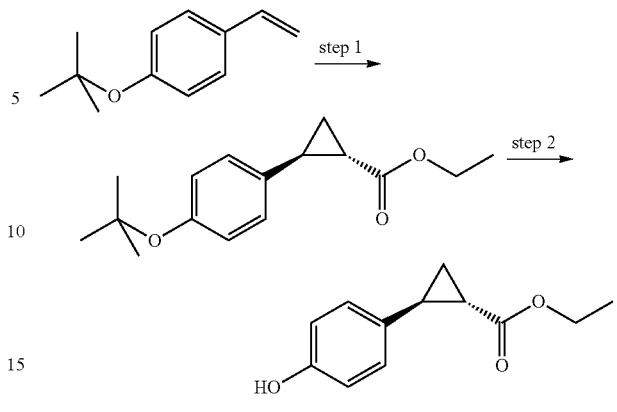

Step 1: (1S,2S)-2-(4-tert-Butoxy-phenyl)-cyclopropanecarboxylic acid ethyl ester In a one liter three necked flask equipped with a magnetic stirrer bar, an alcohol thermometer, nitrogen inlet and addition inlet sealed with a suba seal, (R,R)-2,2'-isopropylidenebis(4-tert-butyl-2-oxazoline) (417 mg, 1.42 mmol) and copper(I) trifluoromethanesulfonate benzene complex (714 mg, 1.42 mmol) are dissolved in degassed tert-butyl methyl ether (120 mL) and stirred for 15 minutes under $N_2$. 4-tert-Butoxystyrene (25 g, 142 mmol) is added and the mixture cooled to −10° C. (internal temperature) under $N_2$. Ethyldiazoacetate (24.75 g, 184.4 mmol) is dissolved in 50 mL of tert-butyl methyl ether and 5 mL of the resulting solution is added dropwise with cooling over 30 minutes using a syringe pump. The addition is then stopped and the mixture stirred at −10° C. until the reaction starts (effervescence and color change). Once the reaction has started the mixture is cooled to −20° C. and the remaining solution added dropwise using a syringe pump over 3 hours maintaining the temperature at −20° C. Once the addition is completed the mixture is allowed to slowly warm to room temperature and stirred overnight. NMR of a reaction sample shows approx. 30% of unreacted starting material, therefore the mixture is cooled to −20° C. and a further 14.1 g of ethyl diazoacetate in 30 mL of tert-butyl methyl ether is added dropwise over 90 minutes, stirred for 1 hour at −20° C. and then allowed to warm to room temperature. The solvent is removed under vacuum and the residue is purified by flash chromatography (0-5% ethyl acetate in cyclohexane) to give the title compound (yield 29.7 g). GC (METHOD 1): $t_R$=11.47 min; Mass spectrum (EI⁺): m/z=262 [M]⁺, e.e. 96% by chiral HPLC (Column: Daicel Chiralcel OJ-H, 4.6×250 mm, 5 µm Mobile phase: hexane:ethanol 95:5, 1 mL/min, 25° C.) $t_R$=9.87 (9.13) min.

Step 2: (1S,2S)-2-(4-Hydroxy-phenyl)-cyclopropanecarboxylic acid ethyl ester (1S,2S)-2-(4-tert-Butoxy-phenyl)-cyclopropanecarboxylic acid ethyl ester (10.5 g, 35.6 mmol) is dissolved in trifluoroacetic acid (15 mL, 196 mmol) and stirred for 5 minutes. The mixture is concentrated under vacuum, then re-evaporated five times from dichloromethane. The residue is dissolved in boiling cyclohexane (20 mL) and then allowed to cool. The cyclohexane layer is decanted off and the operation repeated. The residue is dried under vacuum to give the title compound (yield 6.51 g). GC (METHOD 1): $t_R$=11.04 min; Mass spectrum (EI⁺): m/z=206 [M]+, e.e. 96% by chiral HPLC (Column: Daicel Chiralpak AS-H, 4.6×250 mm, 5 μm Mobile phase: hexane:ethanol 95:5, 1 mL/min, 25° C.) $t_R$=14.17 (13.11) min.

Intermediate 2

(S)-4-Bromo-7-fluoro-indan-1-ol

Note:

Absolute stereochemistry assigned by analogy with Noyori et al., J. Am. Chem. Soc., 1995, 117 (28), pp 7562-7563.

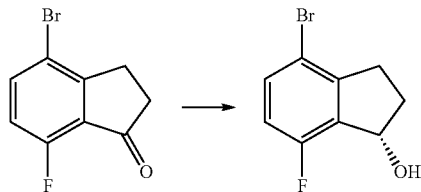 [SMILES: O=C1CCc2c(Br)ccc(F)c21 ; O[C@H]1CCc2c(Br)ccc(F)c21]

Triethylamine (26.2 mL, 187 mmol) is dissolved in dichloromethane (100 mL) and cooled to 0° C. then formic acid (7.96 mL, 211 mmol) is added dropwise with cooling. 4-Bromo-7-fluoro-indan-1-one (European patent EP2042480, 13.8 g, 60 mmol) is added and the mixture degassed with a flow of argon. Chloro([1S,2S)-(+2-amino-1,2-diphenylethyl](4-toluenesulfonyl)amido)(mesitylene)ruthenium(II) complex (375 mg, 0.6 mmol) is added and the mixture is stirred overnight at room temperature. Water is added, the mixture shaken and the phases separated. The organic phase is dried and concentrated under vacuum. The residue is purified by flash chromatography (0-20% ethyl acetate in cyclohexane) to give the title compound (Yield 13.1 g). GC (METHOD 1): $t_R$=9.35 min; Mass spectrum (EI$^+$): m/z=229, 231 [M]$^+$, e.e. 100% by chiral HPLC (Column: Daicel Chiralcel OJ-H, 4.6×250 mm, 5 μm Mobile phase: hexane:ethanol 95:5, 1 mL/min, 25° C.) $t_R$=9.87 min.

Intermediate 3

(1S,2S)-2-[4-((R)-4-Bromo-7-fluoro-indan-1-yloxy)-phenyl]-cyclopropanecarboxylic acid ethyl ester

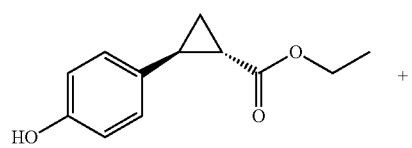

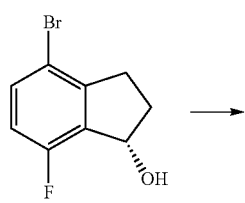

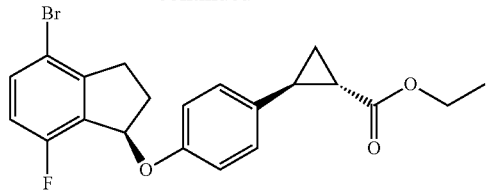

(1S,2S)-2-(4-Hydroxy-phenyl)-cyclopropanecarboxylic acid ethyl ester (Intermediate 1, 6.51 g, 31.6 mmol), (S)-4-bromo-7-fluoro-indan-1-ol (Intermediate 2, 7.29 g, 31.6 mmol) and triphenyl phosphine (9.11 g, 34.7 mmol) are dissolved in dry tetrahydrofuran (50 mL) and cooled to −20° C. under nitrogen atmosphere. Di-tert-butyl azodicarboxylate (8.00 g, 34.7 mmol) is added and the mixture stirred for 30 minutes at −20° C., then allowed to warm to room temperature and stirred overnight. The solvent is removed under vacuum and the residue purified by flash chromatography (0-10% ethyl acetate in cyclohexane) to give the title compound (Yield 8.23 g). LC (METHOD 2): $t_R$=8.72 min; Mass spectrum (ES$^+$): m/z=460 [M+H+MeCN]$^+$, e.e. 96% by chiral HPLC (Column: Daicel Chiralpak AS-H, 4.6×250 mm, 5 μm Mobile phase: hexane:ethanol 80:20, 1 mL/min, 25° C.) $t_R$=4.96 (4.63) min.

Intermediate 4

(1S,2S)-2-{4-[(R)-7-Fluoro-4-(4,4,5,5-tetramethyl-[1,3,2]dioxaborolan-2-yl)-indan-1-yloxy]-phenyl}-cyclopropanecarboxylic acid ethyl ester

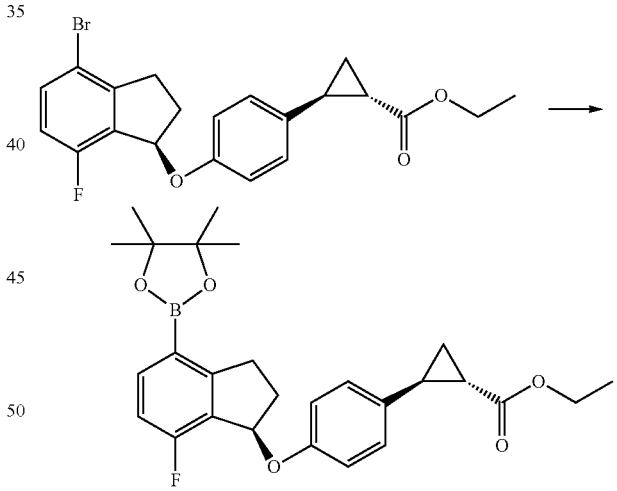

(1S,2S)-2-[4-((R)-4-Bromo-7-fluoro-indan-1-yloxy)-phenyl]-cyclopropanecarboxylic acid ethyl ester (Intermediate 3, 8.23 g, 19.6 mmol), bis(pinacolato)diboron (6.48 g, 25.5 mmol), potassium acetate (5.20 g, 53 mmol) and 1,1'-bis(diphenylphosphino)ferrocenedichloro palladium(II) complex (1.44 g, 1.96 mmol) are combined in dry 1,4-dioxane (100 mL) and degassed with a flow of argon for 10 minutes. The mixture is heated at 100° C. for 8 hours under argon, then allowed to cool to room temperature. The solvent is evaporated, the mixture diluted with water and extracted 3 times with dichloromethane. The combined organic phases are washed with water, dried and the solvent removed. The residue is purified by flash chromatography (0-10% ethyl acetate in cyclohexane) to give the title compound (Yield 5.91 g). LC (METHOD 2): $t_R$=9.31 min; Mass spectrum (ES$^+$): m/z=467 [M+H]$^+$.

Intermediate 5

(1S,2S)-2-[4-((R)-7-Fluoro-4-hydroxy-indan-1-yloxy)-phenyl]-cyclopropanecarboxylic acid ethyl ester

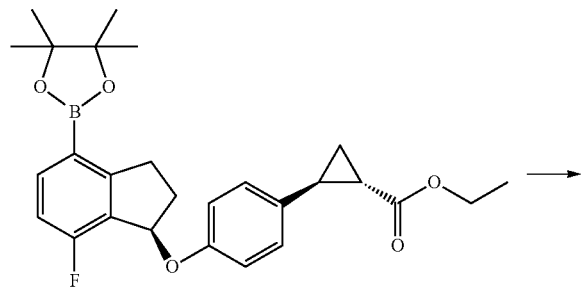

(1S,2S)-2-{4-[(R)-7-Fluoro-4-(4,4,5,5-tetramethyl-[1,3,2]dioxaborolan-2-yl)-indan-1-yloxy]-phenyl}-cyclopropanecarboxylic acid ethyl ester (Intermediate 4, 1.31 g, 2.8 mmol) is suspended in acetic acid (8 mL) and hydrogen peroxide solution (35% in water, 0.97 mL, 11.2 mmol) is added. The mixture is stirred for 1 hour then diluted with water and extracted with ethyl acetate. The organic extracts are washed with water and brine, dried over sodium sulfate and the solvent removed. The residue is dried under vacuum to give the title compound (Yield 0.95 g). LC (METHOD 6): $t_R$=0.57 min; Mass spectrum (ES$^+$): m/z=357 [M+H]$^+$.

Intermediate 6

(1S,2S)-2-{4-[(R)-4-(4-Benzyloxy-phenoxy)-7-fluoro-indan-1-yloxy]-phenyl}-cyclopropanecarboxylic acid ethyl ester

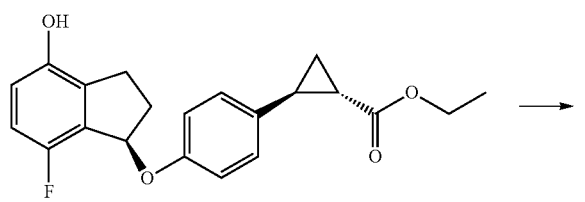

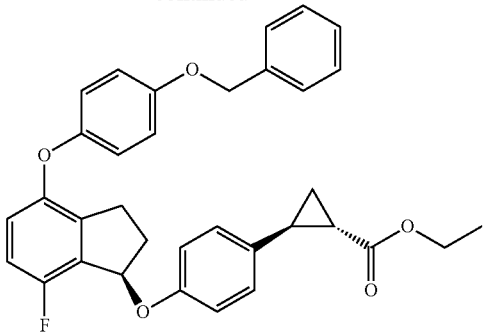

(1S,2S)-2-[4-((R)-7-Fluoro-4-hydroxy-indan-1-yloxy)-phenyl]-cyclopropanecarboxylic acid ethyl ester (Intermediate 5, 0.6 g, 1.7 mmol), 4-benzyloxyphenylboronic acid (1.53 g, 6.7 mmol), copper (II) acetate (306 mg, 1.7 mmol), triethylamine (1.83 mL, 13.1 mmol), 4-dimethylaminopyridine (21 mg, 0.17 mmol) and 4 Å molecular sieves (3 g) are suspended in dichloromethane and stirred under an oxygen atmosphere over a weekend. The mixture is filtered through a plug of CELITE filter aid, washing the filter cake with dichloromethane. The organic phases are washed with 1 M aqueous HCl solution, dried and the solvent removed. The residue is purified by flash chromatography (0-40% ethyl acetate in cyclohexane) to give the title compound (Yield 0.76 g). LC (METHOD 6): $t_R$=1.04 min; Mass spectrum (ES$^+$): m/z=539 [M+H]$^+$.

Intermediate 7

(1S,2S)-2-{4-[(R)-7-Fluoro-4-(4-hydroxy-phenoxy)-indan-1-yloxy]-phenyl}-cyclopropanecarboxylic acid ethyl ester

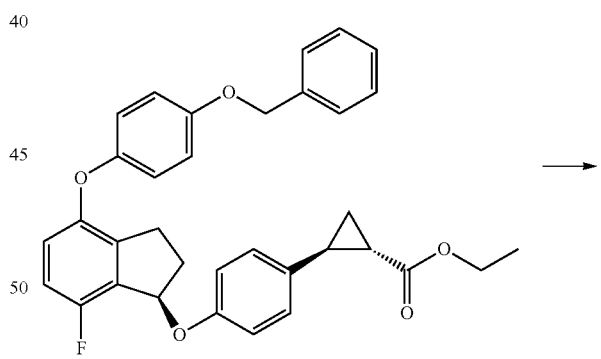

(1S,2S)-2-{4-[(R)-4-(4-Benzyloxy-phenoxy)-7-fluoro-indan-1-yloxy]-phenyl}-cyclopropanecarboxylic acid ethyl ester (Intermediate 6, 0.76 g, 1.3 mmol) is dissolved in 1:1

MeOH/ethyl acetate (20 mL) and hydrogenated at 2 Bar for 1 hour using 10% palladium on carbon as the catalyst. The mixture is filtered through CELITE filter aid and the solvent removed under vacuum the title compound. (Yield 0.60 g). LC (METHOD 6): $t_R$=0.64 min; Mass spectrum (ES$^+$): m/z=449 [M+H]$^+$.

Intermediate 8

(1S,2S)-2-{4-[(R)-4-(4-Benzyloxy-3-fluoro-phenoxy)-7-fluoro-indan-1-yloxy]-phenyl}-cyclopropanecarboxylic acid ethyl ester

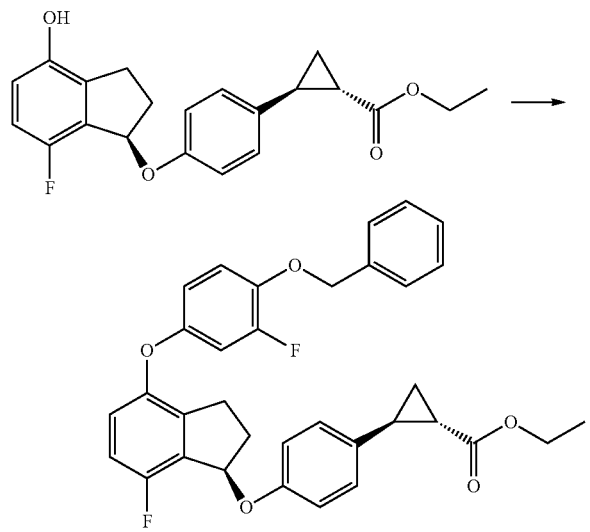

The title compound is prepared from (1S,2S)-2-[4-((R)-7-fluoro-4-hydroxy-indan-1-yloxy)-phenyl]-cyclopropanecarboxylic acid ethyl ester (Intermediate 5, 0.8 g, 2.2 mmol) and 4-benzyloxy-3-fluorophenylboronic acid (2.21 g, 9.0 mmol) in a manner analogous to that described for Intermediate 6 (Yield 0.8 g). LC (METHOD 6): $t_R$=0.96 min; Mass spectrum (ES$^+$): m/z=557 [M+H]$^+$.

Intermediate 9

(1S,2S)-2-{4-[(R)-7-Fluoro-4-(3-fluoro-4-hydroxy-phenoxy)-indan-1-yloxy]-phenyl}-cyclopropanecarboxylic acid ethyl ester

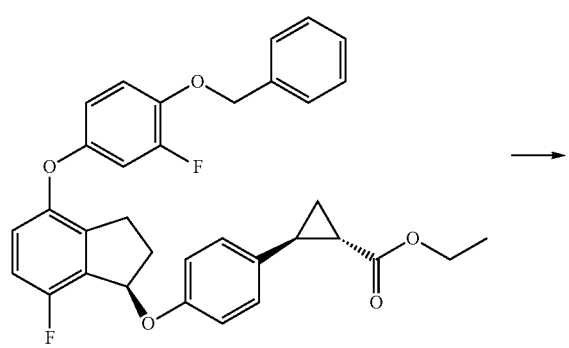

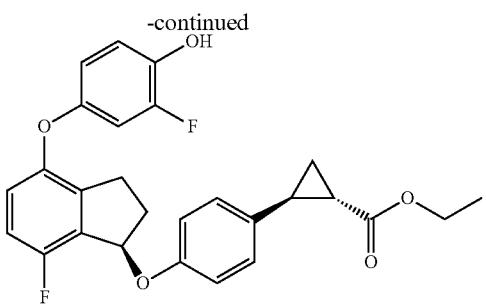

The title compound is prepared from (1S,2S)-2-{4-[(R)-4-(4-benzyloxy-3-fluoro-phenoxy)-7-fluoro-indan-1-yloxy]-phenyl}-cyclopropanecarboxylic acid ethyl ester (Intermediate 8, 0.8 g, 1.44 mmol) in a manner analogous to that described for Intermediate 7 followed by purification by flash chromatography (0-50% ethyl acetate in cyclohexane) (Yield 0.6 g). LC (METHOD 3): $t_R$=4.43 min; Mass spectrum (ES$^+$): m/z=467 [M+H]$^+$.

Intermediate 10

Toluene-4-sulfonic acid 3-hydroxy-3-methyl-butyl ester

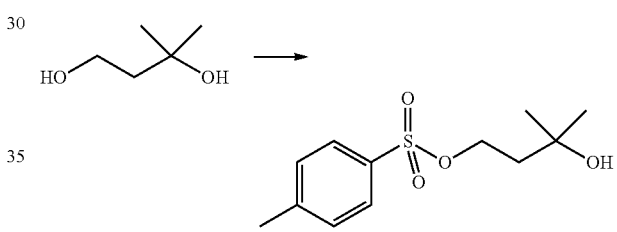

3-Methyl-1,3-butanediol (1.5 mL, 14.1 mmol) is suspended in dry dichloromethane (5 mL) and pyridine (1.24 mL, 15.46 mmol) is added followed by 4-toluenesulfonyl chloride (2.68 g, 14.1 mmol). The mixture is stirred overnight then washed with 1 M aqueous hydrochloric acid, dried and the solvent removed under vacuum. The residue is purified by flash chromatography (0-30% ethyl acetate in cyclohexane) to give the title compound. (Yield 970 mg). LC (METHOD 2): $t_R$=5.67 min; Mass spectrum (ES$^+$): m/z=258 [M+H]$^+$.

Intermediate 11

(1S,2S)-2-(4-{(R)-7-Fluoro-4-[4-(3-hydroxy-3-methyl-butoxy)-phenoxy]-indan-1-yloxy}-phenyl)-cyclopropanecarboxylic acid ethyl ester

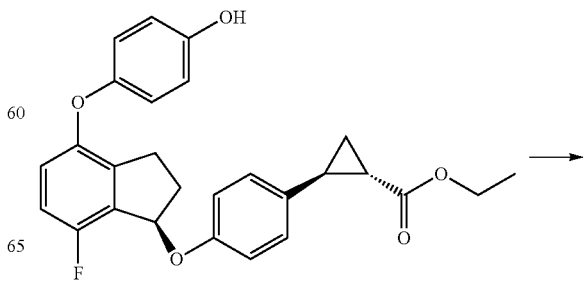

-continued

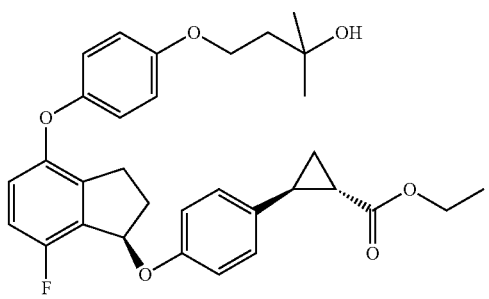

(1S,2S)-2-{4-[(R)-7-Fluoro-4-(4-hydroxy-phenoxy)-indan-1-yloxy]-phenyl}-cyclopropanecarboxylic acid ethyl ester (Intermediate 7, 47 mg, 0.10 mmol), toluene-4-sulfonic acid 3-hydroxy-3-methyl-butyl ester (Intermediate 10, 54 mg, 0.21 mmol), and cesium carbonate (107 mg, 0.21 mmol) are suspended in dry N,N-dimethylformamide (2 mL) and stirred overnight. The mixture is diluted with ethyl acetate, washed with water, dried and the solvent removed. The residue is purified by flash chromatography (gradient of ethyl acetate in cyclohexane) to give the title compound. (Yield 60 mg). LC (METHOD 6): $t_R$=0.75 min; Mass spectrum (ES$^+$): m/z=535 [M+H]$^+$.

The intermediates in the following table are prepared in analogy with the procedure used for the preparation of Intermediate 11 from the starting intermediates described:

| Intermediate | Structure | Starting intermediates | Yield | Analysis |
|---|---|---|---|---|
| 12 | 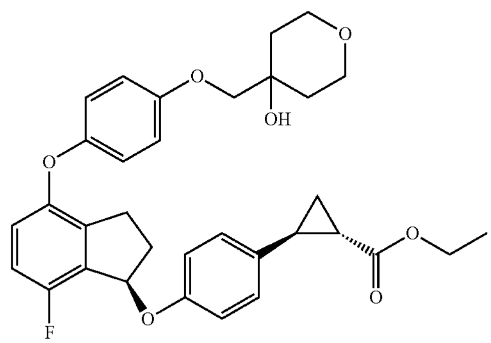 [SMILES: CCOC(=O)[C@H]1C[C@@H]1c1ccc(O[C@@H]2CCc3c(Oc4ccc(OCC5(O)CCOCC5)cc4)ccc(F)c32)cc1] | Intermediate 7 (65 mg) and 1.6-dioxa-spiro[2,5]octane (US2012/46304, 33 mg), 2 hours at 100° C. | 69 mg | LC (METHOD 6): $t_R$ = 0.67 min; Mass spectrum (ES$^+$): m/z = 563 [M + H]$^+$. |
| 13 | 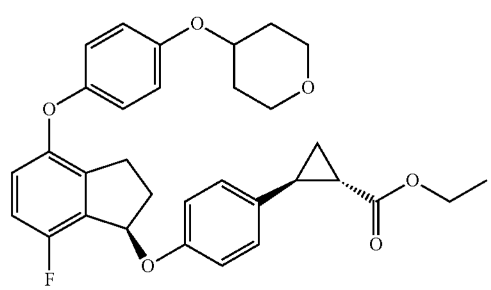 [SMILES: CCOC(=O)[C@H]1C[C@@H]1c1ccc(O[C@@H]2CCc3c(Oc4ccc(OC5CCOCC5)cc4)ccc(F)c32)cc1] | Intermediate 7 (100 mg) and tetrahydro-pyran-4-yl tosylate (EP1367058, 80 | 44 mg | LC (METHOD 6): $t_R$ = 0.82 min; Mass spectrum (ES$^+$): m/z = 533 [M + H]$^+$. |
| 14 | 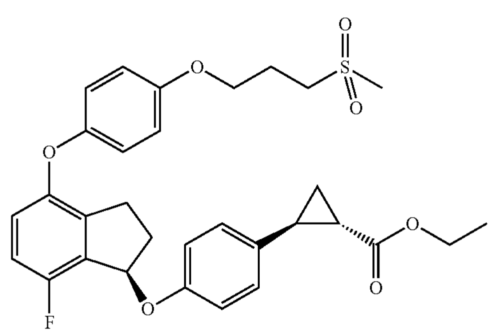 [SMILES: CCOC(=O)[C@H]1C[C@@H]1c1ccc(O[C@@H]2CCc3c(Oc4ccc(OCCCS(C)(=O)=O)cc4)ccc(F)c32)cc1] | Intermediate 7 (100 mg) and 3-methane-sulfonyl-propyl mesylate (US2011/130398, 100 mg) | 40 mg (crude product) | LC (METHOD 6): $t_R$ = 0.65 min; Mass spectrum (ES$^+$): m/z = 569 [M + H]$^+$. |

-continued

| Intermediate | Structure | Starting intermediates | Yield | Analysis |
|---|---|---|---|---|
| 15 | 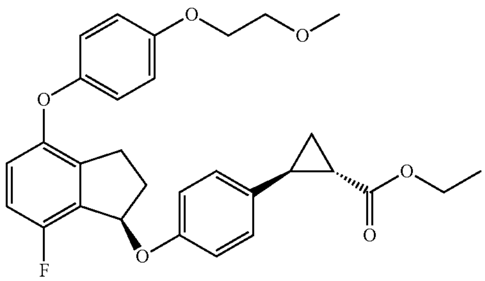 [SMILES: CCOC(=O)[C@H]1C[C@@H]1c1ccc(O[C@@H]2CCc3c(Oc4ccc(OCCOC)cc4)ccc(F)c32)cc1] | Intermediate 7 (150 mg) and 2-bromoethyl-methylesther (100 mg) | 155 mg | LC (METHOD 6): $t_R$ = 0.76 min; Mass spectrum (ES$^+$): m/z = 507 [M + H]$^+$. |
| 16 | 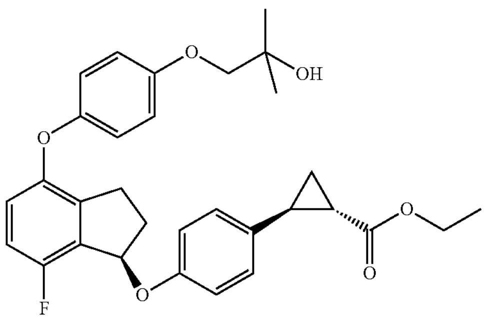 [SMILES: CCOC(=O)[C@H]1C[C@@H]1c1ccc(O[C@@H]2CCc3c(Oc4ccc(OCC(C)(C)O)cc4)ccc(F)c32)cc1] | Intermediate 7 (100 mg) and isobutylene oxide (48 mg) | 78 mg | LC (METHOD 6): $t_R$ = 0.72 min; Mass spectrum (ES$^+$): m/z = 503 [M − OH]$^+$. |
| 17 | 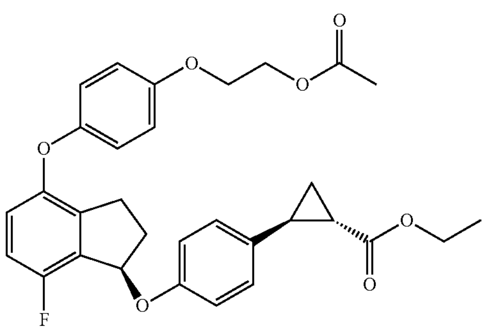 [SMILES: CCOC(=O)[C@H]1C[C@@H]1c1ccc(O[C@@H]2CCc3c(Oc4ccc(OCCOC(C)=O)cc4)ccc(F)c32)cc1] | Intermediate 7 100 mg) and 2-bromoethyl acetate (74 mg) | 85 mg (93% content) | LC (METHOD 6): $t_R$ = 0.73 min; Mass spectrum (ES$^+$): m/z = 535 [M + H]$^+$. |
| 18 | 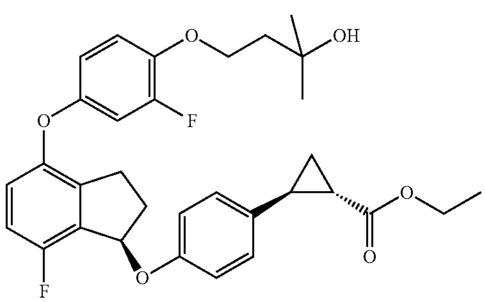 [SMILES: CCOC(=O)[C@H]1C[C@@H]1c1ccc(O[C@@H]2CCc3c(Oc4ccc(OCCC(C)(C)O)c(F)c4)ccc(F)c32)cc1] | Intermediate 9 (200 mg) and intermediate 10 (222 mg) | 150 mg | LC (METHOD 6): $t_R$ = 0.73 min; Mass spectrum (ES$^+$): m/z = 553 [M + H]$^+$. |
| 19 | 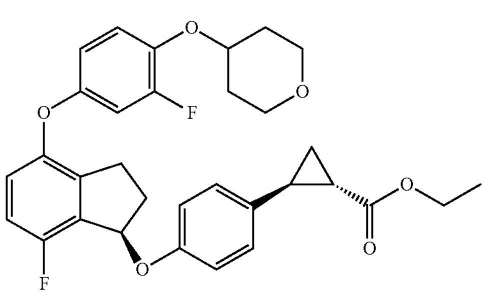 [SMILES: CCOC(=O)[C@H]1C[C@@H]1c1ccc(O[C@@H]2CCc3c(Oc4ccc(OC5CCOCC5)c(F)c4)ccc(F)c32)cc1] | Intermediate 9 (100 mg) and tetrahydro-pyran-4-yl tosylate (EP1367058, 80 mg) | 90 mg (85% content) | LC (METHOD 6): $t_R$ = 0.80 min; Mass spectrum (ES$^+$): m/z = 551 [M + H]$^+$. |

| Intermediate | Structure | Starting intermediates | Yield | Analysis |
|---|---|---|---|---|
| 20 | 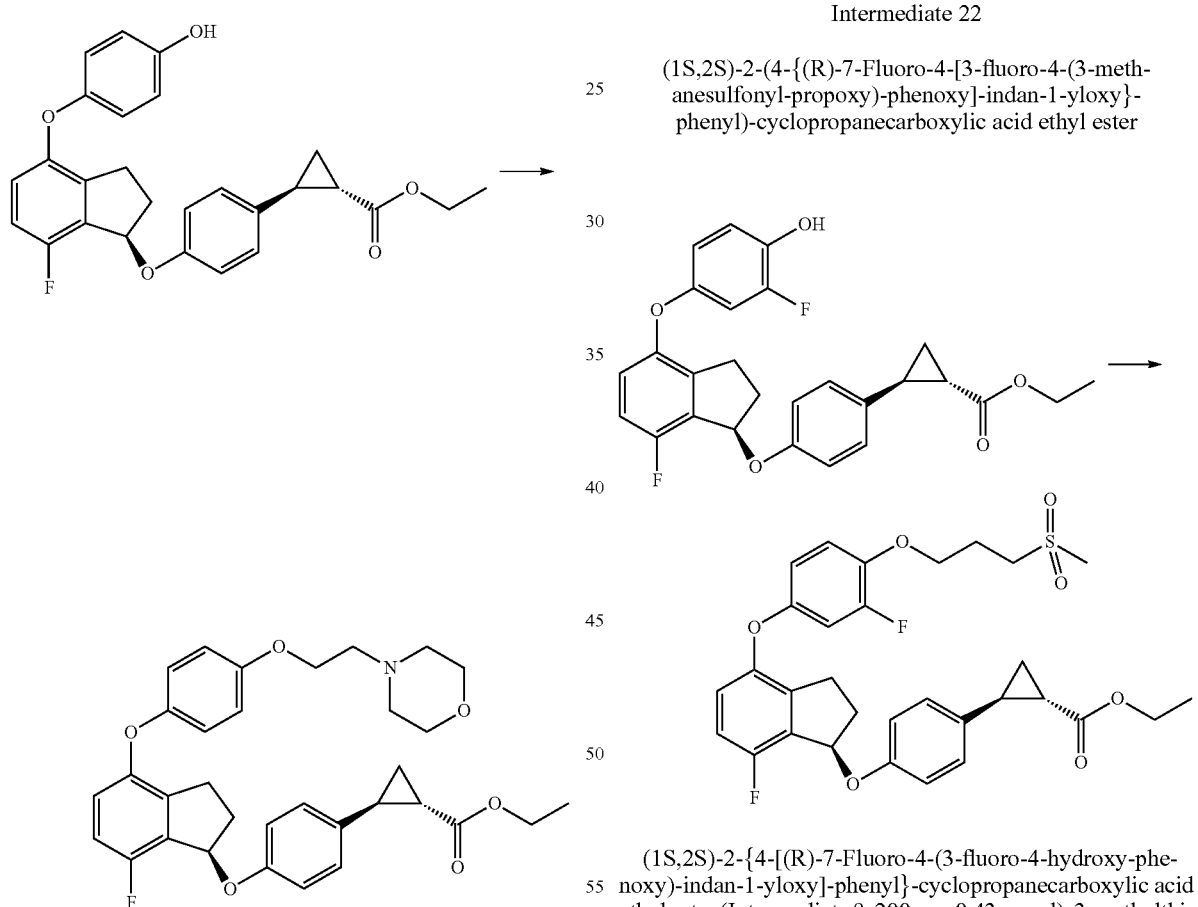 | Intermediate 9 (150 mg) and 2-bromoethyl-methylether (60 uL) | 60 mg | LC (METHOD 6): $t_R$ = 0.76 min; Mass spectrum (ES$^+$): m/z = 525 [M + H]$^+$. |

Intermediate 21

(1S,2S)-2-(4-{(R)-7-Fluoro-4-[4-(2-morpholin-4-yl-ethoxy)-phenoxy]-indan-1-yloxy}-phenyl)-cyclopropanecarboxylic acid ethyl ester (1S,2S)-2-{4-[(R)-7-Fluoro-4-(4-hydroxy-phenoxy)-indan-1-yloxy]-phenyl}-cyclopropanecarboxylic acid ethyl ester (Intermediate 7, 140 mg, 0.29 mmol), N-(2-hydroxyethyl)morpholine (42 mg, 0.32 mmol), and triphenylphosphine (84 mg, 0.32 mmol) are suspended in dry tetrahydrofuran (5 mL) and cooled to 0° C. Di-tert-butyl azodicarboxylate (74 mg, 0.32 mmol) is added, the mixture is stirred for 2 hours at 0° C. then 2 h at room temperature. The solvent is removed under vacuum and residue is purified by flash chromatography (0-20% ethyl acetate in cyclohexane) to give the title compound. (Yield 175 mg, 55% content). LC (METHOD 6): $t_R$=0.57 min; Mass spectrum (ES$^+$): m/z=562 [M+H]$^+$.

Intermediate 22

(1S,2S)-2-(4-{(R)-7-Fluoro-4-[3-fluoro-4-(3-methanesulfonyl-propoxy)-phenoxy]-indan-1-yloxy}-phenyl)-cyclopropanecarboxylic acid ethyl ester (1S,2S)-2-{4-[(R)-7-Fluoro-4-(3-fluoro-4-hydroxy-phenoxy)-indan-1-yloxy]-phenyl}-cyclopropanecarboxylic acid ethyl ester (Intermediate 9, 200 mg, 0.43 mmol), 3-methylthiopropanol (0.044 mL, 0.43 mmol), triphenylphosphine (120 mg, 0.47 mmol) and di-tert-butyl azodicarboxylate (110 mg, 0.47 mmol) are suspended in dry tetrahydrofuran (5 mL) and stirred overnight. A further quantity of 3-methylthiopropanol (0.044 mL, 0.43 mmol), and di-tert-butyl azodicarboxylate (110 mg, 0.47 mmol) are added and the mixture stirred for a further 24 hours. The solvent is removed under vacuum and the residue is purified by flash chromatography (gradient of ethyl acetate in cyclohexane) to give a residue which is suspended in a 1:1 mixture of tetrahydrofuran and water (4 mL) and oxone is added (380 mg, 0.62 mmol). The mixture is stirred for 2 hours then diluted with ethyl acetate and washed with water. The solvent is removed and the residue is purified by flash chromatography (0-50% ethyl acetate in cyclohexane) to give the title compound. (Yield 50 mg). LC (METHOD 5): $t_R$=1.47 min; Mass spectrum (ES$^+$): m/z=587 [M+H]$^+$.

Intermediate 23

4-{(R)-1-[4-((1S,2S)-2-Ethoxycarbonyl-cyclopropyl)-phenoxy]-7-fluoro-indan-4-yloxy}-benzoic acid

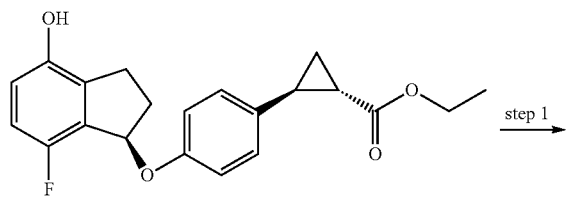

Step 1

(1S,2S)-2-[4-((R)-7-Fluoro-4-hydroxy-indan-1-yloxy)-phenyl]-cyclopropanecarboxylic acid ethyl ester (Intermediate 5, 1.20 g, 3.37 mmol), 4-fluorobenzaldehyde (460 mg, 3.71 mmol), and cesium carbonate (1.21 g, 3.71 mmol) are suspended in dry dimethylformamide and stirred for 10 hours at 120° C. The mixture is allowed to cool to room temperature, diluted with water and extracted with ethyl acetate. The organic extract is dried over sodium sulfate, filtered and the solvent removed to give crude (1S,2S)-2-{4-[(R)-7-Fluoro-4-(4-formyl-phenoxy)-indan-1-yloxy]-phenyl}-cyclopropanecarboxylic acid ethyl (Yield 1.60 g). LC (METHOD 5): $t_R$=1.53 min; Mass spectrum (ES$^+$): m/z=461 [M+H]$^+$.

Step 2

The product from step 1 is suspended in a mixture of water (72 mL) and tert-butanol (180 mL) and 2-methyl-2-butene (30.2 mL, 60.5 mmol) are added followed by sodium dihydrogenphosphate (3.0 g, 21.6 mmol). The mixture is cooled in an ice bath and sodium chlorite (1.35 g, 11.9 mmol) is added. The mixture is stirred for 2 hours at 0° C. then overnight at room temperature. The mixture is diluted with saturated brine and extracted with dichloromethane. The organic phase is dried over sodium sulfate and the solvent removed by evaporation. The residue is purified by flash chromatography (isocratic dichloromethane/methanol/acetic acid 9:0.05:0.05) to give the title compound (Yield 1.18 g). LC (METHOD 4): $t_R$=1.44 min; Mass spectrum (ES$^+$): m/z=477 [M+H]$^+$.

Intermediate 24

(1S,2S)-2-(4-{(R)-4-[4-(Methyl-carbamoyl)-phenoxy]-7-fluoro-indan-1-yloxy}-phenyl)-cyclopropanecarboxylic acid ethyl ester

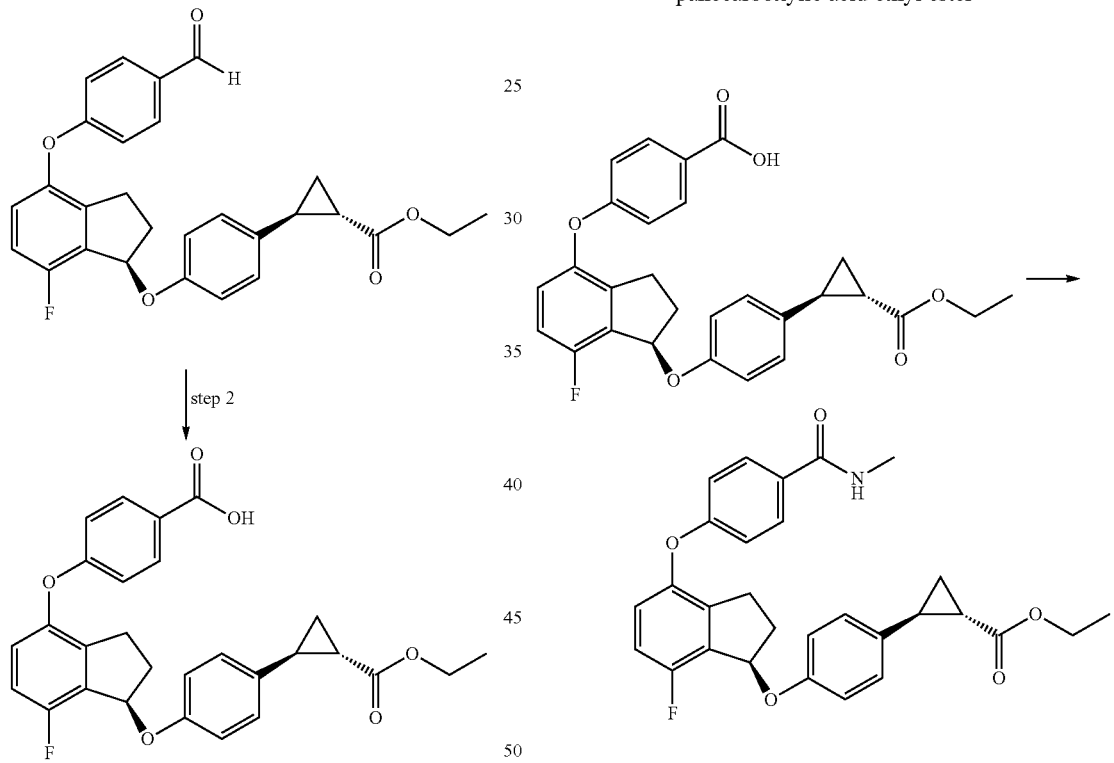

4-{(R)-1-[4-((1S,2S)-2-Ethoxycarbonyl-cyclopropyl)-phenoxy]-7-fluoro-indan-4-yloxy}-benzoic acid (Intermediate 23, 100 mg, 0.21 mmol), methylamine hydrochloride (16 mg, 0.23 mmol), N,N-diisopropylethylamine (0.11 mL, 0.63 mmol) and 0-(benzotriazol-1-yl)-N,N,N',N'-tetramethyluronium tetrafluoroborate (TBTU, 74 mg, 0.23 mmol) are combined in dry tetrahydrofuran (7 mL) and stirred overnight. The mixture is concentrated under vacuum, diluted with ethyl acetate, washed with 1 M aqueous HCl solution, saturated sodium bicarbonate solution and water, dried over sodium sulfate, filtered and the solvent removed. The residue is purified by flash chromatography (50% ethyl acetate in cyclohexane) to give the title compound (Yield 98 mg). LC (METHOD 5): $t_R$=1.36 min; Mass spectrum (ES$^+$): m/z=490 [M+H]$^+$.

The Intermediates in the following table are prepared in analogy with the procedure used for the preparation of Intermediate 24 from the starting intermediates described:

| Intermediate | Structure | Starting intermediates | Yield | Analysis |
|---|---|---|---|---|
| 25 | 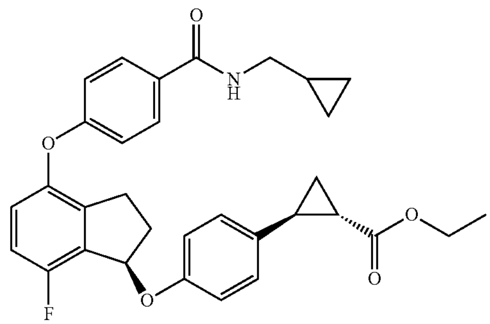 [SMILES: CCOC(=O)[C@H]1C[C@@H]1c1ccc(O[C@@H]2CCc3c(Oc4ccc(C(=O)NCC5CC5)cc4)ccc(F)c32)cc1] | Intermediate 23 (100 mg) and cyclopropylmethyl-amine hydrochloride (25 mg), 2 hours | 92 mg | LC (METHOD 6): $t_R$ = 0.68 min; Mass spectrum (ES$^+$): m/z = 530 [M + H]$^+$. |
| 26 | 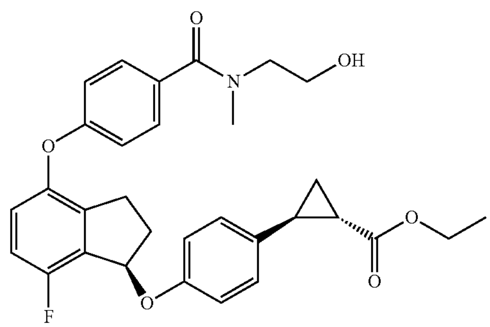 [SMILES: CCOC(=O)[C@H]1C[C@@H]1c1ccc(O[C@@H]2CCc3c(Oc4ccc(C(=O)N(C)CCO)cc4)ccc(F)c32)cc1] | Intermediate 23 (100 mg) and 2-(methylamino)ethanol (17 mg) | 102 mg | LC (METHOD 5): $t_R$ = 1.30 min; Mass spectrum (ES$^+$): m/z = 534 [M + H]$^+$. |
| 27 | 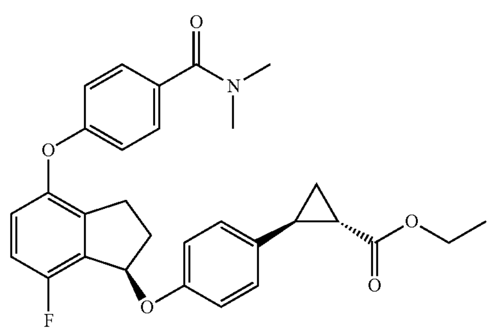 [SMILES: CCOC(=O)[C@H]1C[C@@H]1c1ccc(O[C@@H]2CCc3c(Oc4ccc(C(=O)N(C)C)cc4)ccc(F)c32)cc1] | Intermediate 23 (100 mg) and dimethylamine hydrochloride (19 mg) | 96 mg | LC (METHOD 5): $t_R$ = 1.42 min; Mass spectrum (ES$^+$): m/z = 504 [M + H]$^+$. |
| 28 | 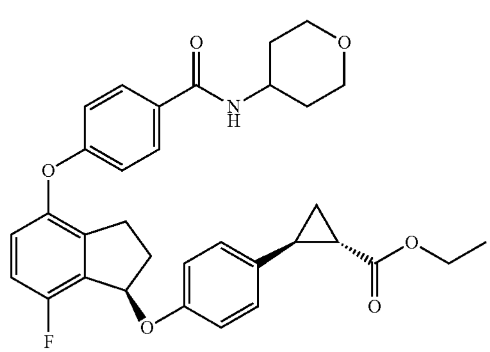 [SMILES: CCOC(=O)[C@H]1C[C@@H]1c1ccc(O[C@@H]2CCc3c(Oc4ccc(C(=O)NC5CCOCC5)cc4)ccc(F)c32)cc1] | Intermediate 23 (116 mg) and 4-aminotetrahydropyran hydrochloride (36 mg) | 103 mg | LC (METHOD 5): $t_R$ = 1.38 min; Mass spectrum (ES$^+$): m/z = 560 [M + H]$^+$. |

| Intermediate | Structure | Starting intermediates | Yield | Analysis |
|---|---|---|---|---|
| 29 | 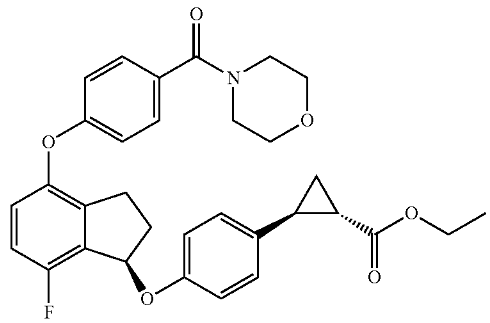 [SMILES: CCOC(=O)[C@H]1C[C@@H]1c1ccc(O[C@@H]2CCc3c(Oc4ccc(C(=O)N5CCOCC5)cc4)ccc(F)c32)cc1] | Intermediate 23 (120 mg) and morpholine (24 mg) | 42 mg | LC (METHOD 5): $t_R$ = 1.39 min; Mass spectrum (ES$^+$): m/z = 546 [M + H]$^+$. |
| 30 | 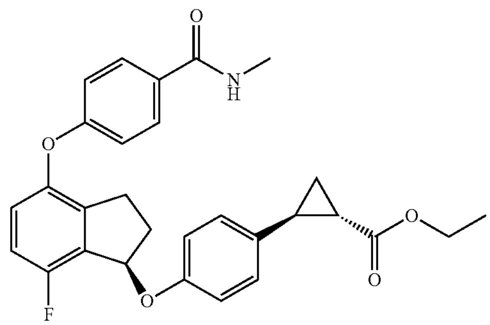 | Intermediate 23 (100 mg) and ethylamine hydrochloride (19 mg) | 33 mg | LC (METHOD 5): $t_R$ = 1.41 min; Mass spectrum (ES$^+$): m/z = 504 [M + H]$^+$. |

Intermediate 31

(1S,2S)-2-{4-[(R)-4-(4-Cyano-phenoxy)-7-fluoro-indan-1-yloxy]-phenyl}-cyclopropanecarboxylic acid ethyl ester

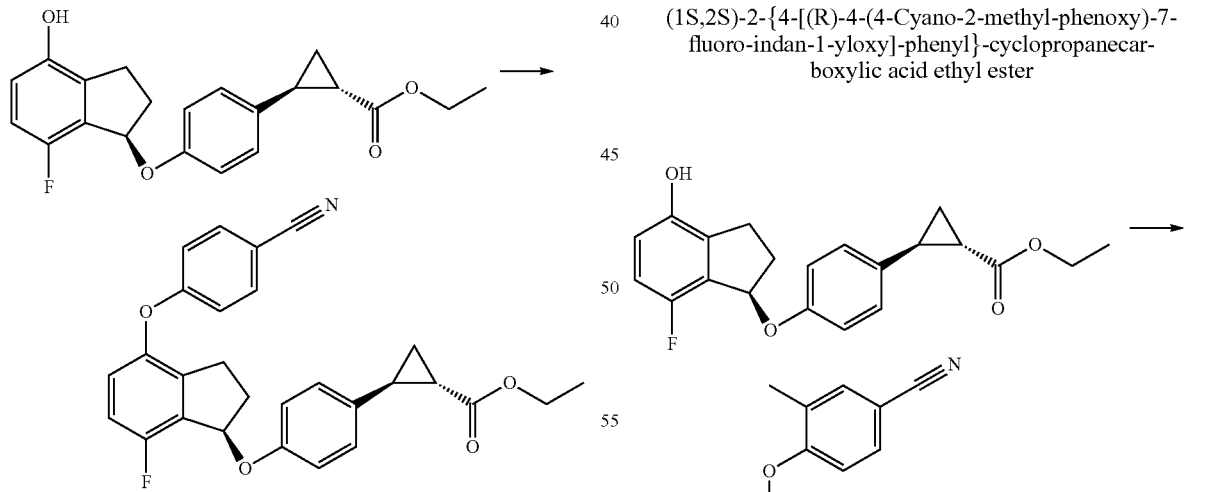

(1S,2S)-2-[4-((R)-7-Fluoro-4-hydroxy-indan-1-yloxy)-phenyl]-cyclopropanecarboxylic acid ethyl ester (Intermediate 5, 146 mg, 0.41 mmol), 4-fluorobenzonitrile (55 mg, 0.45 mmol), and cesium carbonate (145 mg, 0.45 mmol) are suspended in dry dimethylformamide (10 mL) and stirred for 3 hours at 100° C. followed by room temperature overnight. The mixture is diluted with water and extracted with ethyl acetate. The organic extract is dried over sodium sulfate, filtered and the solvent removed. The residue is purified by flash chromatography (10% ethyl acetate in cyclohexane) to give the title compound (Yield 62 mg). LC (METHOD 5): $t_R$=1.54 min; Mass spectrum (ES$^+$): m/z=458 [M+H]$^+$.

Intermediate 32

(1S,2S)-2-{4-[(R)-4-(4-Cyano-2-methyl-phenoxy)-7-fluoro-indan-1-yloxy]-phenyl}-cyclopropanecarboxylic acid ethyl ester The title compound was synthesized in analogy to Intermediate 31 using 4-fluoro-3-methylbenzonitrile in place of 4-fluorobenzonitrile heating at 100° C. for 16 hours (Yield 46 mg). LC (METHOD 6): $t_R$=0.83 min; Mass spectrum (ES$^+$): m/z=472 [M+H]$^+$.

Intermediate 33

(1S,2S)-2-{4-[(R)-4-(4-Cyano-2-fluoro-phenoxy)-7-fluoro-indan-1-yloxy]-phenyl}-cyclopropanecarboxylic acid ethyl ester

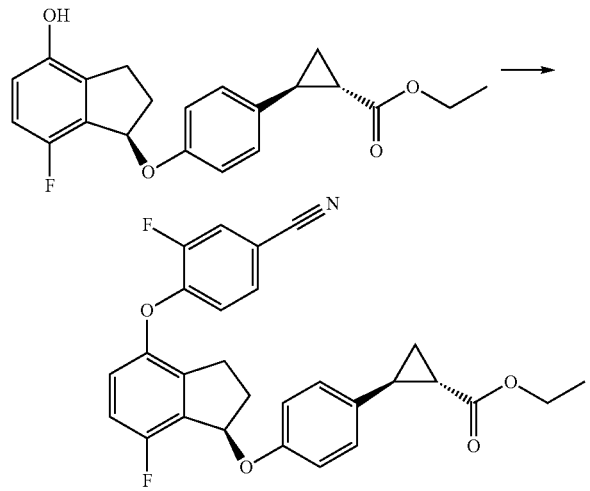

The title compound was synthesized in analogy to Intermediate 31 using 3,4-difluorobenzonitrile in place of 4-fluorobenzonitrile heating at 100° C. for 3 hours (Yield 110 mg). LC (METHOD 6): $t_R$=0.72 min; Mass spectrum (ES$^+$): m/z=475 [M+H]$^+$.

Intermediate 34

(1S,2S)-2-{4-[(R)-4-(4-Cyano-3-methoxy-phenoxy)-7-fluoro-indan-1-yloxy]-phenyl}-cyclopropanecarboxylic acid ethyl ester

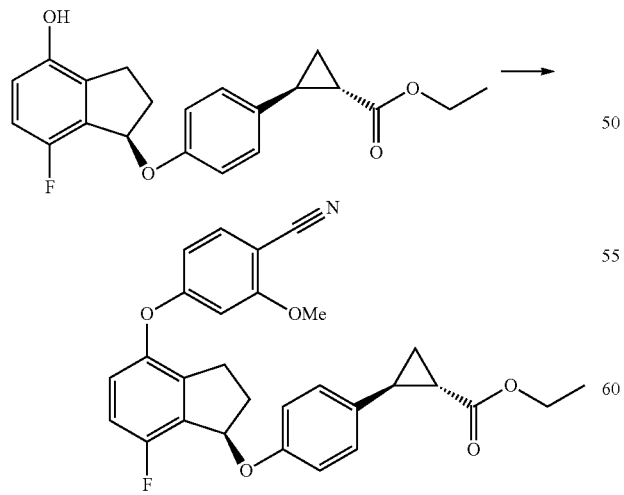

The title compound was synthesized in analogy to Intermediate 31 using 4-fluoro-2-methoxybenzonitrile in place of 4-fluorobenzonitrile heating at 130° C. for 3 hours under microwave irradiation. (Yield: 250 mg). LC (METHOD 5): $t_R$=1.49 min; Mass spectrum (ES$^+$): m/z=488 [M+H]$^+$.

Intermediate 35

(1S,2S)-2-[4-((R)-5,7-Difluoro-4-hydroxy-indan-1-yloxy)-phenyl]-cyclopropanecarboxylic acid ethyl ester

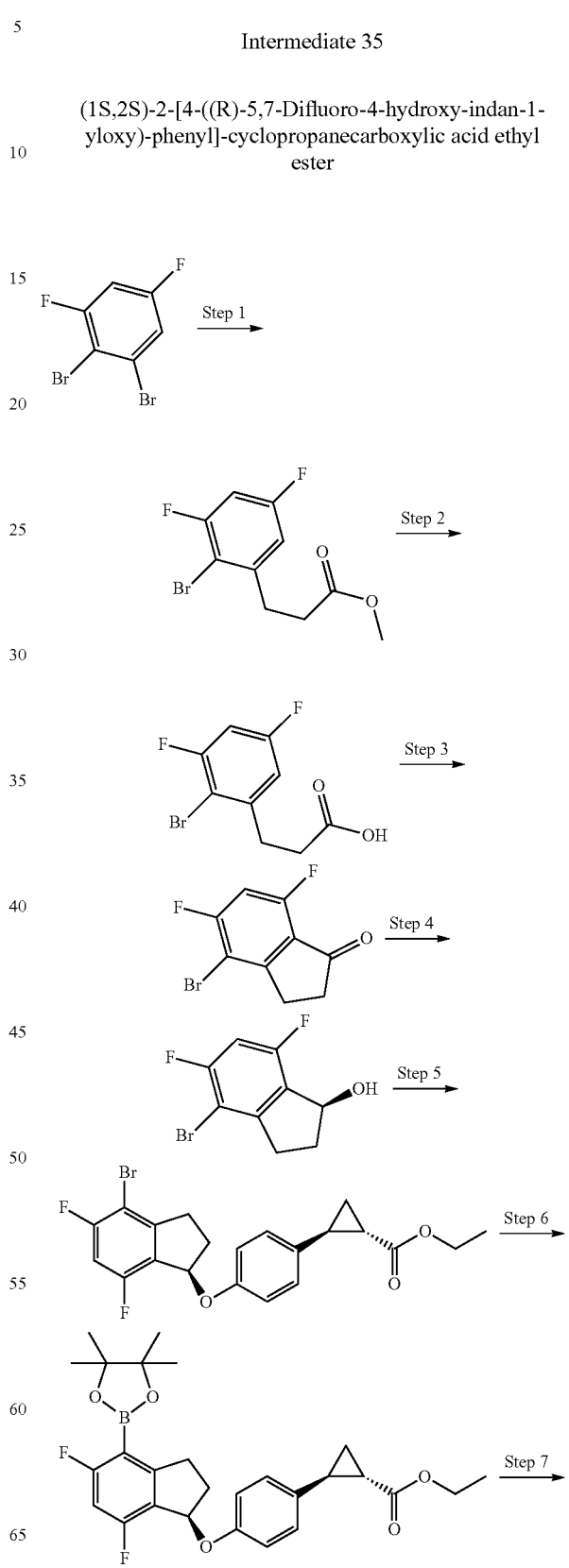

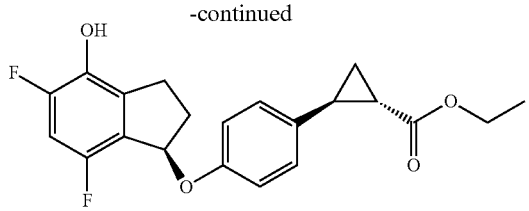

Step 1: Methyl 3-(2-bromo-3,5-difluorophenyl)propanoate

A mixture of 1,2-dibromo-3,5-difluorobenzene (4.5 g), 3,3-dimethoxyprop-1-ene (5.1 mL), tetrabutylammonium chloride (4.6 g) and triethylamine (3.5 mL) in N,N-dimethylformamide (50 mL) is purged with nitrogen for 20 minutes. Palladium-(II)-acetate (111 mg) is added and the mixture heated for 16 hours at 90° C. After cooling the mixture is partitioned between aqueous HCl (1 M) and diethyl ether, the organic layer dried ($Na_2SO_4$), volatiles evaporated under reduced pressure and the residue purified by column chromatography (silica gel; hexane:ethyl acetate 98:2→80:20) to give the title compound (Yield 3.6 g).
GC (METHOD 1): $t_R$=9.36 min.

Step 2: 3-(2-Bromo-3,5-difluorophenyl)propanoic acid

Methyl 3-(2-bromo-3,5-difluorophenyl)propanoate (prepared as described in Step 1, 4.3 g) in aqueous NaOH (4 M, 13.5 mL) and 2-propanol (30 mL) is heated at 50° C. for 2 hours. Water is added, the mixture washed with diethyl ether, acidified to ca. pH 5 by adding concentrated aqueous HCl, and extracted twice with diethyl ether. The combined extracts of the acidified mixture are washed with brine and volatiles evaporated under reduced pressure. The resulting material (Yield 3.6 g) is used in the next step without further purification. LC (METHOD 7): $t_R$=0.99 min.

Step 3: 4-Bromo-5,7-difluoro-indan-1-one 3-(2-Bromo-3,5-difluorophenyl)propanoic acid (from Step 2, 3.0 g) is stirred with chlorosulfonic acid (10 mL) for 2 hours at ambient temperature. The mixture is then added dropwise to a vigorously stirred mixture of water and ice (200 mL) and further stirred for 15 minutes. Extraction with diethyl ether, subsequent washing of the organic layer with water, NaOH (0.2 M), and brine, drying ($Na_2SO_4$) and removal of the solvent under reduced pressure gives the crude product (Yield 2.7 g) that is used in the next step without further purification. LC (METHOD 7): $t_R$=1.16 min.

Step 4: (S)-4-Bromo-5,7-difluoro-2,3-dihydro-1H-inden-1-ol

Carried out in analogy to the preparation of Intermediate 2 (Yield 2.45 g).
GC (METHOD 1): $t_R$=9.33 min. Chiral HPLC $t_R$=9.33 min (Column Daicel Chiralcel OJ-H; 250×4.6 mm 5 µm; hexane: EtOH 95:5; 1 mL/min; 25° C.).

Step 5: (1S,2S)-2-[4-((R)-4-Bromo-5,7-difluoroindan-1-yloxy)phenyl]cyclopropanecarboxylic acid ethyl ester Carried out in analogy to the preparation of Intermediate 3 LC (METHOD 2): $t_R$=9.03 min; Mass spectrum ($ES^+$): m/z=437/439 $[M+H]^+$.

Step 6: (1S,2S)-2-{4-[(R)-5,7-Difluoro-4-(4,4,5,5-tetramethyl-[1,3,2]dioxaborolan-2-yl)-indan-1-yloxy]-phenyl}-cyclopropanecarboxylic acid ethyl ester Carried out in analogy to the preparation of Intermediate 4 heating for 2 days at 100° C. then at 130° C. under microwave irradiation for 3 hours. LC (METHOD 6): $t_R$=0.90 min; Mass spectrum ($ES^+$): m/z=485 $[M+H]^+$.

Step 7: (1S,2S)-2-[4-((R)-5,7-Difluoro-4-hydroxy-indan-1-yloxy)phenyl]cyclopropanecarboxylic acid ethyl ester Prepared in analogy to Intermediate 5 (Yield: 40 mg). LC (METHOD 5): $t_R$=1.25 min; Mass spectrum (ES−): m/z=373 $[M-H]^-$.

Intermediate 36

(1S,2S)-2-{4-[(R)-4-(4-Cyano-phenoxy)-5,7-difluoro-indan-1-yloxy]-phenyl}-cyclopropanecarboxylic acid ethyl ester

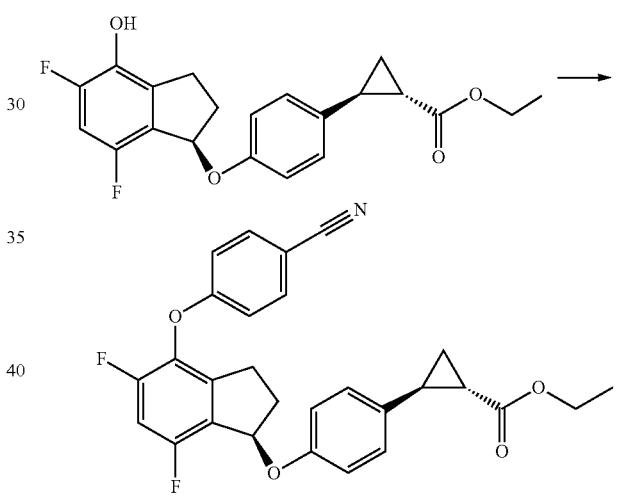

The title compound was synthesized from Intermediate 35 (40 mg, 0.09 mmol) in analogy to Intermediate 31 heating at 130° C. for 1 hour. (Yield: 40 mg). LC (METHOD 5): $t_R$=1.49 min; Mass spectrum ($ES^+$): m/z=476 $[M+H]^+$.

Intermediate 37

1-(4-Bromo-phenyl)-3-isopropyl-1H-pyrazole

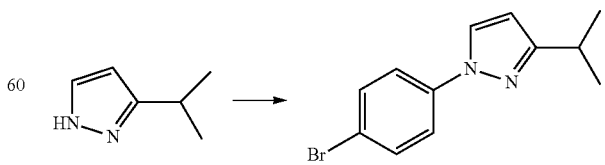

3-Isopropylpyrazole (588 mg, 5.43 mmol), 1-bromo-4-iodobenzene (15.11 g, 53.4 mmol), cesium carbonate (5.22 g, 16.0 mmol), copper(I)iodide (1.02 g, 5.34 mmol) and N,N'- dimethylethylenediamine (570 uL, 5.34 mmol) are combined in dry N,N-dimethylformamide (100 mL) and heated at 100° C. for 3 hours under a nitrogen atmosphere. The mixture is cooled, poured into water and extracted with diethyl ether. The organic phase is dried and the solvent removed. The residue is purified by flash chromatography (30% dichloromethane in cyclohexane) to give the title compound (Yield 1.37 g) LC (METHOD 5): $t_R$=1.47 min; Mass spectrum (ES$^+$): m/z=265/267 [M+H]$^+$.

Intermediate 38

4-(4-Bromo-2,6-dimethyl-phenoxy)-2-methyl-butan-2-ol

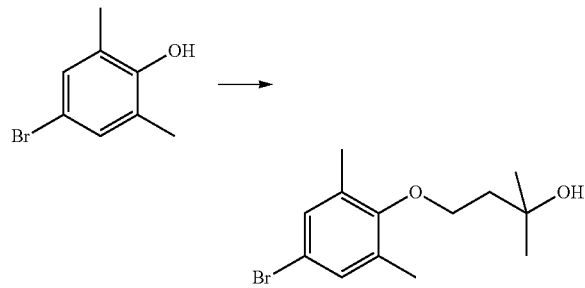

4-Bromo-2,6-dimethylphenol (2.00 g, 9.95 mmol), toluene-4-sulfonic acid 3-hydroxy-3-methyl-butyl ester (Intermediate 10, 2.83 g, 10.9 mmol) and potassium carbonate (1.01 g, 10.9 mmol) are combined in N,N-dimethylformamide (50 mL) and heated at 80° C. for 24 hours. The mixture is cooled, poured into water and extracted with diethyl ether. The organic phase is dried and the solvent removed. The residue is purified by flash chromatography (0-50% ethyl acetate in cyclohexane) to give the title compound (Yield 2.00 g). GC (METHOD 1): $t_R$=11.26 min; Mass spectrum (EI$^+$): m/z=286/288 [M]$^+$.

Intermediate 39

4-(2-Methyl-2H-tetrazol-5-yl)-phenylboronic acid

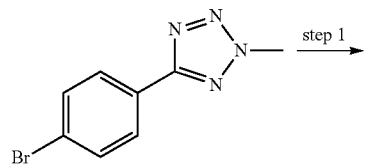

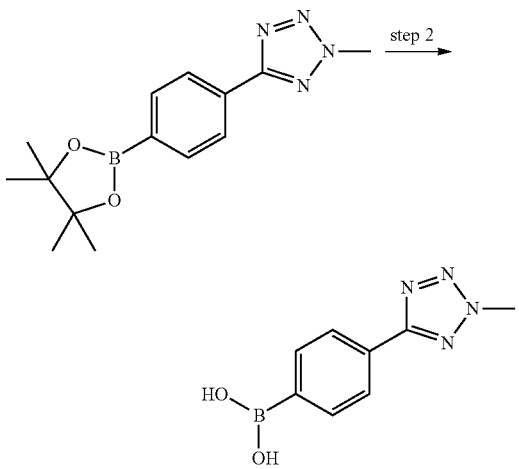

Step 1: 5-(4-Bromo-phenyl)-2-methyl-2H-tetrazole (0.5 g, 2.1 mmol), bis(pinacolato)diboron (0.58 g, 2.3 mmol), potassium acetate (0.55 g, 5.6 mmol) and 1,1'-bis(diphenylphosphino)ferrocenedichloro palladium(II) (154 mg, 0.2 mmol) are suspended in dry dioxane, degassed with a flow of nitrogen and heated under microwaved irradiation at 110° C. for 1 hour. The mixture is diluted with ethyl acetate and washed with water, dried and the solvent removed. The residue is purified by flash chromatography (0-50% ethyl acetate in cyclohexane) to give the boronic ester (Yield 0.45 g). GC (METHOD 1): $t_R$=12.64 min; Mass spectrum (EI$^+$): m/z=286 [M]$^+$ Step 2: The material from step 1 is suspended in a mixture of water and acetone (1:1, 16 mL) and sodium metaperiodate (1.5 g, 7 mmol) and ammonium acetate (0.54 g, 7 mmol) are added. The mixture is stirred overnight, then filtered to remove un-dissolved solids and the acetone evaporated under vacuum. The residue is cooled to 0° C., basified with 1 M sodium hydroxide solution and washed with dichloromethane. The aqueous phase is acidified with 1 M HCl solution and extracted with ethyl acetate. The organic phase is dried and the solvent removed to give the title compound as a crude product (Yield 225 mg). LC (METHOD 5): $t_R$=0.69 min; Mass spectrum (ES$^+$): m/z=205 [M+H]$^+$.

The intermediates in the following table are prepared in analogy with the procedure used for the preparation of Intermediate 37 from the starting intermediates described:

| Intermediate | Structure | Starting intermediate | Yield | Analysis |
| --- | --- | --- | --- | --- |
| 40 | 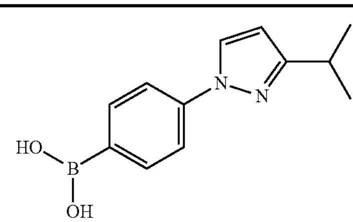 | Intermediate 37 | 387 mg | LC (METHOD 8): $t_R$ = 3.89 min; Mass spectrum (ES$^+$): m/z = 231 [M + H]$^+$. |

-continued

| Intermediate | Structure | Starting intermediate | Yield | Analysis |
|---|---|---|---|---|
| 41 | ![structure] | Intermediate 38 | 330 mg | LC (METHOD 5): $t_R = 0.78$ min; Mass spectrum (ES$^+$): m/z = 253 [M + H]$^+$. |
| 42 | ![structure] | 5-(4-Bromo-phenyl)-3-methyl-[1,2,4]-oxadiazole | 300 mg | LC (METHOD 5): $t_R = 0.76$ min; Mass spectrum (ES$^+$): m/z = 205 [M + H]$^+$. |
| 43 | ![structure] | 3-(4-Bromo-phenyl)-1,5-dimethyl-1H-[1,2,4]triazole (WO2009/105500) | 120 mg | LC (METHOD 5): $t_R = 0.61$ min; Mass spectrum (ES$^+$): m/z = 218 [M + H]$^+$. |

Intermediate 44

4-(2-Hydroxy-2-methyl-propylcarbamoyl)-phenylboronic acid

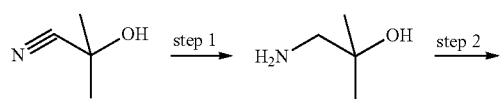

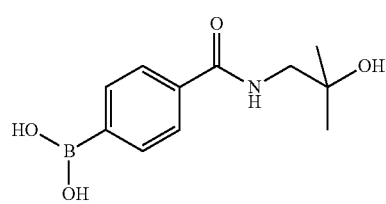

Step 1

Lithium aluminum hydride (2 M in tetrahydrofuran, 29.1 mL, 78.3 mmol) is diluted with dry tetrahydrofuran (90 mL) and cooled to 0° C. under nitrogen, acetonecyanohydrin (3.70 g, 39.1 mmol) in dry tetrahydrofuran (10 mL) is added dropwise and the mixture then heated at reflux for 4 hours. The mixture is cooled and the solvent evaporated under vacuum. A small amount of water is added to the residue and the mixture repeatedly extracted with ethyl acetate and dichloromethane. The combined organic extracts are evaporated to give crude 2-hydroxy-2-methylpropylamine (Yield 1.0 g). GC (METHOD 1): $t_R$=2.06 min; Mass spectrum (EI$^+$): m/z=89 [M]$^+$.

Step 2

4-Carboxyphenylboronic acid (0.5 g, 3.0 mmol) is suspended in dry dichloromethane (8 mL) and oxalylchloride (2 M in dichloromethane, 3.0 mL, 6.0 mmol) is added followed by 2 drops of N,N-dimethylformamide. The mixture is stirred for 3 hours then the solvent removed under vacuum. 2-Hydroxy-2-methylpropylamine (step 1, 800 mg, 9.0 mmol) and triethylamine (2.0 mL, 13.8 mmol) in dichloromethane (12 mL) are added to the residue and the mixture stirred for 30 minutes. The mixture is diluted with 1 M HCl and the phases separated. The aqueous layer is extracted several times with ethyl acetate. The combined organic phases are dried and the solvent removed to give the title compound as a crude product. LC (METHOD 5): $t_R$=0.55 min; Mass spectrum (ES$^+$): m/z=238 [M+H]$^+$.

The intermediates in the following table are prepared in analogy with the procedure used for the preparation of Intermediate 6 from the starting intermediates described:

| Intermediate | Structure | Starting intermediates | Yield | Analysis |
|---|---|---|---|---|
| 45 | 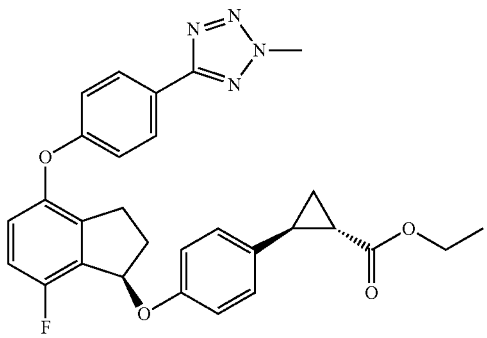 [SMILES: CCOC(=O)[C@H]1C[C@@H]1c1ccc(O[C@@H]2CCc3c(Oc4ccc(-c5nnn(C)n5)cc4)ccc(F)c32)cc1] | Intermediate 5 (196 mg) and Intermediate 39 (225 mg) | 177 mg | LC (METHOD 6): $t_R$ = 0.74 min; Mass spectrum (ES$^+$): m/z = 515 [M + H]$^+$. |
| 46 | 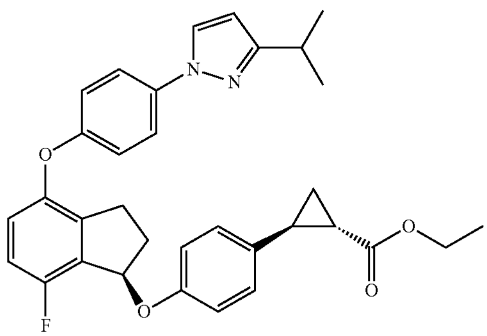 [SMILES: CCOC(=O)[C@H]1C[C@@H]1c1ccc(O[C@@H]2CCc3c(Oc4ccc(-n5ccc(C(C)C)n5)cc4)ccc(F)c32)cc1] | Intermediate 5 (211 mg) and Intermediate 40 (234 mg) | 48 mg | LC (METHOD 6): $t_R$ = 1.03 min; Mass spectrum (ES$^+$): m/z = 541 [M + H]$^+$. |
| 47 | 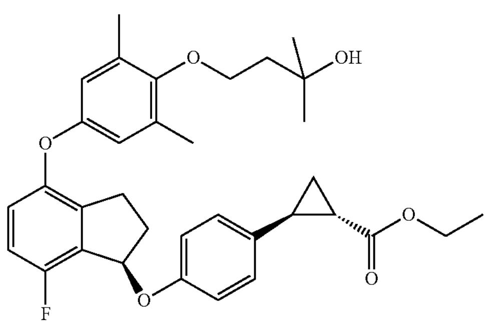 [SMILES: CCOC(=O)[C@H]1C[C@@H]1c1ccc(O[C@@H]2CCc3c(Oc4cc(C)c(OCCC(C)(C)O)c(C)c4)ccc(F)c32)cc1] | Intermediate 5 (200 mg) and Intermediate 41 (283 mg) | 24 mg | LC (METHOD 6): $t_R$ = 0.85 min; Mass spectrum (ES$^+$): m/z = 563 [M + H]$^+$. |
| 48 | 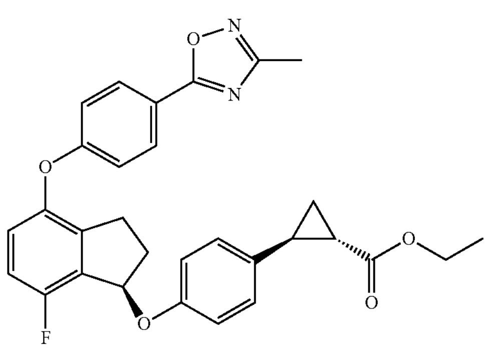 [SMILES: CCOC(=O)[C@H]1C[C@@H]1c1ccc(O[C@@H]2CCc3c(Oc4ccc(-c5nc(C)no5)cc4)ccc(F)c32)cc1] | Intermediate 5 (200 mg) and Intermediate 42 (229 mg) | 25 mg | LC (METHOD 5): $t_R$ = 1.62 min; Mass spectrum (ES$^+$): m/z = 515 [M + H]$^+$. |

-continued

| Intermediate | Structure | Starting intermediates | Yield | Analysis |
|---|---|---|---|---|
| 49 | 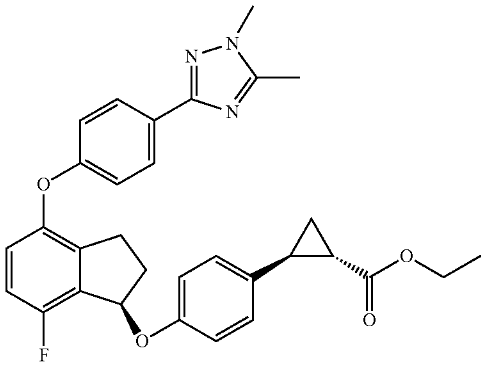 [SMILES: CCOC(=O)[C@H]1C[C@@H]1c1ccc(O[C@@H]2CCc3c(Oc4ccc(-c5nc(C)n(C)n5)cc4)ccc(F)c32)cc1] | Intermediate 5 (476 mg) and Intermediate 43 (290 mg) | 100 mg | LC (METHOD 6): $t_R$ = 0.66 min; Mass spectrum (ES$^+$): m/z = 529 [M + H]$^+$. |
| 50 | 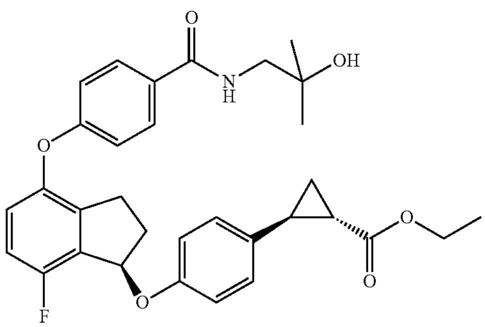 [SMILES: CCOC(=O)[C@H]1C[C@@H]1c1ccc(O[C@@H]2CCc3c(Oc4ccc(C(=O)NCC(C)(C)O)cc4)ccc(F)c32)cc1] | Intermediate 5 (230 mg) and Intermediate 44 (612 mg) | 100 mg | LC (METHOD 5): $t_R$ = 1.33 min; Mass spectrum (ES$^+$): m/z = 548 [M + H]$^+$. |
| 51 | 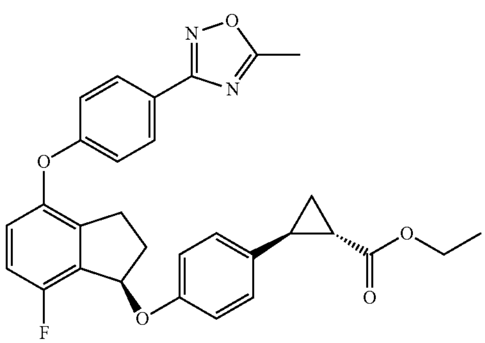 [SMILES: CCOC(=O)[C@H]1C[C@@H]1c1ccc(O[C@@H]2CCc3c(Oc4ccc(-c5noc(C)n5)cc4)ccc(F)c32)cc1] | Intermediate 5 (230 mg) and 4-(5-Methyl-[1,2,4]-oxadiazol-3-yl)-phenylboronic acid (US2012/71462, 260 mg) | 300 mg crude | LC (METHOD 5): $t_R$ = 1.66 min; Mass spectrum (ES$^+$): m/z = 515 [M + H]$^+$. |
| 52 | 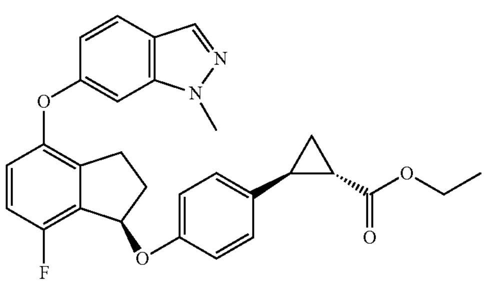 [SMILES: CCOC(=O)[C@H]1C[C@@H]1c1ccc(O[C@@H]2CCc3c(Oc4ccc5cnn(C)c5c4)ccc(F)c32)cc1] | Intermediate 5 (200 mg) and 1-methylindazole-6-boronic acid (197 mg) | 156 mg | LC (METHOD 6): $t_R$ = 0.75 min; Mass spectrum (ES$^+$): m/z = 487 [M + H]$^+$. |
| 53 | 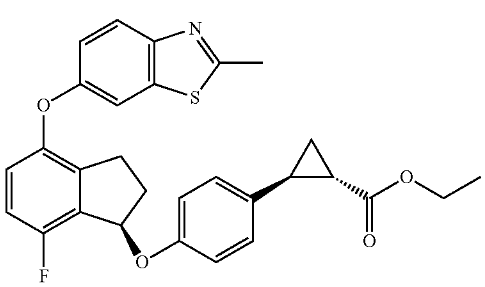 [SMILES: CCOC(=O)[C@H]1C[C@@H]1c1ccc(O[C@@H]2CCc3c(Oc4ccc5nc(C)sc5c4)ccc(F)c32)cc1] | Intermediate 5 (250 mg) and 2-methylbenzothiazole-5-boronic acid (197 mg) | 400 mg crude | LC (METHOD 6): $t_R$ = 0.87 min; Mass spectrum (ES$^+$): m/z = 504 [M + H]$^+$. |

-continued

| Intermediate | Structure | Starting intermediates | Yield | Analysis |
|---|---|---|---|---|
| 54 | 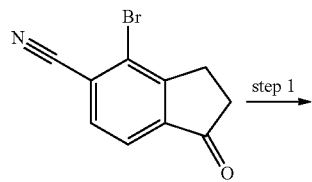 | Intermediate 5 (100 mg) and 4-(methylsulphonyl) phenylboronic acid (168 mg) | 400 mg crude | LC (METHOD 6): $t_R$ = 0.62 min; Mass spectrum (ES$^+$): m/z = 511 [M + H]$^+$. |
| 55 | 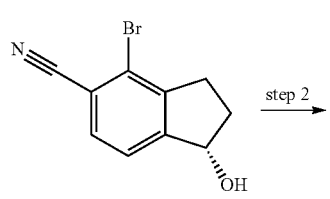 | Intermediate 5 (200 mg) and 2-methylquinoline-6-boronic acid (Nature Chem. Biol., 2008, 691-699. 466 mg) | 320 mg crude | LC (METHOD 5): $t_R$ = 1.51 min; Mass spectrum (ES$^+$): m/z = 498 [M + H]$^+$. |

Intermediate 56

(1S,2S)-2-{4-[(R)-4-(6-Chloro-pyridin-3-ylmethyl)-5-cyano-indan-1-yloxy]-phenyl}-cyclopropanecarboxylic acid ethyl ester

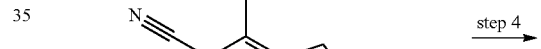

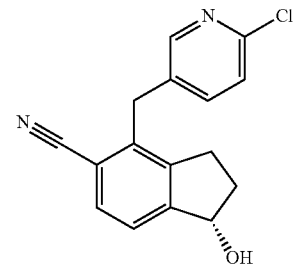

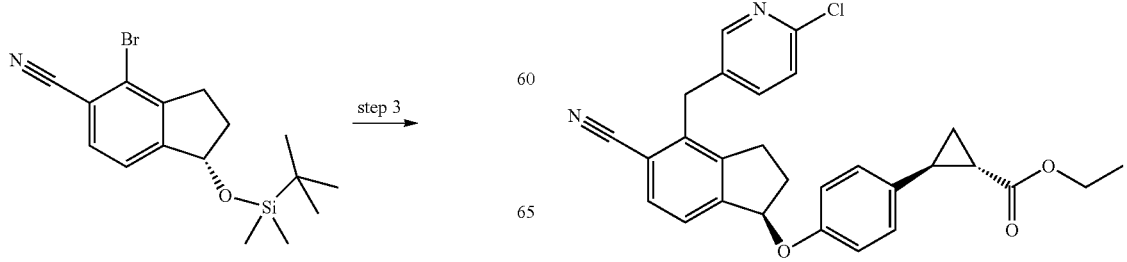

Step 1: (S)-4-Bromo-1-hydroxy-indan-5-carbonitrile

The compound is synthesized from 4-bromo-1-oxo-indan-5-carbonitrile (2.20 g, 5.1 mmol) in analogy to the preparation of intermediate 2 (Yield 1.30 g). GC (METHOD 1): $t_R$=11.59 min; Mass spectrum (EI$^+$): m/z=237 [M]$^+$, e.e. 98% by chiral HPLC (Column: Daicel Chiralpak OJ-H, 4.6×250 mm, 5 μm Mobile phase: hexane:ethanol 95:5, 1 mL/min, 25° C.) $t_R$=37.52 min.

Step 2: (S)-4-Bromo-1-(tert-butyl-dimethyl-silanyloxy)-indan-5-carbonitrile (S)-4-Bromo-1-hydroxy-indan-5-carbonitrile (0.90 g, 3.78 mmol), imidazole (0.64 g, 9.45 mmol) and tert-butyldimethylchlorosilane (0.80 g, 5.29 mmol) are suspended in dry N,N-dimethylformamide and stirred at room temperature for 3 hours. The mixture is diluted with water and extracted with ethyl acetate. The organic extracts are dried and the solvent removed to give the crude product which is used directly in the next step (Yield 1.20 g).

Step 3: (S)-1-(tert-Butyl-dimethyl-silanyloxy)-4-(6-chloro-pyridin-3-ylmethyl)-indan-5-carbonitrile (S)-4-Bromo-1-(tert-butyl-dimethyl-silanyloxy)-indan-5-carbonitrile (crude, 1.20 g) is suspended in dry tetrahydrofuran (3 mL) and (2-chloro-5-pyridine)methyl zinc chloride (0.5 M in tetrahydrofuran, 22.9 mL, 11.44 mL) is added. The mixture is degassed with a flow of nitrogen then tetrakis(triphenylphoshine)palladium(0) is added and the mixture stirred at 60° C. for 6 hours. The solution is diluted with 10% aqueous ammonium chloride solution and extracted with ethyl acetate. The organic extracts are dried and the solvent removed and the residue is purified by flash chromatography (0-50% ethyl acetate in cyclohexane) to give the title compound (Yield 0.14 g). LC (METHOD 6): $t_R$=1.01 min; Mass spectrum (ES$^+$): m/z=399 [M+H]$^+$.

Step 4: (S)-4-(6-Chloro-pyridin-3-ylmethyl)-1-hydroxy-indan-5-carbonitrile (S)-1-(tert-Butyl-dimethyl-silanyloxy)-4-(6-chloro-pyridin-3-ylmethyl)-indan-5-carbonitrile (130 mg, 0.33 mmol) is suspended in dry tetrahydrofuran (5 mL) and cooled in an ice bath. Tetrabutylammonium fluoride (1 M in tetrahydrofuran, 0.65 mL, 0.65 mmol) is added, the mixture allowed to warm to room temperature and stirred for 3 hours. The mixture is concentrated under vacuum, diluted with ethyl acetate and washed with saturated ammonium chloride solution. The organic phase is evaporated to give crude title compound which is used directly in the next step (Yield 143 mg). LC (METHOD 6): $t_R$=0.47 min; Mass spectrum (ES$^+$): m/z=285 [M+H]$^+$.

Step 5: (1S,2S)-2-{4-[(R)-4-(6-Chloro-pyridin-3-ylmethyl)-5-cyano-indan-1-yloxy]-phenyl}-cyclopropanecarboxylic acid ethyl ester The title compound prepared in analogy with the procedure used for the preparation of Intermediate 3 from (S)-4-(6-chloro-pyridin-3-ylmethyl)-1-hydroxy-indan-5-carbonitrile (80 mg, 0.28 mmol) and (1S,2S)-2-(4-hydroxy-phenyl)-cyclopropanecarboxylic acid ethyl ester (Intermediate 1, 116 mg, 0.56 mmol). The product was obtained as an impure mixture (Yield 315 mg). LC (METHOD 5): $t_R$=1.47 min; Mass spectrum (ES$^+$): m/z=473 [M+H]$^+$.

Intermediate 57

2-(4-Hydroxy-phenyl)-trans-cyclopropanecarboxylic acid ethyl ester

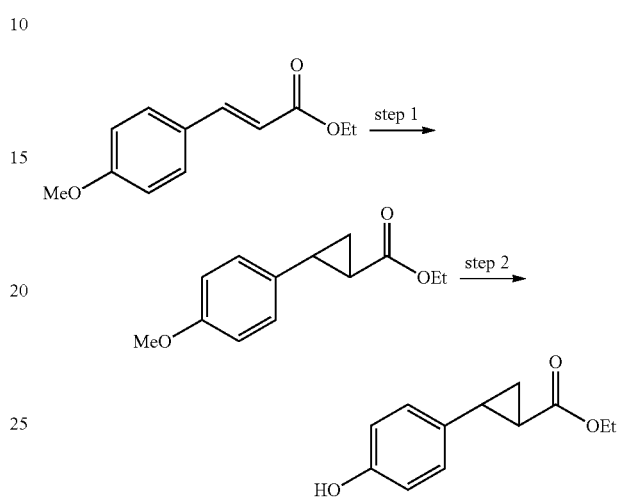

Step 1: 2-(4-Methoxy-phenyl)-trans-cyclopropanecarboxylic acid ethyl ester

Trimethylsulfoxonium iodide (14.15 g, 63 mmol) is suspended in dry dimethylsulfoxide (126 mL) and sodium hydride (60% in mineral oil, 2.52 g, 63 mmol) is added. The mixture is stirred for 40 minutes and then a solution of 4-methoxycinnamic acid ethyl ester (5 g, 24.2 mmol) in dry dimethylsulfoxide (64 mL) is added and the mixture stirred for 3 hours at room temperature. The mixture is diluted with water and extracted with ethyl acetate, the organic phase is dried by passing through a phase separator and the solvent is removed under vacuum. The residue is purified by flash chromatography (10% ethyl acetate in cyclohexane) to give the title compound (yield 1.43 g). LC (METHOD 11): $t_R$=7.74 min; Mass spectrum (ESI$^+$): m/z=221 [M+H]$^+$.

Step 2: 2-(4-Hydroxy-phenyl)-trans-cyclopropanecarboxylic acid ethyl ester 2-(4-Methoxy-phenyl)-trans-cyclopropanecarboxylic acid ethyl ester (1.43 g, 6.51 mmol) is dissolved in dry dichloromethane (30 mL) and cooled to −78° C. Boron tribromide solution (1 M in dichloromethane, 7.81 mL, 7.81 mmol) is added dropwise then the mixture is allowed to warm to −20° C. and stirred overnight at −20° C. Ethanol (3 mL) is added and the mixture warmed to room temperature then diluted with saturated aqueous sodium bicarbonate solution. The phases are separated and the aqueous phase extracted with dichloromethane. The combined organic phases are dried through a phase separator and the solvent removed under vacuum. The residue is purified by flash chromatography (10% ethyl acetate in cyclohexane) and then crystallized from 10% ethyl acetate in cyclohexane to give the title compound (yield 0.58 g). LC (METHOD 11): $t_R$=6.25 min; Mass spectrum (ESI$^+$): m/z=248 [M+H+MeCN]+.

Intermediate 58

(S)-4-Benzenesulfonyl-indan-1-ol

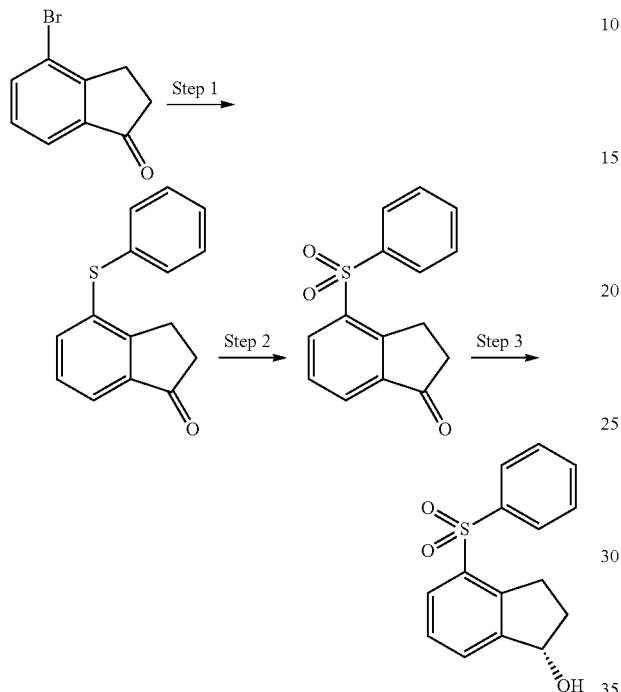

Step 1: 4-Phenylsulfanyl-indan-1-one

4-Bromo-1-indanone (0.30 g), thiophenol (0.15 mL), tris (dibenzylideneacetone)palladium(0) (0.13 g), 4,5-bis(diphenylphosphino)-9,9-dimethylxanthene (0.082 g) and N,N-diisopropylethylamine (0.98 mL) are stirred in dioxane (1 mL) for 2 hours under microwave irradiation at 120° C. After removal of the solvent under vacuum the residue is purified by column chromatography (silica gel, cyclohexane:ethyl acetate 6:4) to give the desired material (0.34 g). LC (METHOD 5): $t_R$=1.28 min; Mass spectrum: m/z=241 [M+H]$^+$.

Step 2: 4-Benzenesulfonyl-indan-1-one

The material from Step 1 (0.34 g) is allowed to react with 3-chloroperoxybenzoic acid (0.73 g) in dichloromethane (5 mL) with stirring for 1 hour. The mixture is diluted with dichloromethane, 5% aqueous sodium sulfite solution is added and stirred vigorously for 10 minutes. The phases are separated, the organic phase washed with NaOH solution (0.2 M), dried and the solvent removed to give the desired material (0.39 g). LC (METHOD 5): $t_R$=0.98 min; Mass spectrum: m/z=290 [M+NH$_4$]$^+$.

Step 3: (S)-4-Benzenesulfonyl-indan-1-ol

Under nitrogen a solution of the material from Step 2 (0.39 g) in CH$_2$Cl$_2$ (10 mL) is added dropwise to a stirred mixture of formic acid (0.20 mL) and triethylamine (0.61 mL) with cooling in an ice-bath. Chloro([1S,2S)-(−)-2-amino-1,2-diphenylethyl](4-toluenesulfonyl)amido)(mesitylene)ruthenium(II) (26 mg) is added and the reaction mixture stirred at 0° C. for 3 hours. Water is added and the resulting mixture extracted twice with ethyl acetate. The combined organic layers are washed (saturated aqueous NaHCO3), dried and purified by column chromatography (silica gel, cyclohexane: ethyl acetate gradient 100:0 to 50:50), to obtain the desired material (0.39 g). LC (METHOD 14): $t_R$=0.83 min; Mass spectrum: m/z=257 [M+H−H$_2$O]$^+$.

Intermediate 59

(S)-4-(2,6-Dimethylbenzenesulfonyl)-indan-1-ol

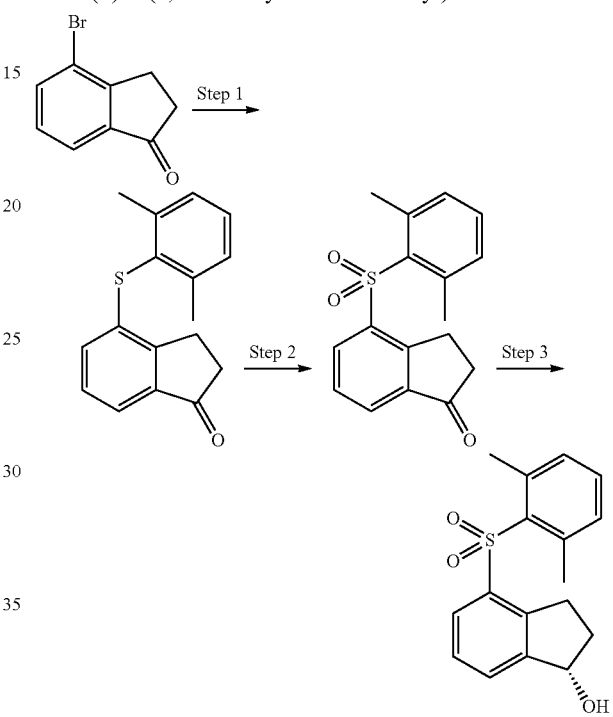

The title compound is prepared in analogy to the preparation of Intermediate 58 using 2,6-dimethylthiophenol in Step 1. The product from step 2 is purified by flash chromatography (0-50% ethyl acetate in cyclohexane). LC (METHOD 5): $t_R$=1.03 min; Mass spectrum: m/z=285 [M+H—H$_2$O]$^+$.

Intermediate 60

(S)-4-Benzenesulfinyl-indan-1-ol

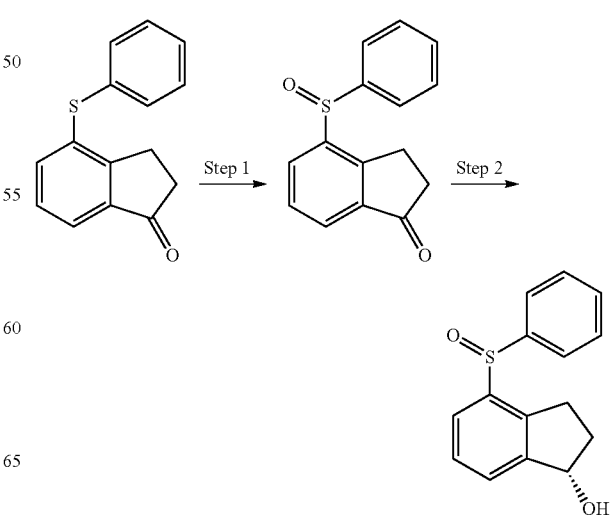

Step 1: 4-Benzenesulfinyl-indan-1-one

The title compound is prepared in analogy to Step 2 in the preparation of Intermediate 58, but using 1 molar equivalent of 3-chloroperoxybenzoic acid. LC (METHOD 4): $t_R$=0.87 min; Mass spectrum: m/z=257 [M+H]$^+$.

Step 2: (S)-4-Benzenesulfinyl-indan-1-ol

The title compound is prepared in analogy to Step 3 in the preparation of Intermediate 58. LC (METHOD 5): $t_R$=0.79 min; Mass spectrum: m/z=259 [M+H]$^+$.

Intermediate 61

4-((S)-1-Hydroxy-indane-4-sulfonyl)-3,5-dimethyl-benzonitrile

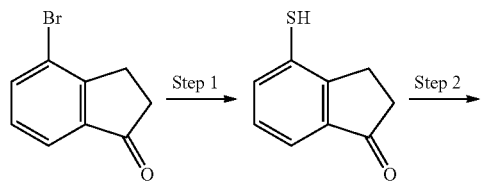

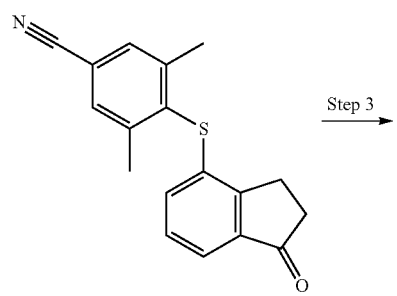

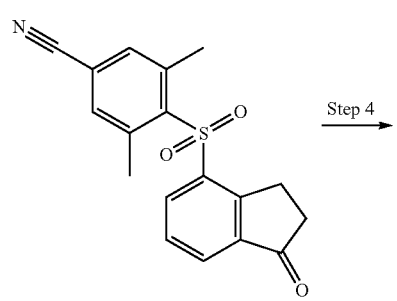

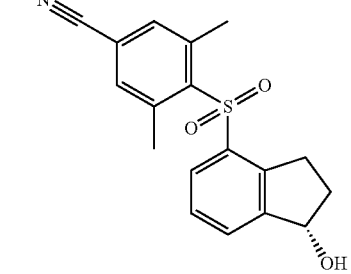

Step 1: 4-Mercapto-indan-1-one

4-Bromo-indanone (500 mg, 2.37 mmol), 4,5-bis(diphenylphosphino)-9,9-dimethylxanthene (137 mg, 0.24 mmol), thioacetate (541 mg, 4.74 mmol) and diisopropylethylamine (1.64 mL, 5.69 mmol) are dissolved in 1,4-dioxane (2 mL). The mixture is degassed with N$_2$ and tris(dibenzylideneacetone)palladium(0) (217 mg, 0.24 mmol) is added and heated under microwave irradiation at 120° C. for 2 hours. The solution is concentrated under vacuum. The crude product obtained is purified by flash chromatography (10-80% ethyl acetate in cyclohexane) to give the title compound (Yield: 210 mg). LC (METHOD 5): $t_R$=0.89 min; Mass spectrum (ES−): m/z=163 [M−H]$^−$.

Step 2: 3,5-Dimethyl-4-(1-oxo-indan-4-ylsulfanyl)-benzonitrile

4-Mercapto-indan-1-one (Step 1, 210 mg, 1.28 mmol), 4,5-bis(diphenylphosphino)-9,9-dimethylxanthene (74 mg, 0.13 mmol), 4-bromo-3,5-dimethyl-benzonitrile (269 mg, 1.28 mmol) and diisopropylethylamine (0.88 mL, 5.1 mmol) are dissolved in 1,4-dioxane (2 mL). The mixture is degassed with N$_2$, tris(dibenzylideneacetone)palladium(0) (117 mg, 0.13 mmol) added and heated under microwave irradiation at 120° C. for 2 hours. The solution is concentrated under vacuum. The crude product obtained is purified by flash chromatography (10-80% ethyl acetate in cyclohexane) to give the title compound (Yield: 330 mg). LC (METHOD 5): $t_R$=1.36 min; Mass spectrum (ES$^+$): m/z=294 [M+H]$^+$.

Step 3: 3,5-Dimethyl-4-(1-oxo-indane-4-sulfonyl)-benzonitrile

Carried out in analogy to Step 2 in the preparation of Intermediate 58 (Yield 150 mg). LC (METHOD 4): $t_R$=1.13 min; Mass spectrum (ES$^+$): m/z=326 [M+H]$^+$.

Step 4: 4-((S)-1-Hydroxy-indane-4-sulfonyl)-3,5-dimethyl-benzonitrile

Carried out in analogy to Step 3 in the preparation of Intermediate 58 (Yield 90 mg). LC (METHOD 5): $t_R$=1.03 min; Mass spectrum (ES$^+$): m/z=345 [M+NH$_4$]$^+$.

The intermediates in the following table are prepared in analogy with the procedure used for the preparation of Intermediate 3 from the starting intermediates described:

| Intermediate | Structure | Starting intermediates | Yield | Analysis |
|---|---|---|---|---|
| 62 | 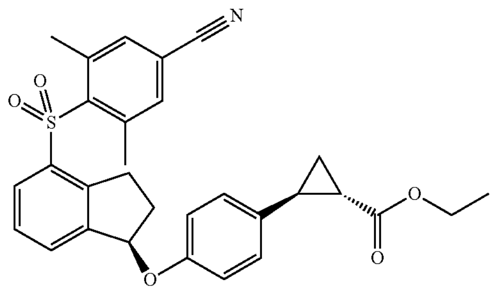 [SMILES: CCOC(=O)[C@H]1C[C@@H]1c1ccc(O[C@@H]2CCc3c2cccc3S(=O)(=O)c2c(C)cc(C#N)cc2C)cc1] | Intermediate 1 (100 mg) and Intermediate 61 (175 mg) | 242 mg | LC (METHOD 5): $t_R$ = 1.49 min; Mass spectrum (ES−): m/z = 514 [M − H]⁻. |
| 63 | 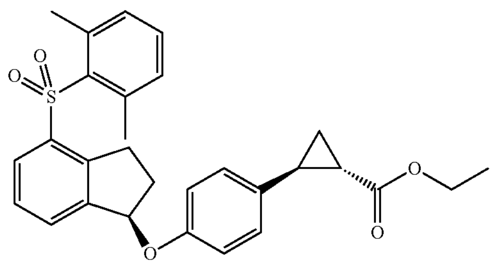 [SMILES: CCOC(=O)[C@H]1C[C@@H]1c1ccc(O[C@@H]2CCc3c2cccc3S(=O)(=O)c2c(C)cccc2C)cc1] | Intermediate 1 (111 mg) and Intermediate 59 (164 mg) | 142 mg | LC (METHOD 10): $t_R$ = 11.05 min; Mass spectrum (ES⁺): m/z = 490 [M − H]⁺. |
| 64 | 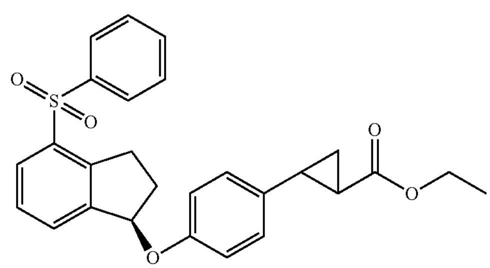 [SMILES: CCOC(=O)C1CC1c1ccc(O[C@@H]2CCc3c2cccc3S(=O)(=O)c2ccccc2)cc1] | Intermediate 57 (165 mg) and Intermediate 58 (220 mg) | 110 mg | LC (METHOD 5): $t_R$ = 1.44 min; Mass spectrum (ES⁺): m/z = 480 [M + NH₄]⁺. |
| 65 | 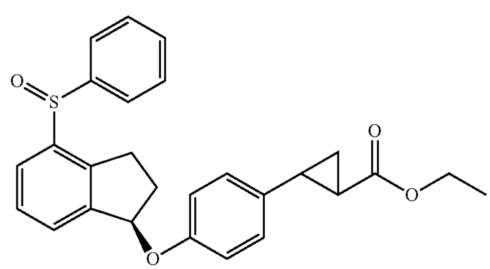 [SMILES: CCOC(=O)C1CC1c1ccc(O[C@@H]2CCc3c2cccc3S(=O)c2ccccc2)cc1] | Intermediate 57 (160 mg) and Intermediate 60 (200 mg) | 1 g (crude) | LC (METHOD 5): $t_R$ = 1.38 min; Mass spectrum (ES⁺): m/z = 447 [M + H]⁺ |

Synthesis of Examples

General Procedure

Hydrolysis of Ester Intermediates to the Corresponding Carboxylic Acids

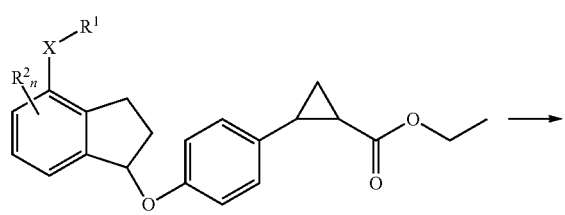

→

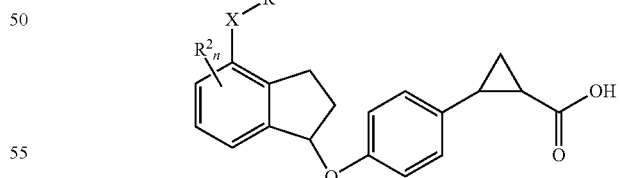

The ester intermediate is suspended in a suitable solvent and treated with a hydroxide base in aqueous solution. The mixture is stirred until the hydrolysis is complete then concentrated under vacuum, acidified with dilute aqueous acid (e.g. 1 M HCl or 10% citric acid) and the product collected by filtration or extracted with ethyl acetate or dichloromethane. The organic extracts are washed with water and brine, dried and the solvent removed. If necessary the residue is purified by flash chromatography on silica gel and/or reverse phase (C18) or by preparative HPLC or by preparative TLC to give the title compound.

Further details for the preparation of each example are given in the table below

| Ex | Structure | Starting material | Solvent & Base | Purification & Yield | Analysis |
|---|---|---|---|---|---|
| 1 | 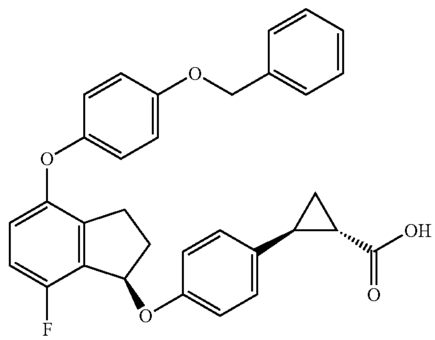 [SMILES: O=C(O)[C@H]1C[C@@H]1c1ccc(O[C@@H]2CCc3c(Oc4ccc(OCc5ccccc5)cc4)ccc(F)c32)cc1] | Intermediate 6 (78 mg) | Ethanol (2 mL) dioxane (2 mL) NaOH aq. (1M, 2 mL) | Reverse phase (10-90% acetonitrile in water), 44 mg | LC (METHOD 12): $t_R$ = 3.94 min; Mass spectrum (ES−): m/z = 509 [M − H]$^-$. |
| 2 | 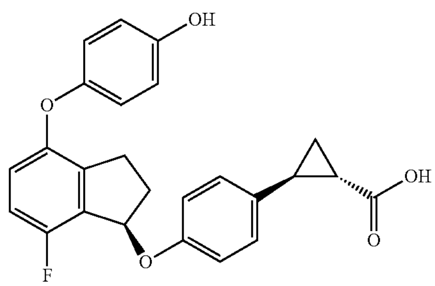 [SMILES: O=C(O)[C@H]1C[C@@H]1c1ccc(O[C@@H]2CCc3c(Oc4ccc(O)cc4)ccc(F)c32)cc1] | Intermediate 7 (35 mg) | Ethanol (2 mL) NaOH aq. (1M, 1 mL) | Reverse phase (10-90% acetonitrile in water), 25 mg | LC (METHOD 12): $t_R$ = 2.81 min; Mass spectrum (ES−): m/z = 419 [M − H]$^-$. |
| 3 | 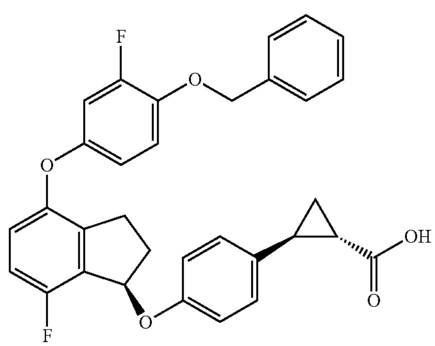 [SMILES: O=C(O)[C@H]1C[C@@H]1c1ccc(O[C@@H]2CCc3c(Oc4ccc(OCc5ccccc5)c(F)c4)ccc(F)c32)cc1] | Intermediate 8 | Ethanol (2 mL) NaOH aq. (1M, 1 mL) | No purification, 52 mg | LC (METHOD 12): $t_R$ = 4.11 min; Mass spectrum (ES−): m/z = 527 [M − H]$^-$. |
| 4 | 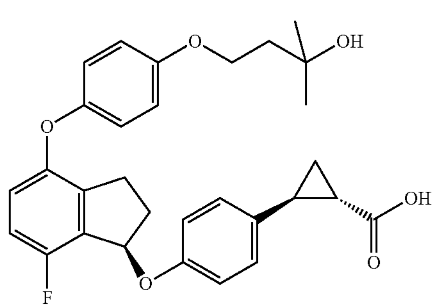 [SMILES: CC(C)(O)CCOc1ccc(Oc2ccc(F)c3c2CC[C@H]3Oc2ccc([C@H]3C[C@@H]3C(=O)O)cc2)cc1] | Intermediate 11 (60 mg) | Dioxane (2 mL) NaOH aq. (1M, 2 mL) | Reverse phase (10-100% acetonitrile in water), 35 mg | LC (METHOD 12): $t_R$ = 3.07 min; Mass spectrum (ES−): m/z = 507 [M − H]$^-$. |

| Ex | Structure | Starting material | Solvent & Base | Purification & Yield | Analysis |
|---|---|---|---|---|---|
| 5 | 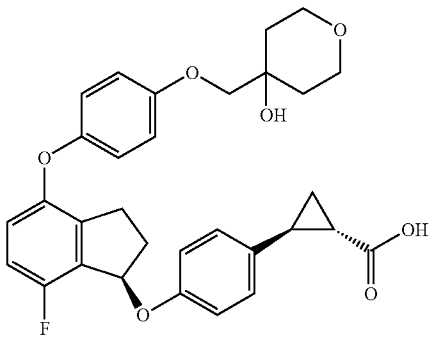 [SMILES: O=C(O)[C@H]1C[C@@H]1c1ccc(O[C@@H]2CCc3c(Oc4ccc(OCC5(O)CCOCC5)cc4)ccc(F)c32)cc1] | Intermediate 12 (69 mg) | Ethanol (2 mL) NaOH aq. (1M, 1 mL) | No purification, 60 mg | LC (METHOD 12): $t_R$ = 2.79 min; Mass spectrum (ES−): m/z = 533 $[M − H]^-$. |
| 6 | 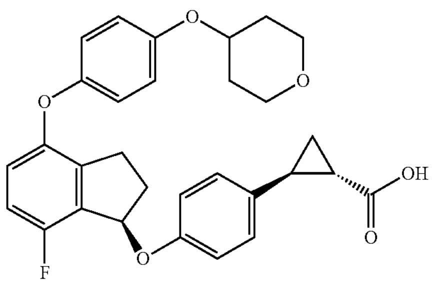 [SMILES: O=C(O)[C@H]1C[C@@H]1c1ccc(O[C@@H]2CCc3c(Oc4ccc(OC5CCOCC5)cc4)ccc(F)c32)cc1] | Intermediate 13 (44 mg) | Ethanol (2 mL) NaOH aq. (1M, 2 mL) | No purification, 41 mg | LC (METHOD 9): $t_R$ = 2.54 min; Mass spectrum (ES−): m/z = 503 $[M − H]^-$. |
| 7 | 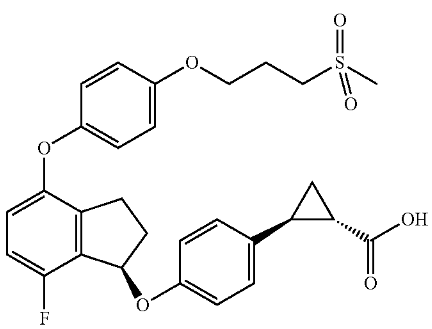 [SMILES: CS(=O)(=O)CCCOc1ccc(Oc2ccc(F)c3c2CC[C@H]3Oc2ccc([C@H]3C[C@@H]3C(=O)O)cc2)cc1] | Intermediate 14 (40 mg) | Ethanol (2 mL) NaOH aq. (1M, 1 mL) | Reverse phase (10-90% acetonitrile in water), 8 mg | LC (METHOD 12): $t_R$ = 3.03 min; Mass spectrum (ES+): m/z = 541 $[M + H]^+$. |
| 8 | 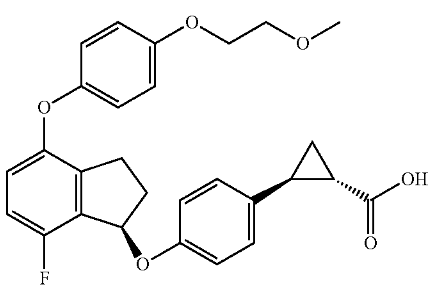 [SMILES: COCCOc1ccc(Oc2ccc(F)c3c2CC[C@H]3Oc2ccc([C@H]3C[C@@H]3C(=O)O)cc2)cc1] | Intermediate 15 (155 mg) | Ethanol (2 mL) NaOH aq. (1M, 1 mL) | No purification, 128 mg | LC (METHOD 12): $t_R$ = 3.44 min; Mass spectrum (ES−): m/z = 477 $[M − H]^-$. |
| 9 | 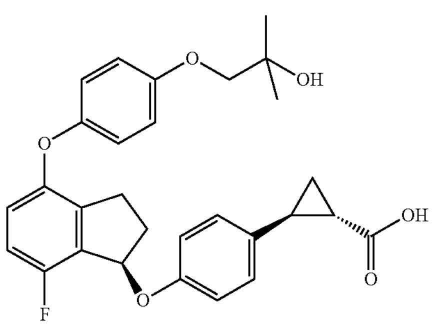 [SMILES: CC(C)(O)COc1ccc(Oc2ccc(F)c3c2CC[C@H]3Oc2ccc([C@H]3C[C@@H]3C(=O)O)cc2)cc1] | Intermediate 16 (78 mg) | Ethanol (2 mL) NaOH aq. (1M, 1 mL) | Reverse phase (10-90% acetonitrile in water), 40 mg | LC (METHOD 12): $t_R$ = 3.33 min; Mass spectrum (ES−): m/z = 491 $[M − H]^-$. |

-continued

| Ex | Structure | Starting material | Solvent & Base | Purification & Yield | Analysis |
|---|---|---|---|---|---|
| 10 | 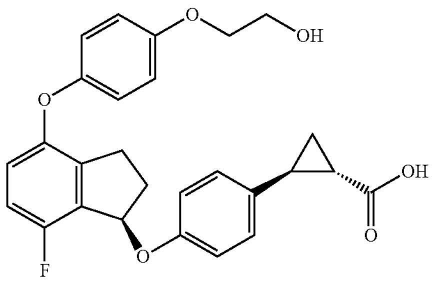 [SMILES: O=C(O)[C@H]1C[C@@H]1c1ccc(O[C@@H]2CCc3c(Oc4ccc(OCCO)cc4)ccc(F)c32)cc1] | Intermediate 17 (85 mg) | Ethanol (2 mL) NaOH aq. (1M, 2 mL) | No purification, 64 mg | LC (METHOD 12): $t_R$ = 2.94 min; Mass spectrum (ES−): m/z = 463 [M − H]⁻. |
| 11 | 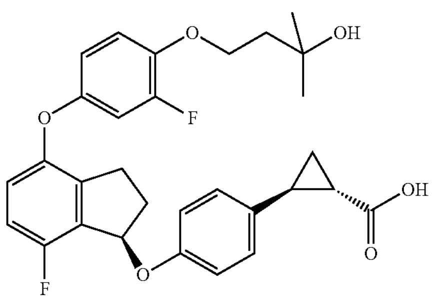 [SMILES: CC(C)(O)CCOc1ccc(Oc2ccc(F)c3c2CC[C@H]3Oc2ccc([C@H]3C[C@@H]3C(=O)O)cc2)cc1F] | Intermediate 18 (150 mg) | Ethanol (10 mL) NaOH aq. (1M, 2 mL) | No purification, 90 mg | LC (METHOD 12): $t_R$ = 3.39 min; Mass spectrum (ES⁺): m/z = 525 [M + H]⁺. |
| 12 | 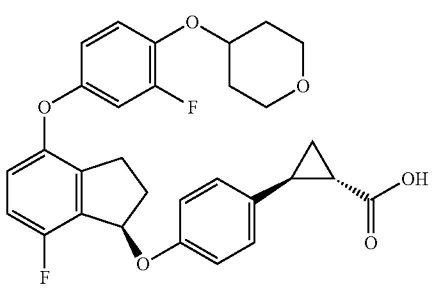 [SMILES: O=C(O)[C@H]1C[C@@H]1c1ccc(O[C@@H]2CCc3c(Oc4ccc(OC5CCOCC5)c(F)c4)ccc(F)c32)cc1] | Intermediate 19 (90 mg) | Ethanol (7 mL) NaOH aq. (1M, 3 mL) | Reverse phase (20-80% acetonitrile in water), 50 mg | LC (METHOD 13): $t_R$ = 7.25 min; Mass spectrum (ES⁺): m/z = 523 [M + H]⁺. |
| 13 | 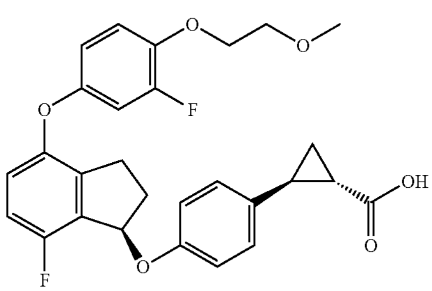 [SMILES: COCCOc1ccc(Oc2ccc(F)c3c2CC[C@H]3Oc2ccc([C@H]3C[C@@H]3C(=O)O)cc2)cc1F] | Intermediate 20 (60 mg) | Ethanol (2 mL) NaOH aq. (1M, 1 mL) | No purification, 32 mg | LC (METHOD 12): $t_R$ = 3.55 min; Mass spectrum (ES−): m/z = 495 [M − H]⁻. |
| 14 | 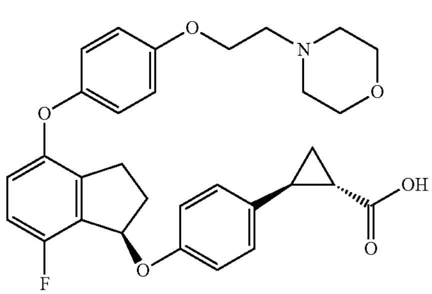 [SMILES: O=C(O)[C@H]1C[C@@H]1c1ccc(O[C@@H]2CCc3c(Oc4ccc(OCCN5CCOCC5)cc4)ccc(F)c32)cc1] | Intermediate 21 (175 mg) | Ethanol (2 mL) tetrahydrofuran (2 mL) NaOH aq. (1M, 2 mL) | Reverse phase (10-90% acetonitrile in water), 25 mg | LC (METHOD 3): $t_R$ = 2.61 min; Mass spectrum (ES⁺): m/z = 534 [M + H]⁺. |

-continued

| Ex | Structure | Starting material | Solvent & Base | Purification & Yield | Analysis |
|---|---|---|---|---|---|
| 15 | 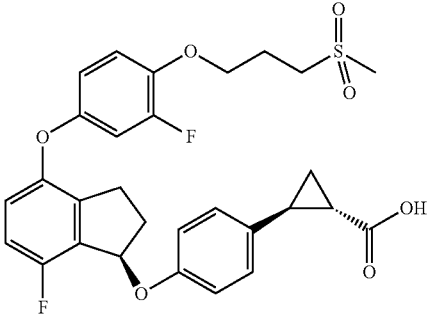 [SMILES: CS(=O)(=O)CCCOc1ccc(Oc2ccc(F)c3c2CC[C@H]3Oc2ccc([C@H]3C[C@@H]3C(=O)O)cc2)cc1F] | Intermediate 22 (50 mg) | Ethanol (2 mL) NaOH aq. (1M, 1 mL) | Reverse phase (20-80% acetonitrile in water), 14 mg | LC (METHOD 13): $t_R$ = 6.48 min; Mass spectrum (ES$^+$): m/z = 559 [M + H]$^+$. |
| 16 | 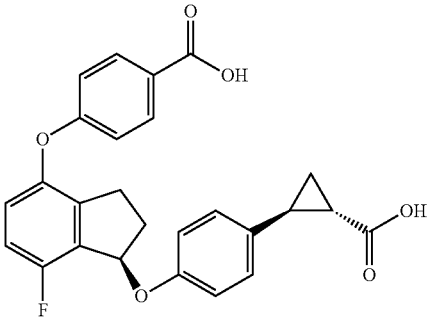 [SMILES: O=C(O)c1ccc(Oc2ccc(F)c3c2CC[C@H]3Oc2ccc([C@H]3C[C@@H]3C(=O)O)cc2)cc1] | Intermediate 23 (44 mg) | Tetrahydrofuran (4 mL), methanol (4 mL), water (4 mL), LiOH (38 mg) | Flash chromatography (CH$_2$Cl$_2$/ MeOH/AcOH 9:0.1:0.1), 38 mg | LC (METHOD 12): $t_R$ = 2.23 min; Mass spectrum (ES−): m/z = 447 [M − H]$^−$. |
| 17 | 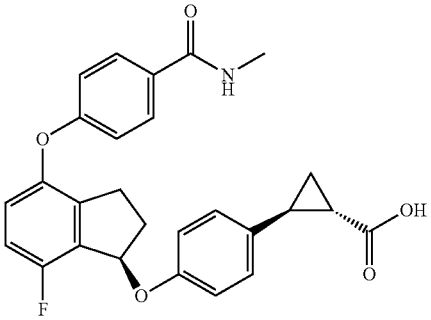 [SMILES: CNC(=O)c1ccc(Oc2ccc(F)c3c2CC[C@H]3Oc2ccc([C@H]3C[C@@H]3C(=O)O)cc2)cc1] | Intermediate 24 (98 mg) | Tetrahydrofuran (3 mL), methanol (3 mL), water (3 mL), LiOH (42 mg) | Collected as precipitated solid, 85 mg | LC (METHOD 12): $t_R$ = 3.62 min; Mass spectrum (ES$^+$): m/z = 462 [M + H]$^+$. |
| 18 | 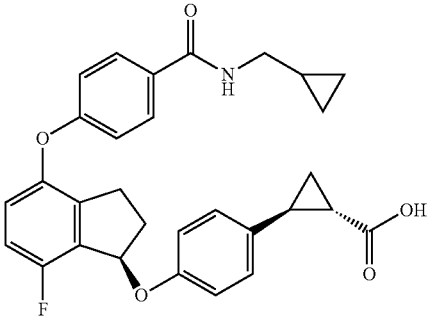 [SMILES: O=C(NCC1CC1)c1ccc(Oc2ccc(F)c3c2CC[C@H]3Oc2ccc([C@H]3C[C@@H]3C(=O)O)cc2)cc1] | Intermediate 25 (92 mg) | Tetrahydrofuran (3 mL), methanol (3 mL), water (3 mL), LiOH (36 mg) | Collected as precipitated solid, 85 mg | LC (METHOD 12): $t_R$ = 3.04 min; Mass spectrum (ES$^+$): m/z = 502 [M + H]$^+$. |

-continued

| Ex | Structure | Starting material | Solvent & Base | Purification & Yield | Analysis |
|---|---|---|---|---|---|
| 19 | 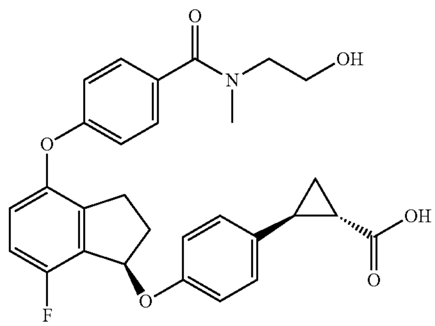 [SMILES: CN(CCO)C(=O)c1ccc(Oc2ccc(F)c3c2CC[C@H]3Oc2ccc([C@H]3C[C@@H]3C(=O)O)cc2)cc1] | Intermediate 26 (93 mg) | Tetrahydrofuran (3 mL), methanol (3 mL), water (3 mL), LiOH (36 mg) | Preparative TLC (CH$_2$Cl$_2$/MeOH/AcOH 9:0.1:0.1), 21 mg | LC (METHOD 3): $t_R$ = 3.42 min; Mass spectrum (ES$^+$): m/z = 506 [M + H]$^+$. |
| 20 | 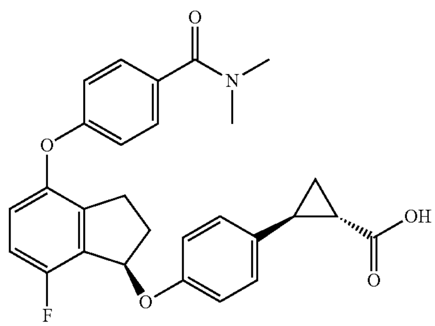 [SMILES: CN(C)C(=O)c1ccc(Oc2ccc(F)c3c2CC[C@H]3Oc2ccc([C@H]3C[C@@H]3C(=O)O)cc2)cc1] | Intermediate 27 (96 mg) | Tetrahydrofuran (3 mL), methanol (3 mL), water (3 mL), LiOH (40 mg) | Collected as precipitated solid, 85 mg | LC (METHOD 12): $t_R$ = 2.80 min; Mass spectrum (ES$^+$): m/z = 476 [M + H]$^+$. |
| 21 | 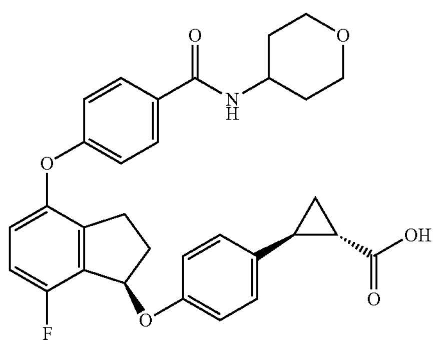 [SMILES: O=C(NC1CCOCC1)c1ccc(Oc2ccc(F)c3c2CC[C@H]3Oc2ccc([C@H]3C[C@@H]3C(=O)O)cc2)cc1] | Intermediate 28 (103 mg) | Tetrahydrofuran (3 mL), methanol (3 mL), water (3 mL), LiOH (38 mg) | Collected as precipitated solid, 86 mg | LC (METHOD 12): $t_R$ = 2.75 min; Mass spectrum (ES$^+$): m/z = 532 [M + H]$^+$. |
| 22 | 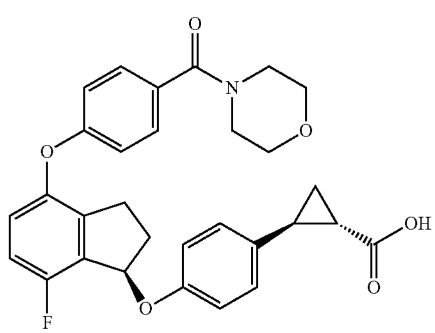 [SMILES: O=C(O)[C@H]1C[C@@H]1c1ccc(O[C@@H]2CCc3c(Oc4ccc(C(=O)N5CCOCC5)cc4)ccc(F)c32)cc1] | Intermediate 29 (42 mg) | Tetrahydrofuran (3 mL), methanol (3 mL), water (3 mL), LiOH (17 mg) | Collected as precipitated solid, 36 mg | LC (METHOD 12): $t_R$ = 2.85 min; Mass spectrum (ES$^+$): m/z = 518 [M + H]$^+$. |

-continued

| Ex | Structure | Starting material | Solvent & Base | Purification & Yield | Analysis |
|---|---|---|---|---|---|
| 23 | 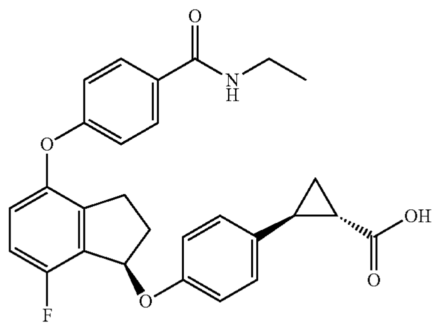 [SMILES: CCNC(=O)c1ccc(Oc2ccc(F)c3c2CC[C@H]3Oc2ccc([C@H]3C[C@@H]3C(=O)O)cc2)cc1] | Intermediate 30 (33 mg) | Tetrahydrofuran (3 mL), methanol (3 mL), water (3 mL), LiOH (15 mg) | Collected as precipitated solid, 28 mg | LC (METHOD 12): $t_R$ = 2.93 min; Mass spectrum (ES+): m/z = 476 [M + H]+. |
| 24 | 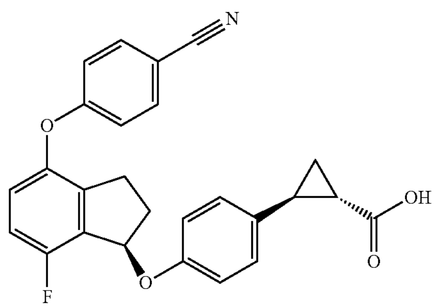 [SMILES: N#Cc1ccc(Oc2ccc(F)c3c2CC[C@H]3Oc2ccc([C@H]3C[C@@H]3C(=O)O)cc2)cc1] | Intermediate 31 (62 mg) | Tetrahydrofuran (3 mL), methanol (3 mL), water (3 mL), LiOH (16 mg) | Flash chromatography ($CH_2Cl_2$/MeOH/AcOH 9:0.1:0.1) 48 mg | LC (METHOD 12): $t_R$ = 3.27 min; Mass spectrum (ES−): m/z = 428 [M − H]−. |
| 25 | 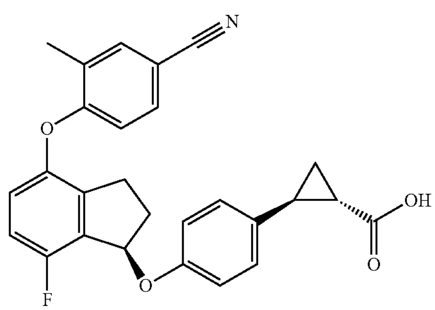 [SMILES: Cc1cc(C#N)ccc1Oc1ccc(F)c2c1CC[C@H]2Oc1ccc([C@H]2C[C@@H]2C(=O)O)cc1] | Intermediate 32 (46 mg) | Tetrahydrofuran (3 mL), methanol (3 mL), water (3 mL), LiOH (13 mg) | Flash chromatography ($CH_2Cl_2$/MeOH/AcOH 9:0.2:0.2) 36 mg | LC (METHOD 12): $t_R$ = 3.54 min; Mass spectrum (ES+): m/z = 444 [M + H]+. |
| 26 | 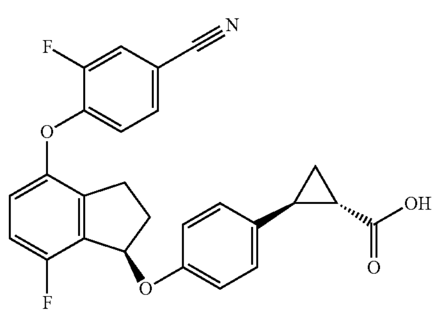 [SMILES: N#Cc1ccc(Oc2ccc(F)c3c2CC[C@H]3Oc2ccc([C@H]3C[C@@H]3C(=O)O)cc2)c(F)c1] | Intermediate 33 (110 mg) | Tetrahydrofuran (2 mL), methanol (2 mL), water (2 mL), LiOH (29 mg) | Flash chromatography ($CH_2Cl_2$/MeOH/AcOH 9:0.1:0.1) 60 mg | LC (METHOD 12): $t_R$ = 3.40 min; Mass spectrum (ES+): m/z = 446 [M + H]+. |
| 27 | 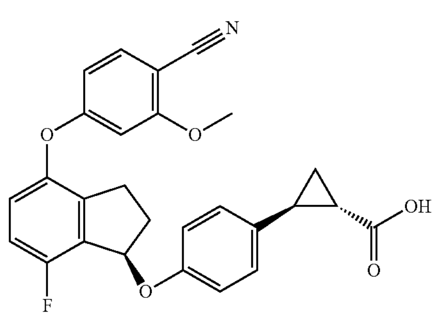 [SMILES: COc1cc(Oc2ccc(F)c3c2CC[C@H]3Oc2ccc([C@H]3C[C@@H]3C(=O)O)cc2)ccc1C#N] | Intermediate 34 (250 mg) | Ethanol (5 mL) NaOH aq. (2M, 0.7 mL) | Reverse phase (10-80% acetonitrile in water), 122 mg | LC (METHOD 9): $t_R$ = 2.43 min; Mass spectrum (ES−): m/z = 458 [M − H]−. |

-continued

| Ex | Structure | Starting material | Solvent & Base | Purification & Yield | Analysis |
|---|---|---|---|---|---|
| 28 | 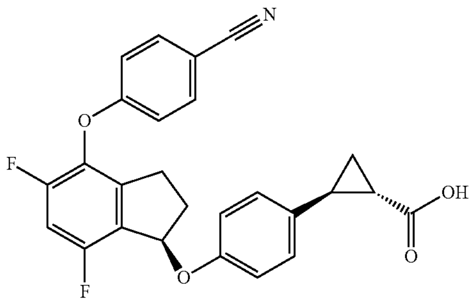 [SMILES: N#Cc1ccc(Oc2c(F)cc(F)c3c2CC[C@H]3Oc2ccc([C@H]3C[C@@H]3C(=O)O)cc2)cc1] | Intermediate 36 (40 mg) | Dioxane (2 mL), water (0.2 mL), LiOH (10 mg) | Preparative HPLC, 12 mg | LC (METHOD 12): $t_R$ = 3.17 min; Mass spectrum (ES−): m/z = 446 [M − H]⁻. |
| 29 | 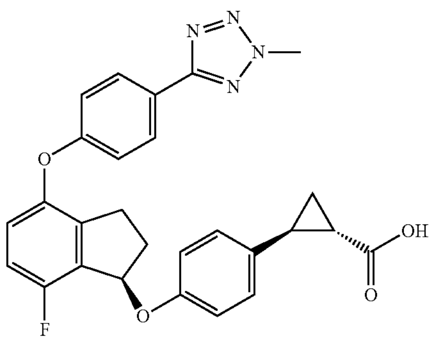 [SMILES: Cn1nnc(-c2ccc(Oc3ccc(F)c4c3CC[C@H]4Oc3ccc([C@H]4C[C@@H]4C(=O)O)cc3)cc2)n1] | Intermediate 45 (177 mg) | Tetrahydrofuran (4 mL), methanol (4 mL), water (4 mL), LiOH (71 mg) | Collected as precipitated solid, 136 mg | LC (METHOD 12): $t_R$ = 3.15 min; Mass spectrum (ES⁺): m/z = 487 [M + H]⁺. |
| 30 | 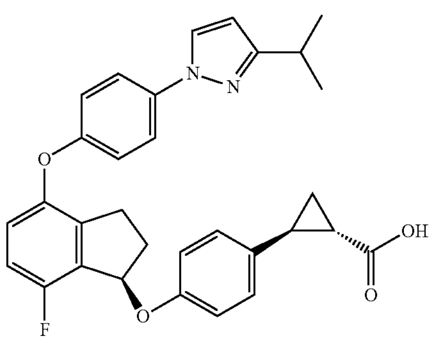 [SMILES: CC(C)c1ccn(-c2ccc(Oc3ccc(F)c4c3CC[C@H]4Oc3ccc([C@H]4C[C@@H]4C(=O)O)cc3)cc2)n1] | Intermediate 46 (48 mg) | Tetrahydrofuran (2 mL), methanol (2 mL), water (2 mL), LiOH (19 mg) | Flash chromatography (CH₂Cl₂/ MeOH/AcOH 9:0.07:0.07) 37 mg | LC (METHOD 12): $t_R$ = 3.91 min; Mass spectrum (ES⁺): m/z = 513 [M + H]⁺. |
| 31 | 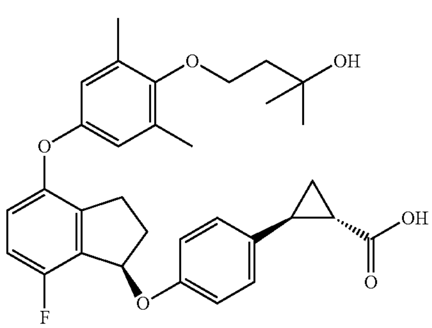 [SMILES: Cc1cc(Oc2ccc(F)c3c2CC[C@H]3Oc2ccc([C@H]3C[C@@H]3C(=O)O)cc2)cc(C)c1OCCC(C)(C)O] | Intermediate 47 (24 mg) | Dioxane (2 mL) NaOH aq. (1M, 2 mL) | Reverse phase (20-80% acetonitrile in water), 9 mg | LC (METHOD 12): $t_R$ = 3.40 min; Mass spectrum (ES−): m/z = 533 [M − H]⁻. |

| Ex | Structure | Starting material | Solvent & Base | Purification & Yield | Analysis |
|---|---|---|---|---|---|
| 32 | 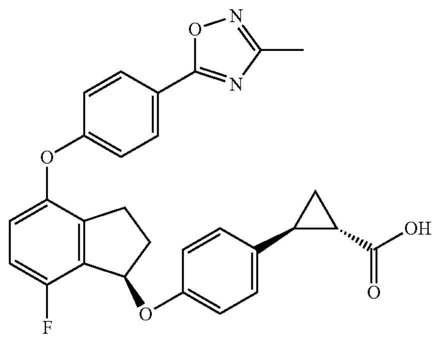 [SMILES: Cc1noc(-c2ccc(Oc3ccc(F)c4c3CC[C@H]4Oc3ccc([C@H]4C[C@@H]4C(=O)O)cc3)cc2)n1] | Intermediate 48 (25 mg) | Dioxane (2 mL) NaOH aq. (1M, 2 mL) | Reverse phase (20-80% acetonitrile in water), 13 mg | LC (METHOD 12): $t_R$ = 3.34 min; Mass spectrum (ES$^+$): m/z = 487 [M + H]$^+$. |
| 33 | 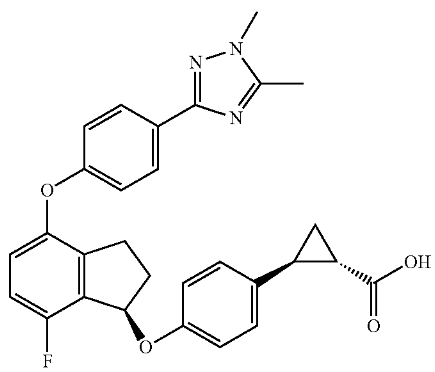 [SMILES: Cc1nc(-c2ccc(Oc3ccc(F)c4c3CC[C@H]4Oc3ccc([C@H]4C[C@@H]4C(=O)O)cc3)cc2)nn1C] | Intermediate 49 (100 mg) | Ethanol (2 mL) NaOH aq. (1M, 1 mL) | Preparative HPLC, 50 mg | LC (METHOD 12): $t_R$ = 2.95 min; Mass spectrum (ES$^+$): m/z = 500 [M + H]$^+$. |
| 34 | 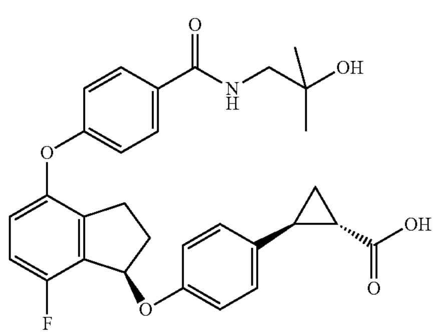 [SMILES: CC(C)(O)CNC(=O)c1ccc(Oc2ccc(F)c3c2CC[C@H]3Oc2ccc([C@H]3C[C@@H]3C(=O)O)cc2)cc1] | Intermediate 50 (100 mg) | Ethanol (2 mL) NaOH aq. (1M, 1 mL) | Reverse phase (20-80% acetonitrile in water), 20 mg | LC (METHOD 9): $t_R$ = 2.10 min; Mass spectrum (ES$^+$): m/z = 520 [M + H]$^+$. |
| 35 | 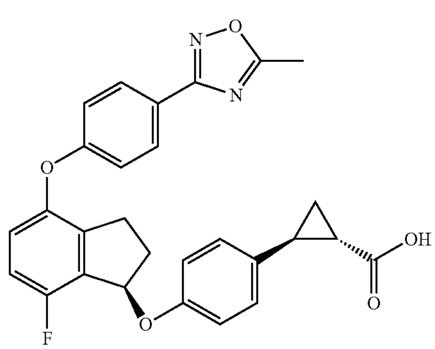 [SMILES: Cc1nc(-c2ccc(Oc3ccc(F)c4c3CC[C@H]4Oc3ccc([C@H]4C[C@@H]4C(=O)O)cc3)cc2)no1] | Intermediate 51 (300 mg, crude) | Ethanol (3 mL) NaOH aq. (1M, 3 mL) | Reverse phase (20-80% acetonitrile in water), 30 mg | LC (METHOD 12): $t_R$ = 3.28 min; Mass spectrum (ES$^+$): m/z = 487 [M + H]$^+$. |

-continued

| Ex | Structure | Starting material | Solvent & Base | Purification & Yield | Analysis |
|---|---|---|---|---|---|
| 36 | 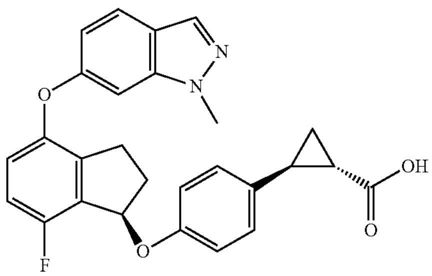 [SMILES: Cn1ncc2ccc(Oc3ccc(F)c4c3CC[C@H]4Oc3ccc([C@H]4C[C@@H]4C(=O)O)cc3)cc21] | Intermediate 52 (156 mg) | Ethanol (2 mL) NaOH aq. (1M, 1 mL) | Reverse phase (10-90% acetonitrile in water), 90 mg | LC (METHOD 3): $t_R$ = 4.06 min; Mass spectrum (ES$^+$): m/z = 459 [M + H]$^+$. |
| 37 | 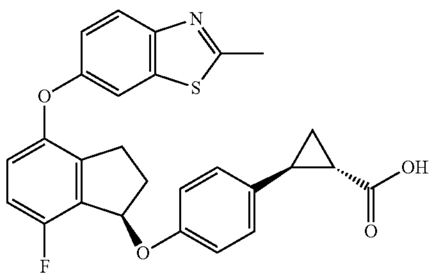 [SMILES: Cc1nc2ccc(Oc3ccc(F)c4c3CC[C@H]4Oc3ccc([C@H]4C[C@@H]4C(=O)O)cc3)cc2s1] | Intermediate 53 (400 mg, crude) | Ethanol (7 mL) NaOH aq. (1M, 2 mL) | Preparative HPLC, 93 mg | LC (METHOD 3): $t_R$ = 4.17 min; Mass spectrum (ES$^+$): m/z = 476 [M + H]$^+$. |
| 38 | 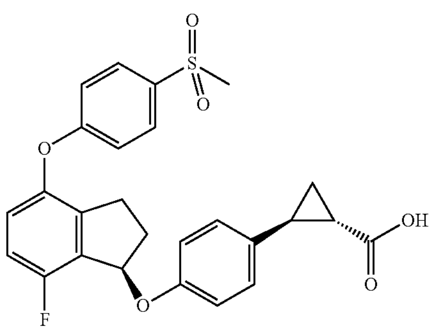 [SMILES: CS(=O)(=O)c1ccc(Oc2ccc(F)c3c2CC[C@H]3Oc2ccc([C@H]3C[C@@H]3C(=O)O)cc2)cc1] | Intermediate 54 (400 mg, crude) | Ethanol (5 mL) NaOH (2M, 1 mL) | Preparative HPLC, 14 mg | LC (METHOD 12): $t_R$ = 3.00 min; Mass spectrum (ES$^+$): m/z = 483 [M + H]$^+$. |
| 39 | 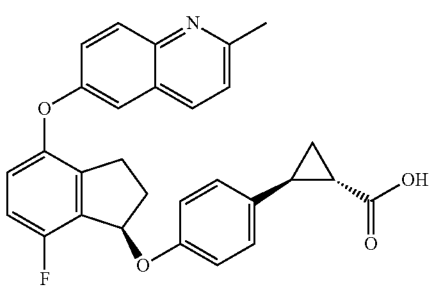 [SMILES: Cc1ccc2cc(Oc3ccc(F)c4c3CC[C@H]4Oc3ccc([C@H]4C[C@@H]4C(=O)O)cc3)ccc2n1] | Intermediate 55 (320 mg, crude) | Ethanol (5 mL) NaOH (2M, 0.5 mL) | Preparative HPLC, 117 mg | LC (METHOD 12): $t_R$ = 3.33 min; Mass spectrum (ES$^+$): m/z = 470 [M + H]$^+$. |
| 40 | 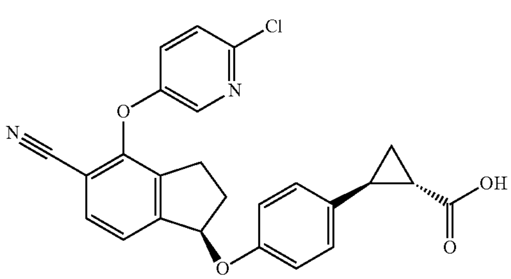 [SMILES: N#Cc1ccc2c(c1Oc1ccc(Cl)nc1)CC[C@H]2Oc1ccc([C@H]2C[C@@H]2C(=O)O)cc1] | Intermediate 56 (315 mg, crude) | Tetrahydrofuran (2 mL), methanol (2 mL), NaOH (1M, 2 mL) | Flash chromatography (0-2% MeOH in CH$_2$Cl$_2$) 130 mg | LC (METHOD 12): $t_R$ = 2.72 min; Mass spectrum (ES$^+$): m/z = 445 [M + H]$^+$. |

| Ex | Structure | Starting material | Solvent & Base | Purification & Yield | Analysis |
|---|---|---|---|---|---|
| 41 | 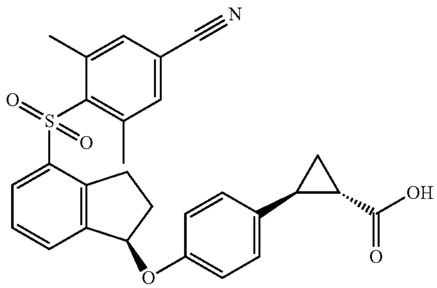 [SMILES: Cc1cc(C#N)cc(C)c1S(=O)(=O)c1cccc2c1CC[C@H]2Oc1ccc([C@H]2C[C@@H]2C(=O)O)cc1] | Intermediate 62 (163 mg) | Tetrahydrofuran (5 mL); water (0.5 mL), LiOH (32 mg) | Reverse phase (0-100% acetonitrile in water), 23 mg | LC (METHOD 12): $t_R$ = 2.77 min; Mass spectrum (ES-): m/z = 486 [M − H]⁻. |
| 42 | 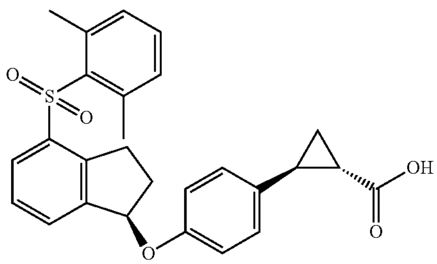 [SMILES: Cc1cccc(C)c1S(=O)(=O)c1cccc2c1CC[C@H]2Oc1ccc([C@H]2C[C@@H]2C(=O)O)cc1] | Intermediate 63 (138 mg) | Tetrahydrofuran (2 mL); MeOH; (2 mL); water (0.5 mL), LiOH (59 mg) | No purification, 110 mg | LC (METHOD 2): $t_R$ = 6.85 min; Mass spectrum (ES⁺): m/z = 463 [M + H]⁺. |
| 43 | 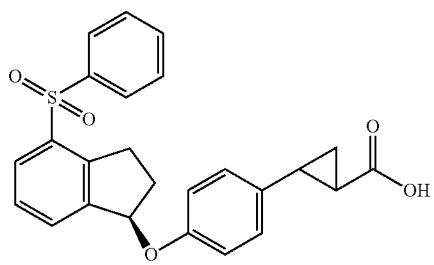 [SMILES: O=C(O)C1CC1c1ccc(O[C@@H]2CCc3c2cccc3S(=O)(=O)c2ccccc2)cc1] | Intermediate 64 (110 mg) | Methanol (2 mL), NaOH (1M, 1 mL) | Flash chromatography (0-10% MeOH in CH₂Cl₂) 56 mg | LC (METHOD 2): $t_R$ = 6.09 min; Mass spectrum (ES-): m/z = 433 [M − H]⁻. |
| 44 | 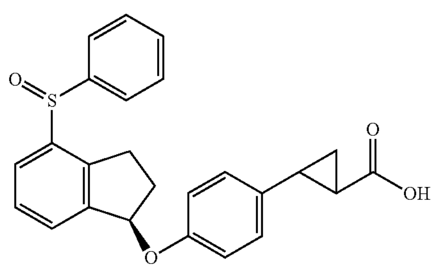 [SMILES: O=C(O)C1CC1c1ccc(O[C@@H]2CCc3c2cccc3S(=O)c2ccccc2)cc1] | Intermediate 65 (1 g, crude) | Methanol (10 mL), NaOH (32%, 60 uL) | Preparative HPLC, 10 mg | LC (METHOD 2): $t_R$ = 5.25 min; Mass spectrum (ES⁺): m/z = 419 [M + H]⁺. |

Example 45

(1S,2S)-2-[4-((R)-7-Fluoro-4-phenoxy-indan-1-yloxy)-phenyl]-cyclopropanecarboxylic acid

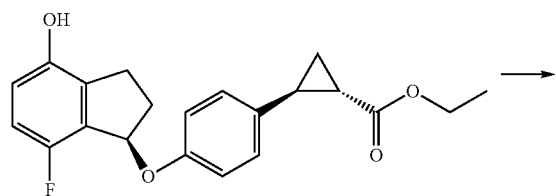

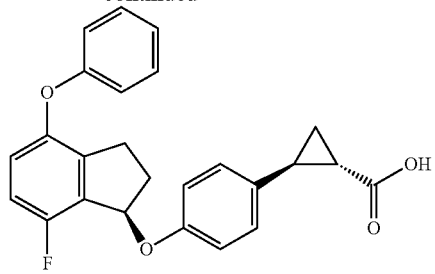

(1S,2S)-2-[4-((R)-7-Fluoro-4-hydroxy-indan-1-yloxy)-phenyl]-cyclopropanecarboxylic acid ethyl ester (Intermediate 5, 150 mg, 0.42 mmol), pyridine (dry; 0.133 mL, 1.68 mmol) and phenylboronic acid (308 mg, 2.53 mmol) are suspended in dichloromethane (10 mL), 4 Å molecular sieves and copper(II)acetate (153 mg, 1.52 mmol) are added and the mixture is stirred under oxygen atmosphere at room temperature for 20 h. NH$_4$OH (2 M aqueous solution, 20 mL) is added and the mixture is extracted with dichloromethane. The organic phase is collected, dried over sodium sulfate and concentrated under vacuum. The crude product is purified by flash chromatography (10-100% ethyl acetate in cyclohexane) to give the title compound (Yield: 40 mg). LC (METHOD 9): $t_R$=2.52 min; Mass spectrum (ES$^+$): m/z=405 [M+H]$^+$.

Example 46

(1S,2S)-2-{4-[(R)-5-Cyano-4-(6-methoxy-pyridin-3-ylmethyl)-indan-1-yloxy]-phenyl}-cyclopropanecarboxylic acid

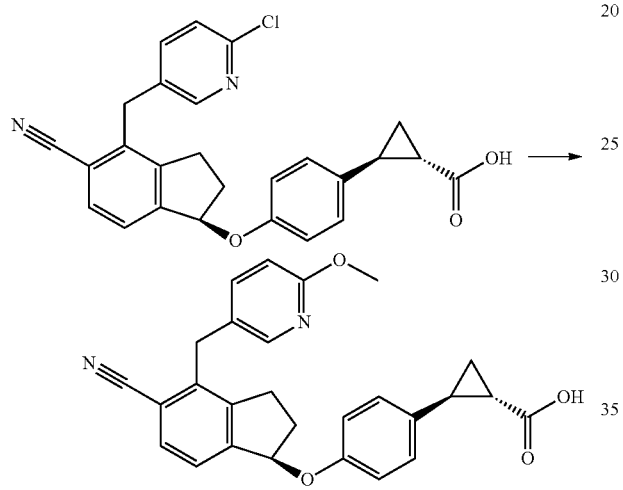

(1S,2S)-2-{4-[(R)-4-(6-Chloro-pyridin-3-ylmethyl)-5-cyano-indan-1-yloxy]-phenyl}-cyclopropanecarboxylic acid (Example 40, 100 mg, 0.22 mmol) is suspended in methanol (10 mL) and sodium hydride (60% in mineral oil, 27 mg, 0.67 mmol) is added. After 6 hours at 90° C. sodium methoxide (130 mg, 2.25 mmol) is added and the mixture stirred for 24 hours at 90° C. The solvent is removed under vacuum and the residue is purified by flash chromatography (0-10% MeOH in CH$_2$Cl$_2$) to give the title compound (Yield: 13 mg). LC (METHOD 3): $t_R$=4.04 min; Mass spectrum (ES$^+$): m/z=441 [M+H]$^+$.

The invention claimed is:
1. A compound of formula (I)

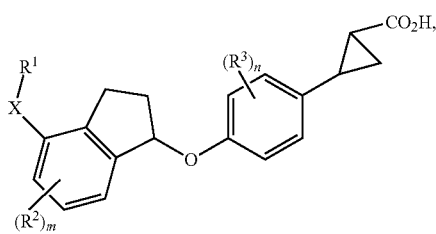

wherein:
R$^1$ is selected from the group consisting of a phenyl ring, a tetrazolyl ring,
   a 5-membered heteroaromatic ring containing 1 —NH—, —O—, or —S— group,
   a 5-membered heteroaromatic ring containing 1 —NH—, —O—, or —S— group and additionally 1 or 2 =N— atoms,
   a 6-membered heteroaromatic ring containing 1, 2 or 3 =N— atoms,
      wherein optionally a second ring is annulated to the phenyl ring or to the 5- or 6-membered heteroaromatic rings and the second ring is 5- or 6-membered, unsaturated or aromatic and optionally contains 1, 2, or 3 heteroatoms independently selected from =N—, —NH—, —O—, and —S— with the proviso that only up to two of the heteroatoms are O and S and no O—O, S—S, and S—O bond is formed, and wherein in the second ring independently of the presence of heteroatoms 1 or 2 CH$_2$ groups are optionally replaced by —C(O)—, —S(O)—, or —S(O)$_2$—,
      wherein the phenyl ring, tetrazolyl ring, 5- or 6-membered heteroaromatic ring, annulated phenyl ring, and annulated 5- or 6-membered heteroaromatic ring are optionally substituted at a carbon atom with one group R$^{1a}$, and
      wherein the phenyl ring, tetrazolyl ring, 5- or 6-membered heteroaromatic ring, annulated phenyl ring, and annulated 5- or 6-membered heteroaromatic ring are optionally additionally substituted at carbon atoms with 1 to 3 groups independently selected from R$^{1b}$, and
      wherein the H-atom in one or more NH groups present in the tetrazolyl ring, 5- or 6-membered heteroaromatic ring, annulated phenyl ring, or annulated 5- or 6-membered heteroaromatic ring optionally is replaced by R$^M$;
R$^2$ is F, Cl, Br, I, C$_{1-4}$-alkyl, C$_{3-6}$-cycloalkyl, NC—, H$_2$N—C(O)—, C$_{1-4}$-alkyl-NR$^M$—C(O)—, C$_{1-4}$-alkyloxy, or C$_{1-4}$-alkyl-S(O)$_2$—, wherein any alkyl and cycloalkyl group or sub-group thereof is optionally substituted with one or more F atoms, and wherein multiple R$^2$ are identical or different, if m is 2 or 3;
R$^3$ is F, Cl, Br, NC—, C$_{1-6}$-alkyl, C$_{3-6}$-cycloalkyl-, C$_{1-6}$-alkyl-O—, or C$_{3-6}$-cycloalkyl-O—, wherein each alkyl and cycloalkyl group and each alkyl and cycloalkyl sub-group thereof is optionally substituted with one or more F atoms;
X is —O—, >S=O, >S(=O)$_2$, —CH$_2$—, or —S—;
m is 0, 1, 2, or 3;
n is 0, 1, or 2;
R$^{1a}$ is selected from the group consisting of C$_{1-6}$-alkyl, C$_{2-6}$-alkenyl, C$_{2-6}$-alkynyl, C$_{3-6}$-cycloalkyl-, C$_{3-6}$-cycloalkyl-C$_{1-6}$-alkyl, C$_{1-4}$-alkyl-NH—, (C$_{1-4}$-alkyl)$_2$N—, —NHR$^N$, HNR$^M$—C(O)—, C$_{1-4}$-alkyl-NR$^M$—C(O)—, C$_{1-6}$-alkyl-O—, C$_{3-6}$-cycloalkyl-O—, C$_{3-6}$-cycloalkyl-C$_{1-6}$-alkyl-O—, C$_{1-4}$-alkyl-S—, C$_{1-4}$-alkyl-S(O)—, C$_{1-4}$-alkyl-S(O)$_2$, and aryl-C$_{1-3}$-alkyl-O—,
      wherein a —CH$_2$— member within a C$_{4-6}$-cycloalkyl-group or sub-group within the groups thereof is optionally replaced by —NR$^N$—, —O—, —S—, —S(O)—, or —S(O$_2$)—, or
      wherein a >CH—CH$_2$— member or a —CH$_2$—CH$_2$— member within a C$_{5-6}$-cycloalkyl-group or sub-group within the groups thereof is optionally replaced by >N—C(O)—, >N—S(O)—, >N—S(O)$_2$—, —N(R$^M$)—C(O)—, —N(R$^M$)—S(O)—, or —N(R$^M$)—S(O)$_2$—, and wherein each alkyl and cycloalkyl group and each alkyl and cycloalkyl sub-group within the groups thereof is optionally substituted with HO—, HO—C$_{1-4}$-alkyl-, C$_{1-4}$-alkyl-oxy, C$_{1-4}$-alkyl-oxy-C$_{1-4}$-alkyl-, C$_{1-4}$-alkyl-sulfanyl, C$_{1-4}$-alkyl-sulfinyl, C$_{1-4}$-alkyl-sulfonyl, H$_2$N—C(O)—, C$_{1-4}$-alkyl-NH—C(O)—, (C$_{1-4}$-alkyl)$_2$N—C(O)—, or C$_{3-6}$-cycloalkyl-NR$^M$—C(O)—, and/or optionally substituted with one or more F atoms, a phenyl ring, a tetrazolyl ring, a 5-membered heteroaromatic ring containing 1 —NH—, —O—, or —S— group, a 5-membered heteroaromatic ring containing 1 —NH—, —O—, or —S— group and additionally 1 or 2 =N— atoms, a 6-membered heteroaromatic ring containing 1, 2, or 3 =N— atoms, wherein the rings are optionally substituted with one or more groups selected from R$^{1b}$, and wherein the H-atom in one or more NH groups present in the tetrazolyl ring or 5-membered heteroaromatic ring is replaced by R$^M$;

R$^{1b}$ is F, Cl, CN, —OH, C$_{1-4}$-alkyl, C$_{3-6}$-cycloalkyl-, HO—C$_{1-4}$-alkyl, C$_{1-4}$-alkyl-O—C$_{1-4}$-alkyl, C$_{1-4}$-alkyl-O—, C$_{3-6}$-cycloalkyl-O—, C$_{1-4}$-alkyl-O—C$_{1-4}$-alkyl-O—, C$_{1-4}$-alkyl-S—, C$_{1-4}$-alkyl-S(O)—, or C$_{1-4}$-alkyl-S(O)$_2$—, wherein any alkyl and cycloalkyl group or sub-group within the groups thereof is optionally substituted with one or more F atoms;

R$^N$ is independently H, C$_{1-4}$-alkyl, HO—C$_{2-4}$-alkyl (with the proviso that at least 2 carbon atoms are between the HO-group and an NH), C$_{1-4}$-alkyl-O—C$_{2-4}$-alkyl-(with the proviso that at least 2 carbon atoms are between an O-group and an NH), C$_{1-4}$-alkyl-C(O)—, C$_{1-4}$-alkyl-O—C(O)—, or C$_{1-4}$-alkyl-S(O)$_2$—, wherein any alkyl group or sub-group within the groups thereof is optionally substituted with one or more F atoms; and R$^M$ is independently H, C$_{1-4}$-alkyl, HO—C$_{2-4}$-alkyl (with the proviso that at least 2 carbon atoms are between the HO-group and an NH), or C$_{1-4}$-alkyl-O—C$_{2-4}$-alkyl-(with the proviso that at least 2 carbon atoms are between an O-group and an NH), wherein any alkyl group or sub-group within the groups thereof is optionally substituted with one or more F atoms, or a salt thereof.

2. The compound according to claim 1, wherein:

R$^1$ is selected from the group consisting of a phenyl ring, a tetrazolyl ring, a 5-membered heteroaromatic ring containing 1 —NH— or —O— group, a 5-membered heteroaromatic ring containing 1 —NH— or —O— group and additionally 1 or 2 =N— atoms, a 6-membered heteroaromatic ring containing 1, 2, or 3 =N— atoms, wherein the phenyl ring, tetrazolyl ring, and 5- or 6-membered heteroaromatic ring are optionally substituted at a carbon atom with one group R$^{1a}$, and wherein the phenyl ring, tetrazolyl ring, 5- or 6-membered heteroaromatic ring are optionally additionally substituted at carbon atoms with 1 to 3 groups independently selected from R$^{1b}$, and wherein the H-atom in one or more NH groups present in the tetrazolyl ring, 5- or 6-membered heteroaromatic ring optionally is replaced by R$^M$;

X is —O—, >S=O, >S(=O)$_2$, or —CH$_2$—;

m is 1 or 2;

n is 0 or 1;

R$^{1a}$ is selected from the group consisting of C$_{1-4}$-alkyl, C$_{2-4}$-alkenyl, C$_{2-4}$-alkynyl, C$_{3-6}$-cycloalkyl-, C$_{3-6}$-cycloalkyl-C$_{1-4}$-alkyl, C$_{1-4}$-alkyl-NH—, (C$_{1-4}$-alkyl)$_2$N—, —NHR$^N$, HNR$^M$—C(O)—, C$_{1-4}$-alkyl-NR$^M$—C(O)—, C$_{1-6}$-alkyl-O—, C$_{3-6}$-cycloalkyl-O—, C$_{3-6}$-cycloalkyl-C$_{1-4}$-alkyl-O—, C$_{1-4}$-alkyl-S(O)$_2$, and aryl-C$_{1-3}$-alkyl-O—, wherein a —CH$_2$— member within a C$_{4-6}$-cycloalkyl-group or sub-group within the groups thereof is optionally replaced by —NR$^N$—, —O—, or —S(O$_2$)—, or wherein a >CH—CH$_2$— member or a —CH$_2$—CH$_2$— member within a C$_{5-6}$-cycloalkyl-group or sub-group within the groups thereof is optionally replaced by >N—C(O)—, >N—S(O)$_2$—, —N(R$^M$)—C(O)—, or —N(R$^M$)—S(O)$_2$—, and wherein each alkyl and cycloalkyl group and each alkyl and cycloalkyl sub-group within the groups thereof is optionally substituted with HO—, HO—C$_{1-3}$-alkyl-, C$_{1-3}$-alkyl-oxy, C$_{1-3}$-alkyloxy-O$_{1-4}$-alkyl-, C$_{1-4}$-alkyl-sulfonyl, H$_2$N—C(O)—, C$_{1-4}$-alkyl-NH—C(O)—, or (C$_{1-4}$-alkyl)$_2$N—C(O)—, and/or optionally substituted with 1 to 3 F atoms;

R$^{1b}$ is F, Cl, CN, —OH, C$_{1-3}$-alkyl, C$_{3-6}$-cycloalkyl-, HO—C$_{1-3}$-alkyl, C$_{1-3}$-alkyl-O—, or C$_{3-6}$-cycloalkyl-O—, wherein any alkyl and cycloalkyl group or sub-group within the groups thereof is optionally substituted with 1 to 3 F atoms;

R$^N$ is H, C$_{1-4}$-alkyl, HO—C$_{1-4}$-alkyl (with the proviso that at least 2 carbon atoms are between the HO-group and an NH), C$_{1-4}$-alkyl-C(O)—, C$_{1-3}$-alkyl-O—C(O)—, or C$_{1-3}$-alkyl-S(O)$_2$—, wherein any alkyl group or sub-group within the groups thereof is optionally substituted with 1 to 3 F atoms; and R$^M$ is H, C$_{1-3}$-alkyl, HO—C$_{2-4}$-alkyl (with the proviso that at least 2 carbon atoms are between the HO-group and an NH), or C$_{1-3}$-alkyl-O—C$_{2-3}$-alkyl-(with the proviso that at least 2 carbon atoms are between an O-group and an NH), wherein any alkyl group or sub-group within the groups thereof is optionally substituted with 1 to 5 F atoms, or a salt thereof.

3. The compound according to claim 1, wherein

R$^{1a}$ is selected from the group consisting of a phenyl ring, a tetrazolyl ring, a 5-membered heteroaromatic ring containing 1 —NH— or —O— group, a 5-membered heteroaromatic ring containing 1 —NH— or —O— group and additionally 1 or 2 =N— atoms, a 6-membered heteroaromatic ring containing 1 or 2 =N— atoms, wherein the rings are optionally substituted with one to three groups selected from R$^{1b}$, and wherein the H-atom in one or more NH groups present in the tetrazolyl ring or 5-membered heteroaromatic ring is replaced by R$^M$, or a salt thereof.

4. The compound according to claim 1, wherein:

$R^2$ is F, Cl, Br, I, $C_{1-3}$-alkyl, $C_{3-6}$-cycloalkyl, NC—, $H_2N$—C(O)—, or $C_{1-3}$-alkyloxy, wherein any alkyl and cycloalkyl group or sub-group within the groups thereof is optionally substituted with 1 to 3 F atoms, and wherein multiple $R^2$ are identical or different, if m is 2 or 3; and X is —O—, >S=O, >S(=O)$_2$, and —CH$_2$—, or a salt thereof.

5. The compound according to claim 1, wherein:

$R^3$ is F, Cl, Br, NC—, $C_{1-4}$-alkyl, $C_{3-6}$-cycloalkyl-, $C_{1-4}$-alkyl-O—, or $C_{3-6}$-cycloalkyl-O—, wherein each alkyl and cycloalkyl group and each alkyl and cycloalkyl sub-group within the groups thereof is optionally substituted with 1 to 3 F atoms; and X is —O—, >S=O, >S(=O)$_2$, and —CH$_2$—, or a salt thereof.

6. The compound according to claim 1, wherein the compound has the stereochemistry shown in formula I.1 or I.2

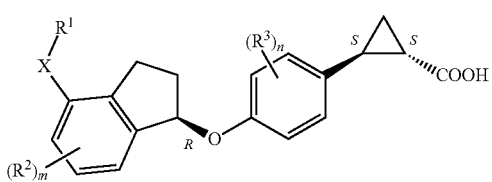

I.1

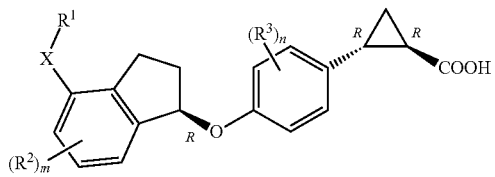

I.2 or a salt thereof.

7. A pharmaceutically acceptable salt of a compound according to claim 1.

8. A pharmaceutical composition comprising a compound according to claim 1 or a pharmaceutically acceptable salt thereof and an inert carrier or diluent.

9. The pharmaceutical composition according to claim 8, further comprising an additional therapeutic agent.

10. The pharmaceutical composition according to claim 9, wherein the additional therapeutic agent is an antidiabetic agent, an agent for the treatment of overweight and/or obesity, or an agent for the treatment of high blood pressure, heart failure, and/or atherosclerosis.

11. A method for treating a disease or condition which can be influenced by the modulation of the function of GPR40 in a patient having said disease or condition, the method comprising administering to the patient an effective amount of a compound according to claim 1.

12. The method according to claim 11, wherein the disease or condition is a metabolic disease.

13. The method according to claim 11, wherein the disease or condition is type 2 diabetes mellitus, insulin resistance, obesity, cardiovascular disease, or dyslipidemia.

* * * * *